United States Patent
Steil et al.

(10) Patent No.: US 6,558,351 B1
(45) Date of Patent: May 6, 2003

(54) CLOSED LOOP SYSTEM FOR CONTROLLING INSULIN INFUSION

(75) Inventors: Garry M. Steil, Pasadena, CA (US); Kerstin Rebrin, South Pasadena, CA (US); Paul V. Goode, Jr., Valencia, CA (US); John J. Mastrototaro, Los Angeles, CA (US); Richard E. Purvis, Pasadena, CA (US); William P. Van Antwerp, Valencia, CA (US); John J. Shin, Glendale, CA (US); Cary D. Talbot, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 281 days.

(21) Appl. No.: 09/586,175

(22) Filed: Jun. 1, 2000

Related U.S. Application Data

(60) Provisional application No. 60/137,601, filed on Jun. 3, 1999, and provisional application No. 60/162,255, filed on Oct. 29, 1999.

(51) Int. Cl.[7] .................. A61M 37/00; A61M 31/00
(52) U.S. Cl. ....................... 604/131; 604/522
(58) Field of Search ............... 604/131, 31, 522, 604/500, 30, 93.01

(56) References Cited

U.S. PATENT DOCUMENTS

| | | | |
|---|---|---|---|
| 3,621,357 A | * 11/1971 | Kubo et al. | 318/600 |
| 3,826,887 A | * 7/1974 | Pemberton | 219/497 |
| 3,834,617 A | * 9/1974 | Dyntar | 236/1 C |
| 3,986,571 A | * 10/1976 | Strobel et al. | 177/185 |
| 4,291,692 A | * 9/1981 | Bowman et al. | 604/31 |
| 4,786,394 A | 11/1988 | Enzer et al. | 204/401 |
| 5,050,612 A | 9/1991 | Matsumura | 128/670 |
| 5,068,536 A | 11/1991 | Rosenthal | 250/341 |
| 5,497,772 A | 3/1996 | Schulman et al. | 128/635 |
| 5,507,288 A | 4/1996 | Böcker et al. | 128/633 |
| 5,569,186 A | 10/1996 | Lord et al. | 604/67 |
| 5,665,065 A | 9/1997 | Colman et al. | 604/66 |
| 5,695,464 A | * 12/1997 | Viallet | 604/67 |
| 5,813,403 A | 9/1998 | Soller et al. | 128/633 |
| 5,830,133 A | 11/1998 | Osten et al. | 600/322 |
| 5,885,211 A | 3/1999 | Eppstein et al. | 600/309 |
| 6,049,727 A | 4/2000 | Crothall | 600/310 |
| 6,088,608 A | 7/2000 | Schulman et al. | 600/345 |
| 6,416,293 B1 | * 7/2002 | Bouchard et al. | 417/53 |
| 6,424,873 B1 | * 7/2002 | Przybylski | 700/42 |

OTHER PUBLICATIONS

Bellazzi, Riccardo, et al., "The Subcutaneous Route to Insulin–Dependent Diabetes Therapy", *IEEE Engineering in Medicine and Biology*, pp. 54–64 (Jan./Feb. 2001).

Parker, Robert S., et al., "The Intravenous Route to Blood Glucose Control", *IEEE Engineering in Medicine and Biology*, pp. 65–73 (Jan./Feb. 2001).

\* cited by examiner

*Primary Examiner*—Teresa Walberg
*Assistant Examiner*—Daniel Robinson
(74) *Attorney, Agent, or Firm*—Medtronic MiniMed, Inc.

(57) ABSTRACT

A closed loop infusion system controls the rate that fluid is infused into the body of a user. The closed loop infusion system includes a sensor system, a controller, and a delivery system. The sensor system includes a sensor for monitoring a condition of the user. The sensor produces a sensor signal, which is representative of the condition of the user. The sensor signal is used to generate a controller input. The controller uses the controller input to generate commands to operate the delivery system. The delivery system infuses a liquid into the user at a rate dictated by the commands from the controller. Preferably, the sensor system monitors the glucose concentration in the body of the user, and the liquid infused by the delivery system into the body of the user includes insulin. The sensor system uses the sensor signal to generate a message that is sent to the delivery system. The message includes the information used to generate the controller input. The sensor may be a subcutaneous sensor in contact with interstitial fluid. Also, two or more sensors may be used by the sensor system.

14 Claims, 37 Drawing Sheets

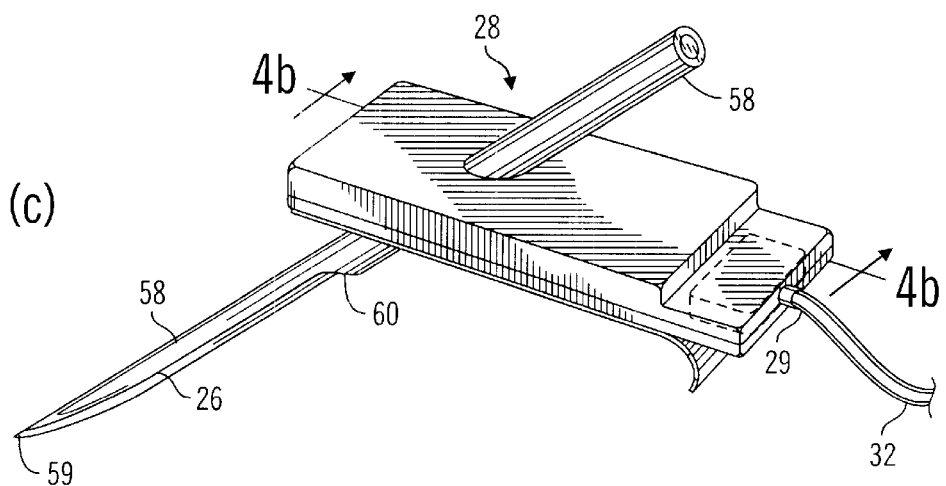
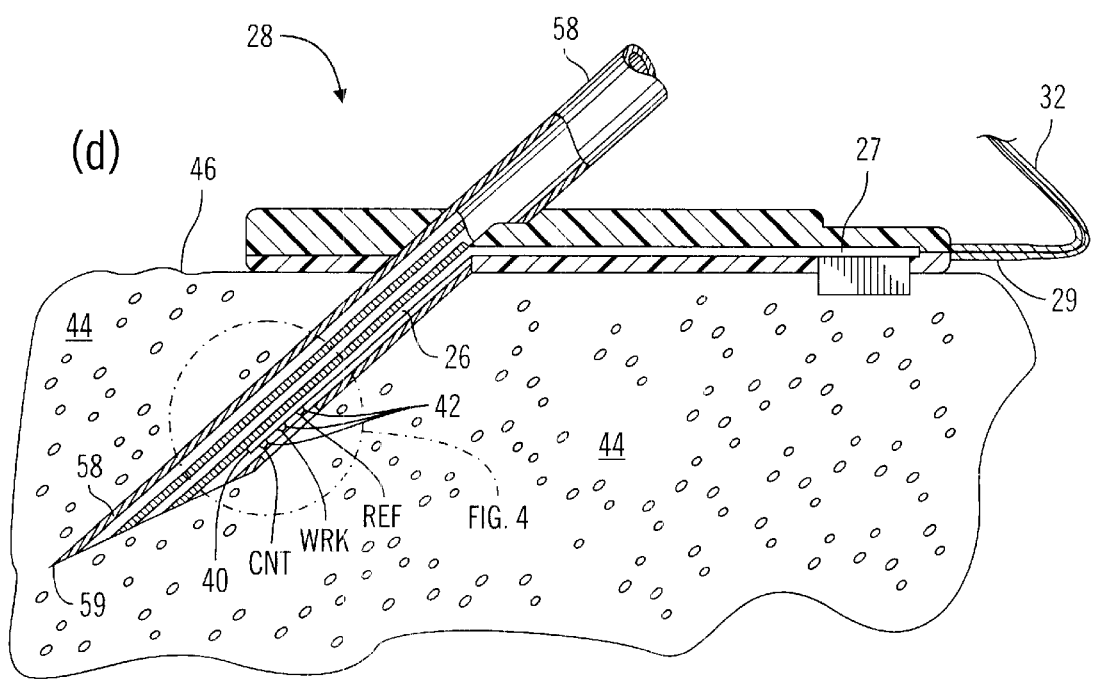
FIG. 3

| COMPONENTS | ALTERNATIVE, FIG. 8(a) | | PREFERRED EMBODIMENT, FIG. 8(b) | | ALTERNATIVE, FIG. 8(c) | | ALTERNATIVE, FIG. 8(d) | |
|---|---|---|---|---|---|---|---|---|
| | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | INFUSION PUMP | TELEMETERED CHARACTERISTIC MONITOR TRANSMITTER | SUPPLEMENTAL INFUSION DEVICE PUMP |
| PRE-FILTERS | | X | X | | | X | | |
| FILTERS | | X | X | | X | X | X | X |
| CALIBRATOR | | X | X | | | X | | X |
| CONTROLLER | | X | | X | | X | | X |

FIG. 9

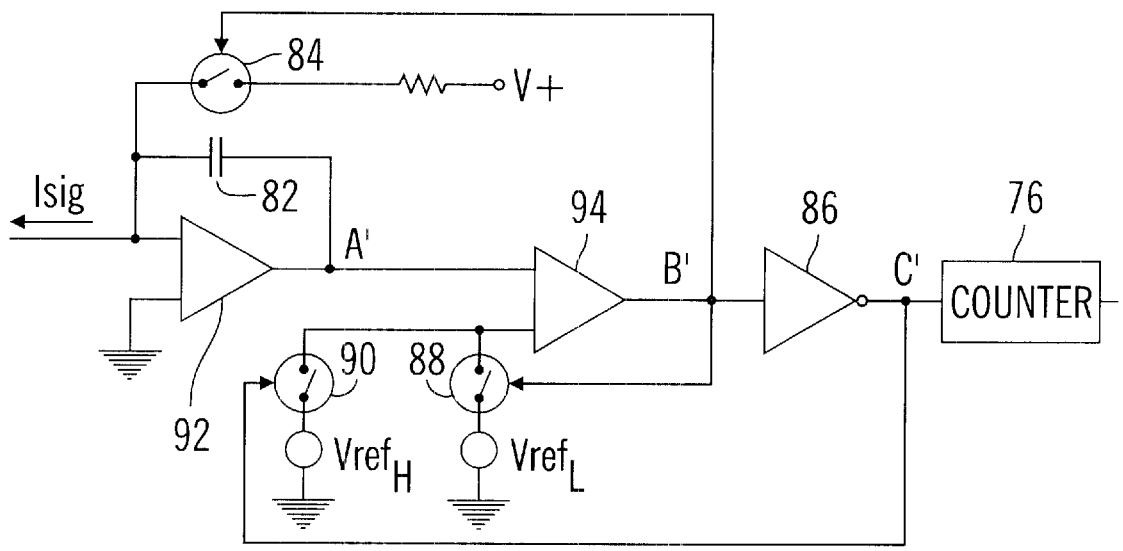
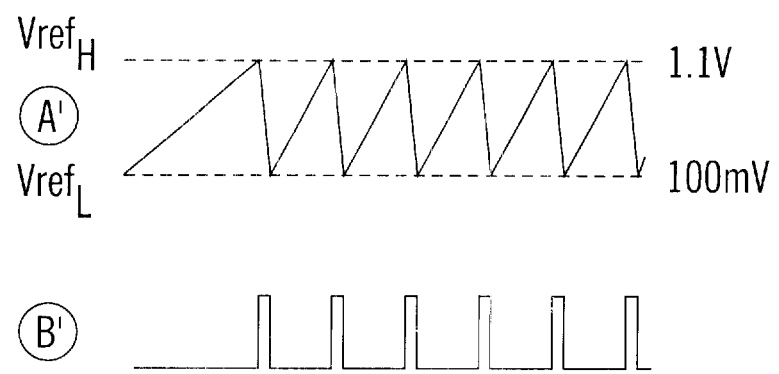
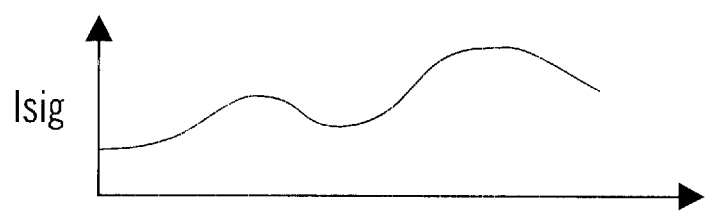
FIG. 12

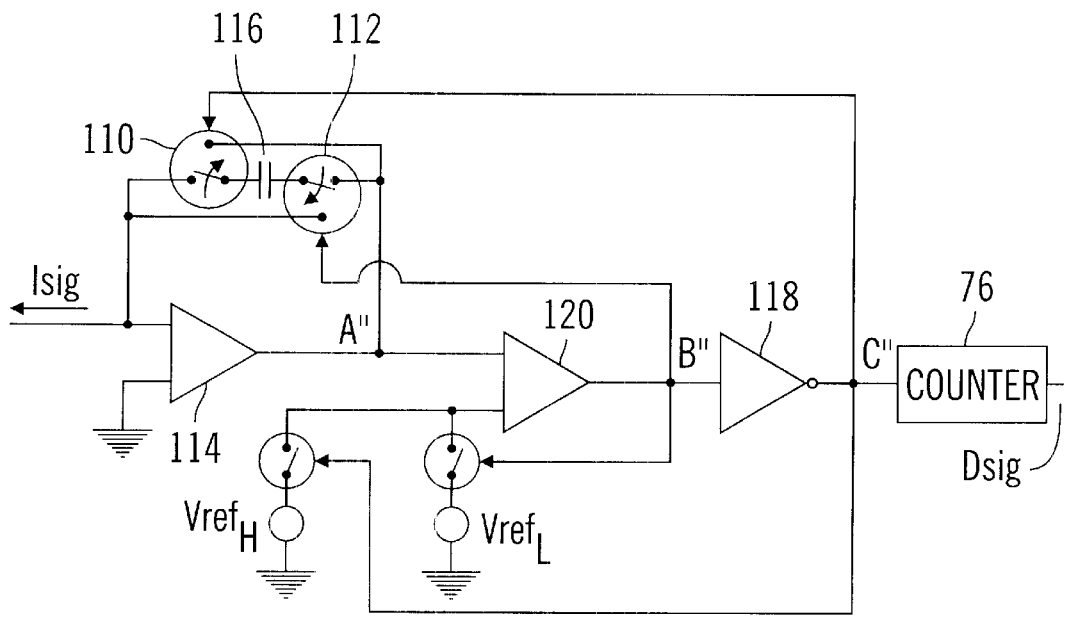
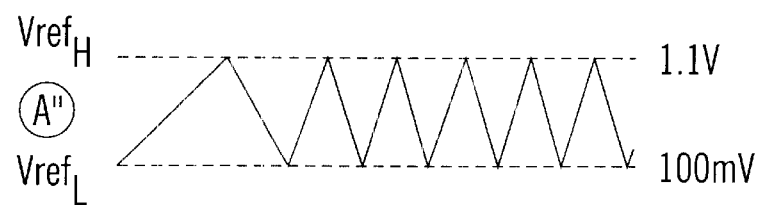
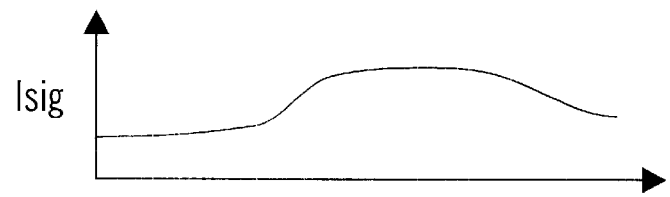
FIG. 13

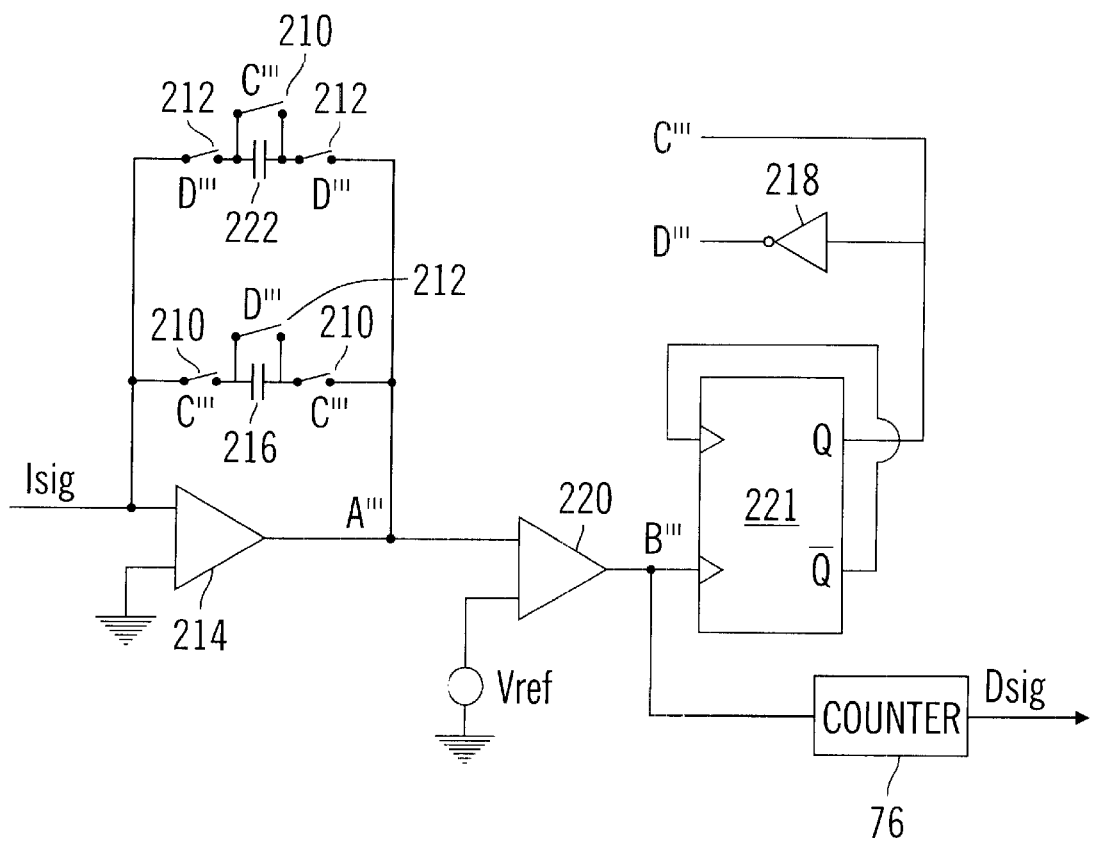
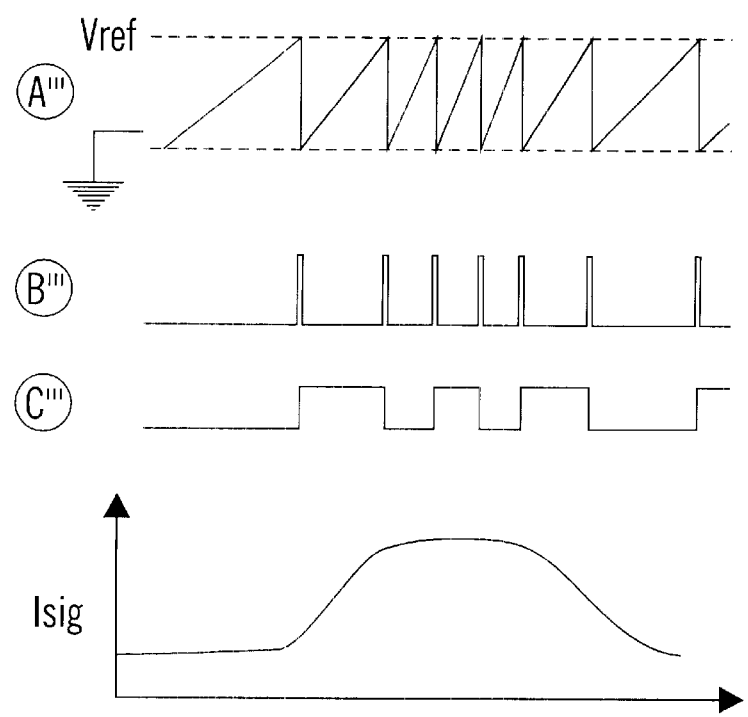
FIG. 14

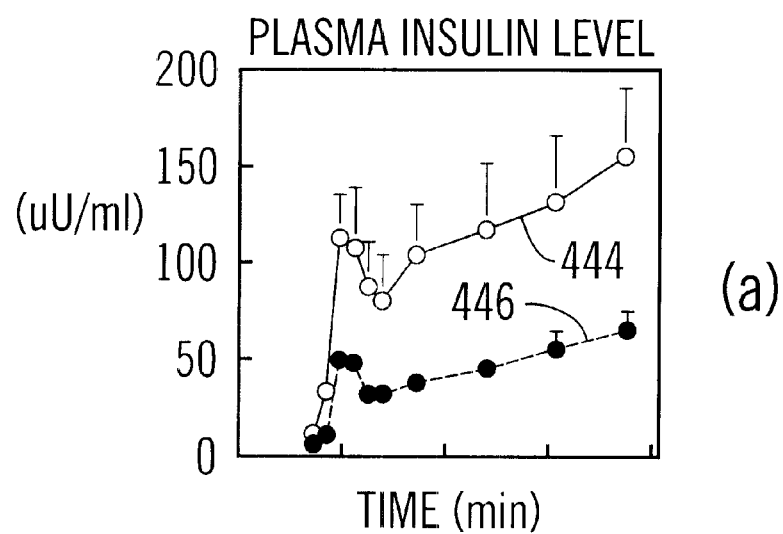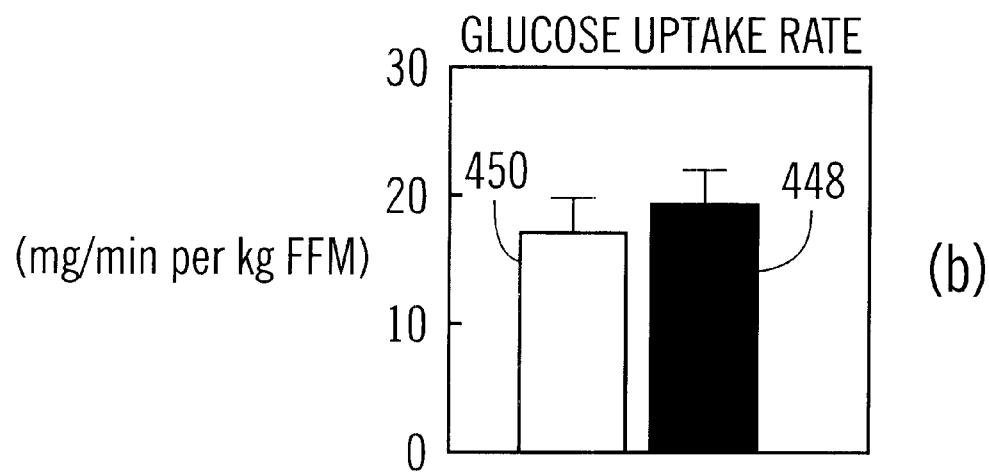
FIG. 25

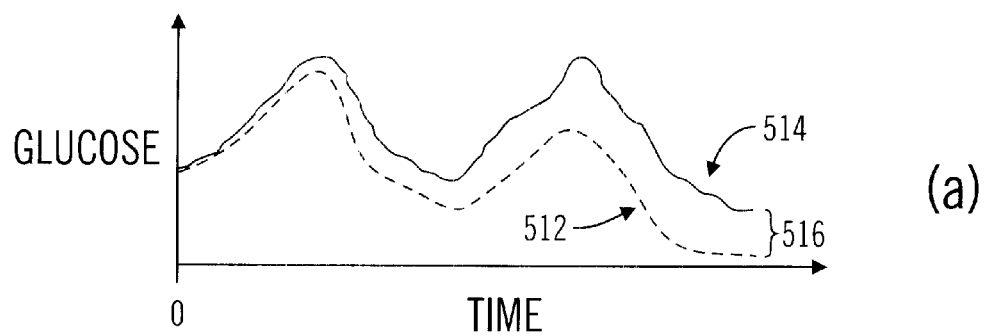
(a)
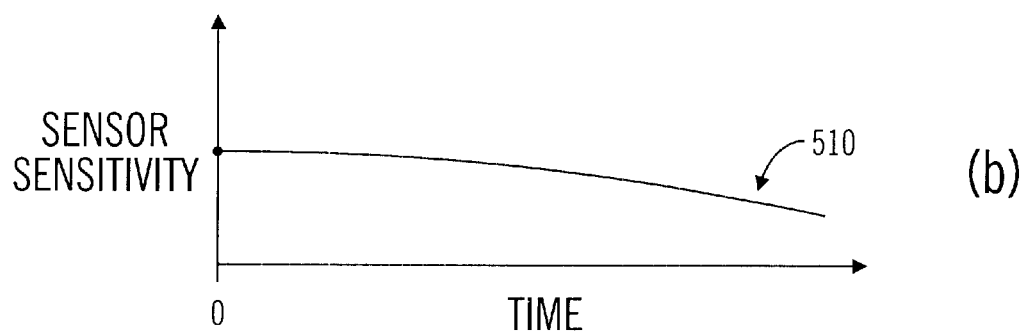
(b)
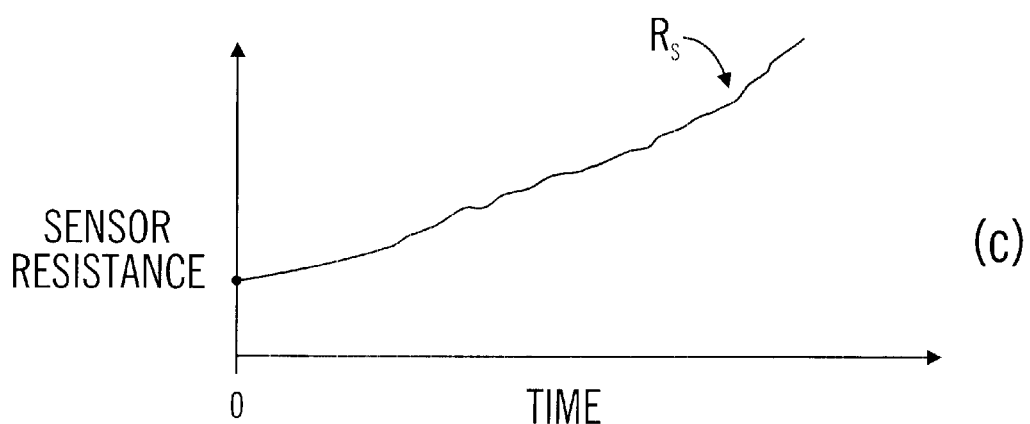
(c)
FIG. 31

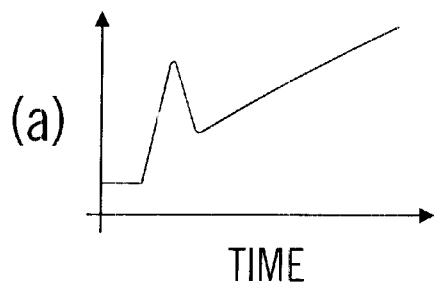
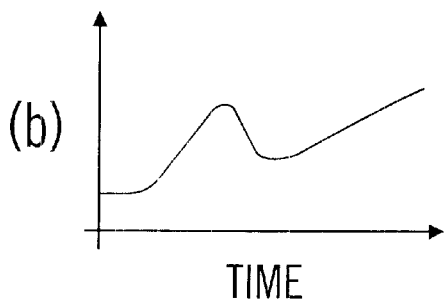
FIG. 35
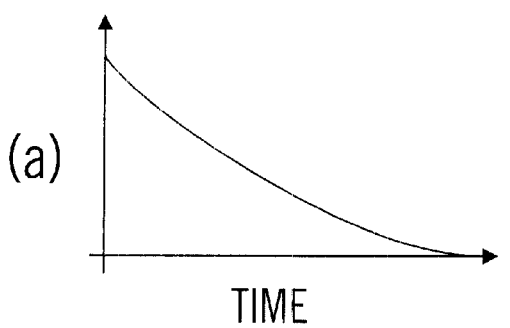
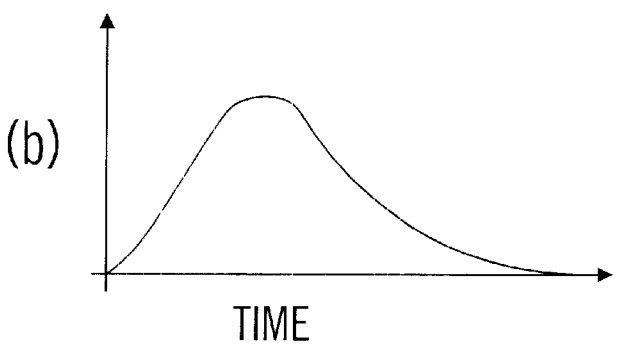
FIG. 36

CLOSED LOOP SYSTEM FOR CONTROLLING INSULIN INFUSION

RELATED APPLICATIONS

This application claims priority on U.S. Provisional Application Ser. No. 60/137,601 filed Jun. 3, 1999, entitled "Closed Loop Algorithms For Continuous Monitoring And Insulin Infusion", and U.S. Provisional Application Ser. No. 60/162,255 filed October 29, 1999 and entitled "Closed Loop Algorithms For Continuous Monitoring And Insulin Infusion", both of which are specifically incorporated by reference herein.

FIELD OF THE INVENTION

This invention relates to closed loop drug delivery systems and more specifically to systems for controlling the infusion rate of insulin based on continuously monitored body glucose levels.

BACKGROUND OF THE INVENTION

The pancreas of a normal healthy person produces and releases insulin into the blood stream in response to elevated blood plasma glucose levels. Bata cells ($\beta$-cells), which reside in the pancreas, produce and secrete the insulin into the blood stream, as it is needed. If $\beta$-cells become incapacitated or die, a condition known as Type I diabetes mellitus (or in some cases if $\beta$-cells produce insufficient quantities of insulin, Type II diabetes), then insulin must be provided to the body from another source.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. As of 1995, less than 5% of Type I diabetics in the United States were using infusion pump therapy. Presently over 7% of the more than 900,000 Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin using Type II diabetics are also using infusion pumps. Physicians have recognized that continuous infusion provides greater control of a diabetic's condition, and are also increasingly prescribing it for patients. Although offering control, pump therapy can suffer from several complications that make use of traditional external infusion pumps less desirable for the user.

SUMMARY OF THE DISCLOSURE

According to an embodiment of the invention, a closed loop infusion system is for controlling blood glucose concentration in the body of a user. Embodiments of the present invention include a sensor system that measures a glucose level in the body of the user, a controller that uses the measured glucose level to generate commands, and an insulin infusion system that infuses insulin into the body of the user in response to the commands.

According to another embodiment of the invention, a closed loop infusion system is for infusing a fluid into a user. The closed loop infusion system includes a sensor system, a controller, and a delivery system. The sensor system includes a sensor for monitoring a condition of the user. The sensor produces a sensor signal, which is representative of the condition of the user, and is used to generate a controller input. The controller uses the controller input to generate commands that affect the operation of the delivery system. Accordingly, the delivery system infuses a liquid into the user. In particular embodiments, glucose concentration is monitored by the sensor system, and the liquid delivered to the user includes insulin. In preferred embodiments, the sensor system sends a message, generated using the sensor signal, to the delivery system. The message is used to generate the controller input. In particular embodiments, the sensor is a subcutaneous sensor in contact with interstitial fluid. In further particular embodiments, two or more sensors are included in the sensor system.

In preferred embodiments, the sensor system is predominately external to the user's body. And the delivery system is predominately external to the user's body. In alternative embodiments, the sensor system is predominately internal to the user's body. In other alternative embodiments, the delivery system is predominately internal to the user's body.

In preferred embodiments, the sensor signal is used to generate digital sensor values, and the digital sensor values are processed through at least one of a group of components that includes one or more pre-filters, one or more filters, one or more calibrators and one or more post-calibration filters to generate the controller input. In particular embodiments, the one or more pre-filters uses a group of digital sensor values, calculates a parameter using at least a subset of the group of digital sensor values, establishes one or more thresholds relative to the parameter, compares each digital sensor value within the group to the one or more thresholds, and changes the value of any digital sensor value that is outside of the one or more thresholds. In further particular embodiments, the one or more pre-filters compares the digital sensor values to one or more thresholds, and a flag is set when one or more digital sensor values are outside of at least one threshold.

In preferred embodiments, the digital sensor values are processed through at least one FIR filter, preferably at least a $7^{th}$ order FIR filter. In addition, a preferred FIR filter has a pass band for frequencies from zero up to between about 2 cycles/hour and 5 cycles/hour and a stop band beginning at 1.2 to three times the selected pass band frequency. In particular embodiments, the FIR filter has a pass band for frequencies from zero up to between about 2 cycles/hour and 10 cycles/hour and a stop band beginning at 1.2 to three times the selected pass band frequency. In other particular embodiments, the FIR filter has a pass band for frequencies from zero up to less than or equal to 10 cycles/hour. Preferred embodiments include a FIR filter that compensates for time delays of between zero and 30 minutes. In particular embodiments, the FIR filter compensates for time delays of between 3 and 10 minutes.

In preferred embodiments, the controller uses a first set of one or more controller gains when the glucose concentration is higher than a desired basal glucose concentration and the controller uses a second set of one or more controller gains when the glucose concentration is lower than a desired basal glucose concentration. In alternative embodiments, the controller uses a first set of one or more controller gains when the glucose concentration is increasing and a second set of one or more controller gains when the glucose concentration is decreasing. In further alternative embodiments, the controller uses a first set of one or more controller gains when the glucose concentration is higher than a desired basal glucose concentration and the glucose concentration is increasing; and the controller uses a second set of one or more controller gains when the glucose concentration is higher than a desired basal glucose concentration and the glucose concentration is decreasing; and the controller uses a third set of one or more controller gains when the glucose concentration is lower than a desired basal glucose concentration and the glucose concentration is increasing; and the controller uses a fourth set of one or more controller gains when the glucose concentration is lower than a desired basal glucose concentration and the glucose concentration is decreasing.

In preferred embodiments, one or more controller gains are selected such that the commands generated by the controller cause the delivery system to infuse insulin into the body of the user in response to a glucose concentration at a rate similar to the rate that beta cells would release insulin in an individual with a healthy normally functioning pancreas. Alternatively, one or more controller gains are selected so that the commands generated by the controller cause the delivery system to infuse insulin into the body of the user in response to a glucose concentration at a rate such that the insulin concentration profile in the user's blood stream is similar to the insulin concentration profile that would be generated by the release of insulin beta cells in an individual with a healthy normally functioning pancreas. In other alternative embodiments, a post-controller lead/lag compensator is used to modify the commands generated by the controller to cause the delivery system to infuse insulin into the body of the user in response to a glucose concentration at a rate such that the insulin concentration profile in the user's blood stream is similar to the insulin concentration profile that would be generated by the release of insulin beta cells in an individual with a healthy normally functioning pancreas.

In preferred embodiments, one or more controller gains are selected by a method that includes the step of measuring an insulin response of at least one individual with a healthy normally functioning pancreas and calculating the controller gains that cause the commands to generally match the insulin response of at least one individual. In particular embodiments, the derivative gain $K_D$ is calculated using the first phase insulin response ($\phi 1$) measured from a normal glucose tolerant (NGT) individual. In further particular embodiments, one or more controller gains are calculated from a ratio of one or more controller gains.

In preferred embodiments, a post-controller lead/lag compensator is used to modify the commands generated by the controller to compensate for an insulin delivery delay due to infusing insulin into a user' tissue rather than directly into the user's blood stream.

In alternative embodiments, the controller is influenced by inputs of more than one measured body characteristic. For example, measured body characteristics that might be used to influence the controller include one or more amino acid concentrations, one or more gastrointestinal hormone concentrations, one or more other hormone concentrations, blood pH, interstitial fluid (ISF) pH, one or more blood glucose concentrations, and one or more interstitial fluid (ISF) glucose concentrations. In particular embodiments, the sensor is a multi-sensor that measures both glucose concentration and pH.

In preferred embodiments, the sensor system produces a diagnostic signal in addition to the sensor signal, and the diagnostic signal is used to indicate when the sensor signal accuracy has diminished.

According to an embodiment of the invention, a closed loop infusion system is for infusing a fluid into a user.

Embodiments of the invention include a sensor system, a proportional plus, integral plus, derivative (PID) controller, and a delivery system. The sensor system includes a sensor for monitoring glucose concentration of the user. The sensor system produces a sensor signal, which is representative of the glucose concentration of the user, and the sensor signal is used to generate a controller input. The controller uses the controller input to generate commands. The delivery system infuses a liquid, which includes insulin, into the user, and the operation of the delivery system is affected by the commands. In particular embodiments, the controller is influenced by one or more manual inputs from the user. The manual inputs from the user may include one or more of the start of a meal, the number of carbohydrates in a meal, the beginning of exercise for the body of the user, the duration of the exercise for the body of the user, the start of sleep for the user, and the duration of sleep for the user.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIGS. 9 is a table listing the devices of FIGS. 8(a–d) and their components.

FIG. 12 is a circuit diagram of an I-F A/D converter of FIG. 10 accompanied by charts of node signals in accordance with an embodiment of the present invention.

FIG. 13 is another circuit diagram of an I-F A/D converter of FIG. 10 accompanied by charts of node signals in accordance with an embodiment of the present invention.

FIG. 14 is still another circuit diagram of an I-F A/D converter of FIG. 10 accompanied by charts of node signals in accordance with an embodiment of the present invention.

FIG. 25(a) is a plot of insulin responses to a glucose clamp for exercise trained and normal individuals.

FIG. 25(b) is a bar chart of glucose uptake rates for exercise trained and normal individuals.

FIG. 31(a) is a representative drawing of blood glucose compared to sensor measured blood glucose over time in accordance with an embodiment of the present invention.

FIG. 31(b) is a representative drawing of sensor sensitivity over the same period of time as FIG. 31(a) in accordance with an embodiment of the present invention.

FIG. 31 (c) is a representative drawing of sensor resistance over the same period of time as FIG. 31(a) in accordance with an embodiment of the present invention.

FIG. 35(a) is a drawing of a blood plasma insulin response to a glucose clamp in a normal glucose tolerant (NGT) individual in accordance with an embodiment of the present invention.

FIG. 35(b) is a drawing of the blood plasma insulin response of FIG. 35(a) when delayed due to insulin being delivered to the subcutaneous tissue instead of directly into the blood stream in accordance with an embodiment of the present invention.

FIG. 36(a) is a drawing of blood plasma insulin concentration over time after an insulin bolus is delivered directly into the blood stream in accordance with an embodiment of the present invention.

FIG. 36(b) is a drawing of a blood plasma insulin concentration over time after an insulin bolus is delivered into the subcutaneous tissue in accordance with an embodiment of the present invention.

DETAILED DESCRIPTION OF THE PREFERRED EMBODIMENTS

Figure 1:
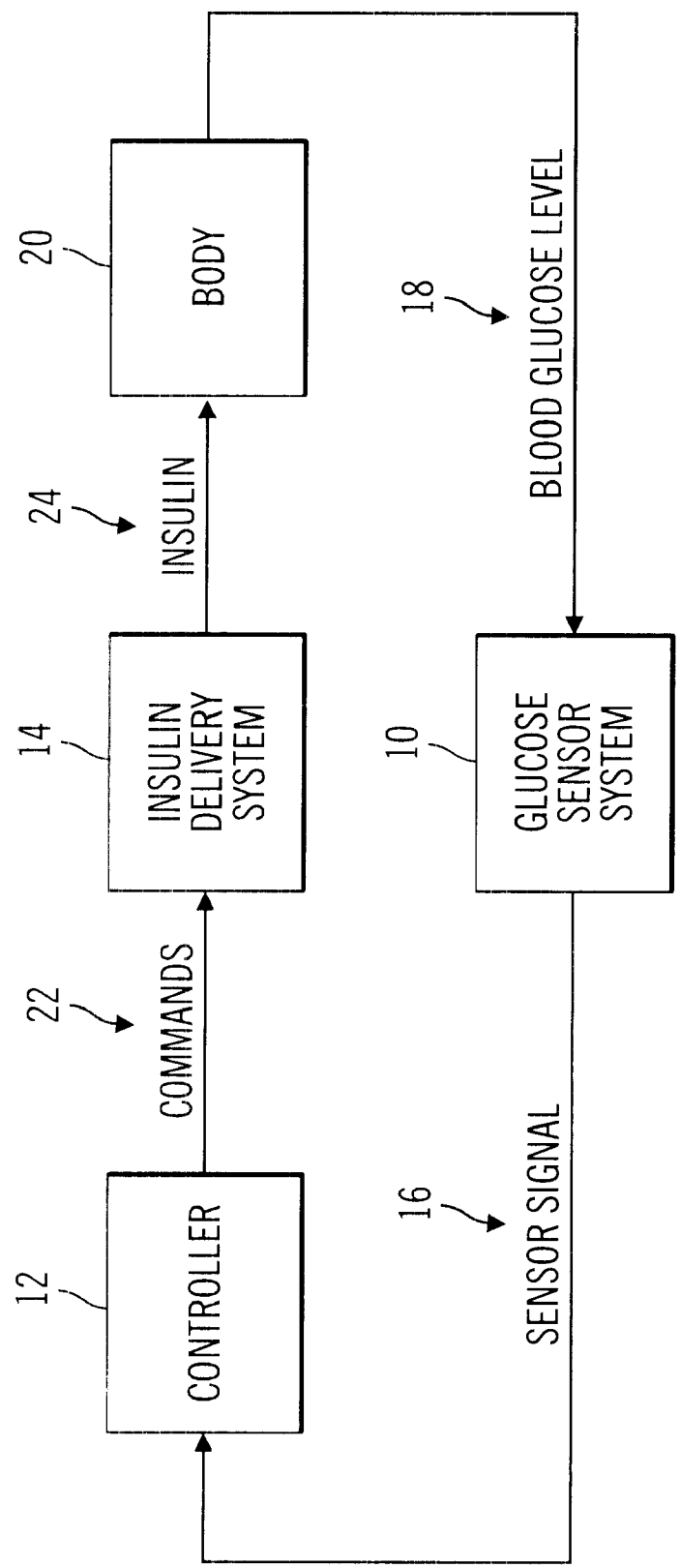
FIG. 1 is a block diagram of a closed loop glucose control system in accordance with an embodiment of the present invention.

As shown in the drawings for purposes of illustration, the invention is embodied in a closed loop infusion system for regulating the rate of fluid infusion into a body of a user based on feedback from an analyte concentration measurement taken from the body. In particular embodiments, the invention is embodied in a control system for regulating the rate of insulin infusion into the body of a user based on a glucose concentration measurement taken from the body. In preferred embodiments, the system is designed to model a pancreatic beta cell (β-cell). In other words, the system controls an infusion device to release insulin into a body of a user in a similar concentration profile as would be created by fully functioning human β-cells when responding to changes in blood glucose concentrations in the body.

Thus, the system simulates the body's natural insulin response to blood glucose levels and not only makes efficient use of insulin, but also accounts for other bodily functions as well since insulin has both metabolic and mitogenic effects. However, the algorithms must model the β-cells closely, since algorithms that are designed to minimize glucose excursions in the body, without regard for how much insulin is delivered, may cause excessive weight gain, hypertension, and atherosclerosis. In preferred embodiments of the present invention, the system is intended to emulate the in vivo insulin secretion pattern and to adjust this pattern consistent with the in vivo β-cell adaptation experienced by normal healthy individuals. The in vivo β-cell response in subjects with normal glucose tolerance (NGT), with widely varying insulin sensitivity ($S_1$), is the optimal insulin response for the maintenance of glucose homeostasis.

Preferred embodiments include a glucose sensor system 10, a controller 12 and an insulin delivery system 14, as shown in FIG. 1. The glucose sensor system 10 generates a sensor signal 16 representative of blood glucose levels 18 in the body 20, and provides the sensor signal 16 to the controller 12. The controller 12 receives the sensor signal 16 and generates commands 22 that are communicated to the insulin delivery system 14. The insulin delivery system 14 receives the commands 22 and infuses insulin 24 into the body 20 in response to the commands 22.

Generally, the glucose sensor system 10 includes a glucose sensor, sensor electrical components to provide power to the sensor and generate the sensor signal 16, a sensor communication system to carry the sensor signal 16 to the controller 12, and a sensor system housing for the electrical components and the sensor communication system.

Typically, the controller 12 includes controller electrical components and software to generate commands for the insulin delivery system 14 based on the sensor signal 16, and a controller communication system to receive the sensor signal 16 and carry commands to the insulin delivery system 14.

Generally, the insulin delivery system 14 includes an infusion device and an infusion tube to infuse insulin 24 into the body 20. In particular embodiments, the infusion device includes infusion electrical components to activate an infusion motor according to the commands 22, an infusion communication system to receive the commands 22 from the controller 12, and an infusion device housing to hold the infusion device.

In preferred embodiments, the controller 12 is housed in the infusion device housing and the infusion communication system is an electrical trace or a wire that carries the commands 22 from the controller 12 to the infusion device. In alternative embodiments, the controller 12 is housed in the sensor system housing and the sensor communication system is an electrical trace or a wire that carries the sensor signal 16 from the sensor electrical components to the controller electrical components. In other alternative embodiments, the controller 12 has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces.

System Overview

Figure 2:
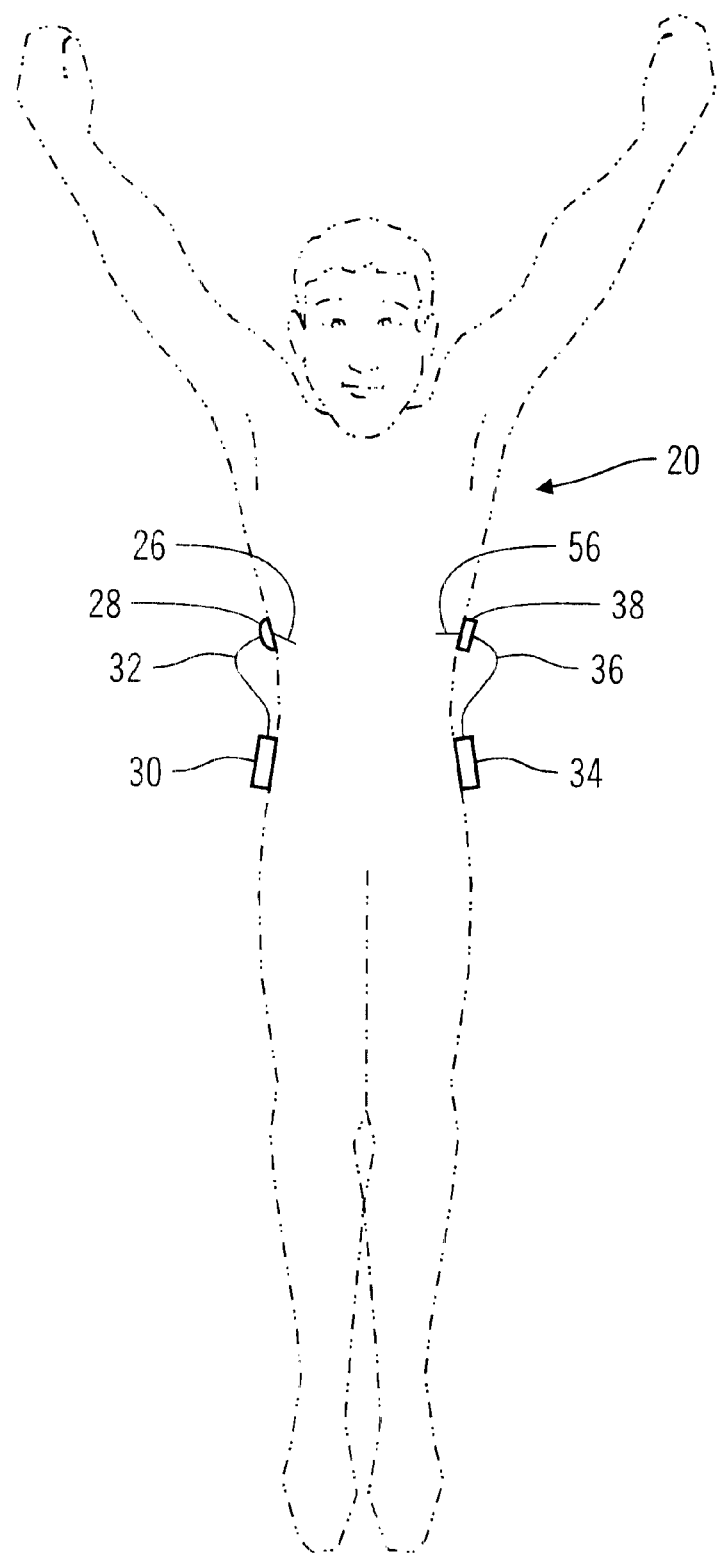
FIG. 2 is a front view of closed loop hardware located on a body in accordance with an embodiment of the present invention.
Figure 3:
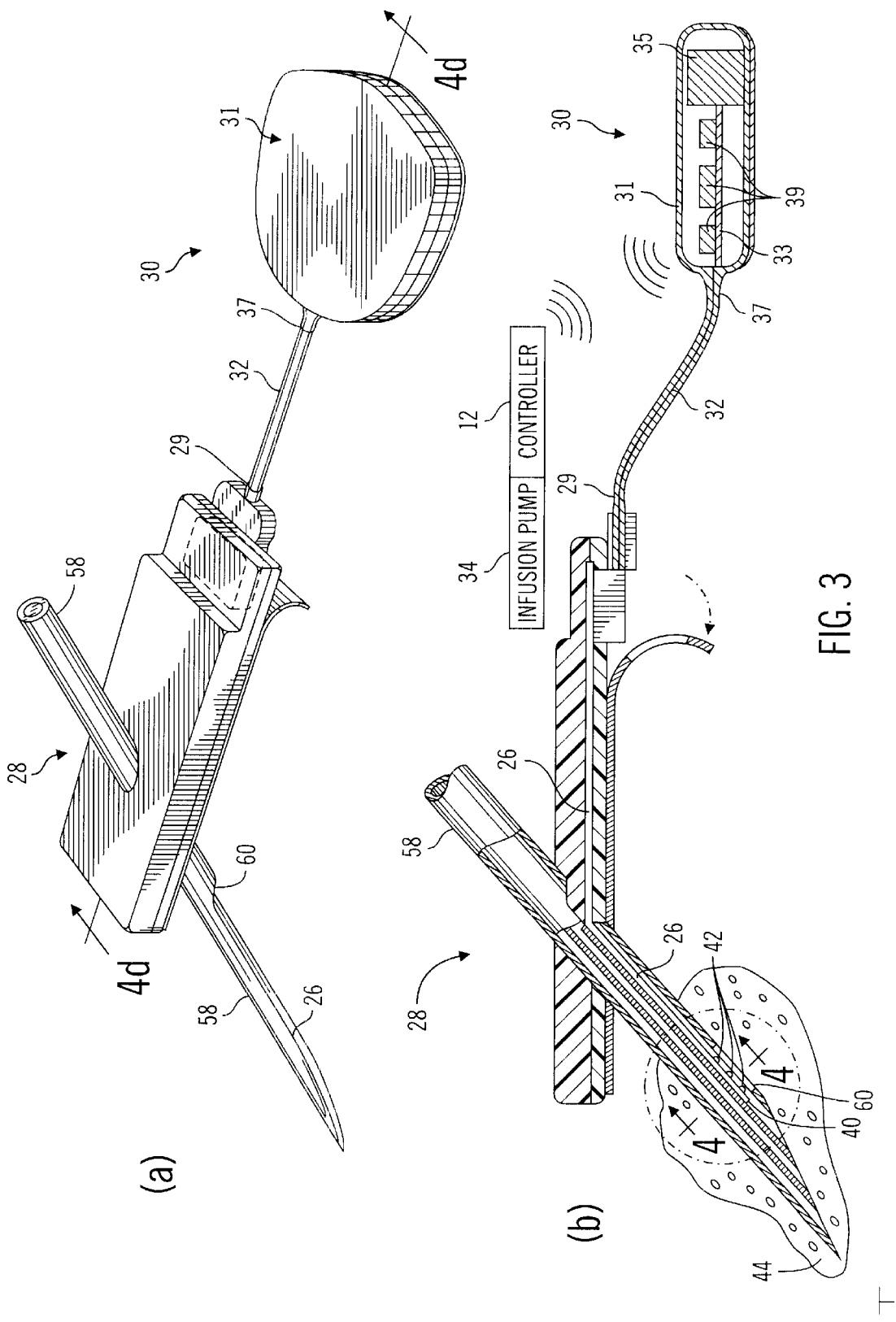
FIG. 3(a) is a perspective view of a glucose sensor system for use in an embodiment of the present invention.
FIG. 3(b) is a side cross-sectional view of the glucose sensor system of FIG. 3(a).
FIG. 3(c) is a perspective view of a sensor set of the glucose sensor system of FIG. 3(a) for use in an embodiment of the present invention.
FIG. 3(d) is a side cross-sectional view of the sensor set of FIG. 3(c).

Preferred embodiments of the invention include a sensor 26, a sensor set 28, a telemetered characteristic monitor 30, a sensor cable 32, an infusion device 34, an infusion tube 36, and an infusion set 38, all worn on the body 20 of a user, as shown in FIG. 2. The telemetered characteristic monitor 30 includes a monitor housing 31 that supports a printed circuit board 33, batteries 35, antenna (not shown), and a sensor cable connector (not shown), as seen in FIG. 3(a) and 3(b). A sensing end 40 of the sensor 26 has exposed electrodes 42 and is inserted through skin 46 into a subcutaneous tissue 44 of a user's body 20, as shown in FIG. 3 (d) and 4. The electrodes 42 are in contact with interstitial fluid (ISF) that is present throughout the subcutaneous tissue 44. The sensor 26 is held in place by the sensor set 28, which is adhesively secured to the user's skin 46, as shown in FIGS. 3(c) and 3(d). The sensor set 28 provides for a connector end 27 of the sensor 26 to connect to a first end 29 of the sensor cable 32. A second end 37 of the sensor cable 32 connects to the monitor housing 31. The batteries 35 included in the monitor housing 31 provide power for the sensor 26 and electrical components 39 on the printed circuit board 33. The electrical components 39 sample the sensor signal 16 and store digital sensor values (Dsig) in a memory and then periodically transmit the digital sensor values Dsig from the memory to the controller 12, which is included in the infusion device.

Figure 5:
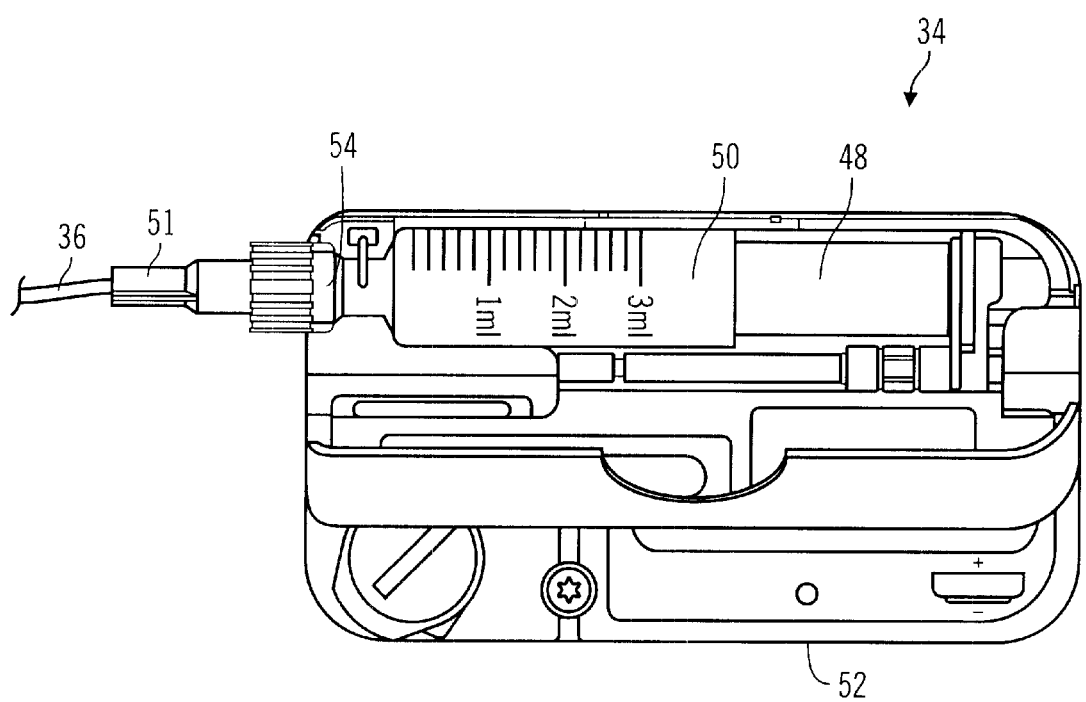
FIG. 5 is a top view of an infusion device with a reservoir door in the open position, for use in an embodiment of the present invention.
Figure 6:
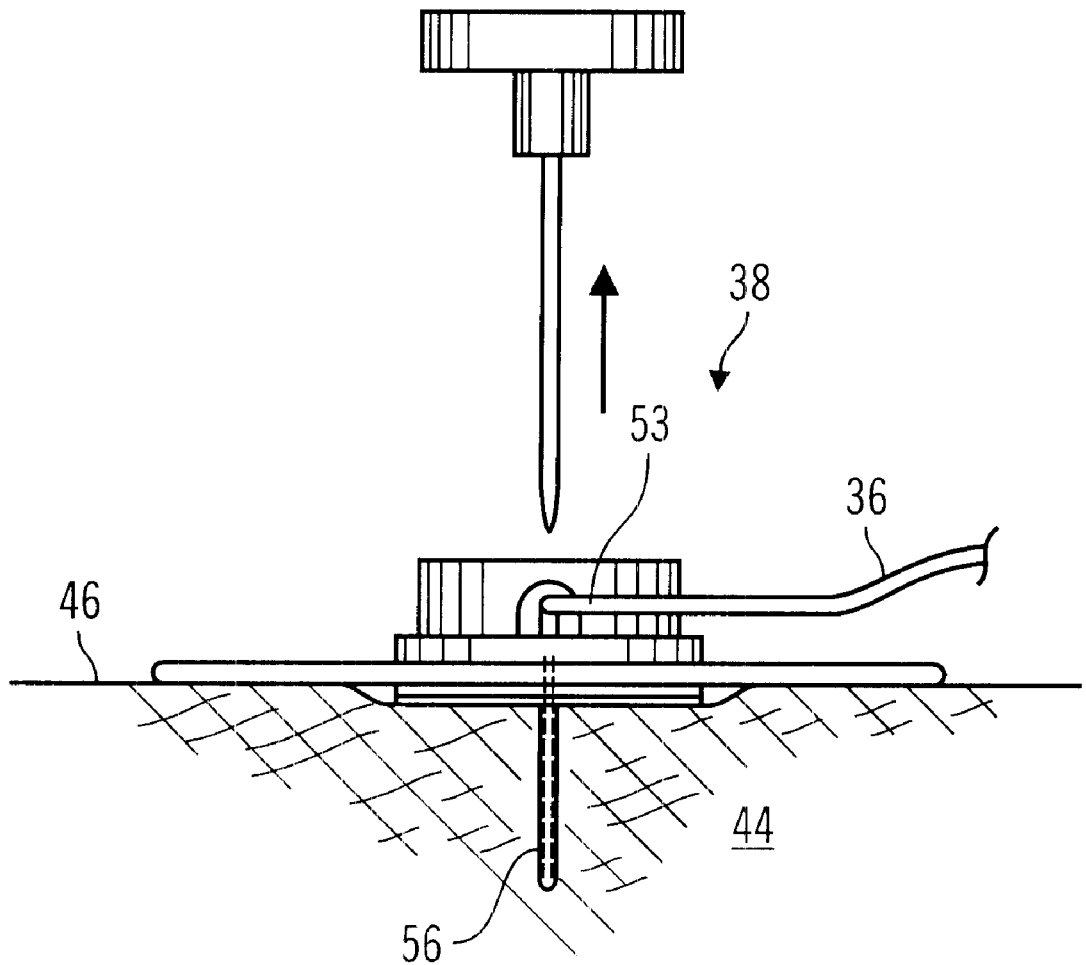
FIG. 6 is a side view of an infusion set with the insertion needle pulled out, for use in an embodiment of the present invention.

The controller 12 processes the digital sensor values Dsig and generates commands 22 for the infusion device 34. Preferably, the infusion device 34 responds to the commands 22 and actuates a plunger 48 that forces insulin 24 out of a reservoir 50 located inside the infusion device 34, as shown in FIG. 5. In particular embodiments, a connector tip 54 of the reservoir 50 extends through the infusion device housing 52 and a first end 51 of the infusion tube 36 is attached to the connector tip 54. A second end 53 of the infusion tube 36 connects to the infusion set 38. Insulin 24 is forced through the infusion tube 36 into the infusion set 38 and into the body 16. The infusion set 38 is adhesively attached to the user's skin 46, as shown in FIG. 6. As part of the infusion set 38, a cannula 56 extends through the skin 46 and terminates in the subcutaneous tissue 44 completing fluid communication between the reservoir 50 and the subcutaneous tissue 44 of the user's body 16.

In alternative embodiments, the system components may be combined in a smaller or greater number of devices and/or the functions of each device may be allocated differently to suit the needs of the user.

Controller

Once the hardware for a closed loop system is configured, such as in the preferred embodiments described above, the affects of the hardware on a human body are determined by the controller. In preferred embodiments, the controller 12 is designed to model a pancreatic beta cell (β-cell). In other words, the controller 12 commands the infusion device 34 to release insulin 24 into the body 20 at a rate that causes the insulin concentration in the blood to follow a similar concentration profile as would be caused by fully functioning human β-cells responding to blood glucose concentrations in the body 20.

A controller that simulates the body's natural insulin response to blood glucose levels not only makes efficient use of insulin but also accounts for other bodily functions as well since insulin has both metabolic and mitogenic effects. Controller algorithms that are designed to minimize glucose excursions in the body without regard for how much insulin is delivered may cause excessive weight gain, hypertension, and atherosclerosis. In preferred embodiments, of the present invention, the controller 22 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity ($S_I$), is the optimal insulin response for the maintenance of glucose homeostasis.

The β-cell and PID Control

Generally, the in vivo β-cell response to changes in glucose is characterized by "first" and "second" phase insulin responses. This biphasic insulin response is clearly seen during hyperglycemic clamps applied to NGT subjects, as shown in FIG. 23(b). During a hyperglycemic clamp the glucose level is rapidly increased from a basal level $G_B$ to a new higher level $G_C$ and then held constant at the higher-level $G_C$ as shown in FIG. 23(a). The magnitude of the increase in glucose (ΔG) affects the insulin response. Four insulin response curves are shown for four different glucose clamp levels in FIG. 23(b).

The biphasic insulin response of a β-cell can be modeled using components of a proportional, plus integral, plus derivative (PID) controller. A PID controller is selected since PID algorithms are stable for a wide variety of non-medical dynamic systems, and PID algorithms have been found to be stable over widely varying disturbances and changes in system dynamics.

Figure 24:
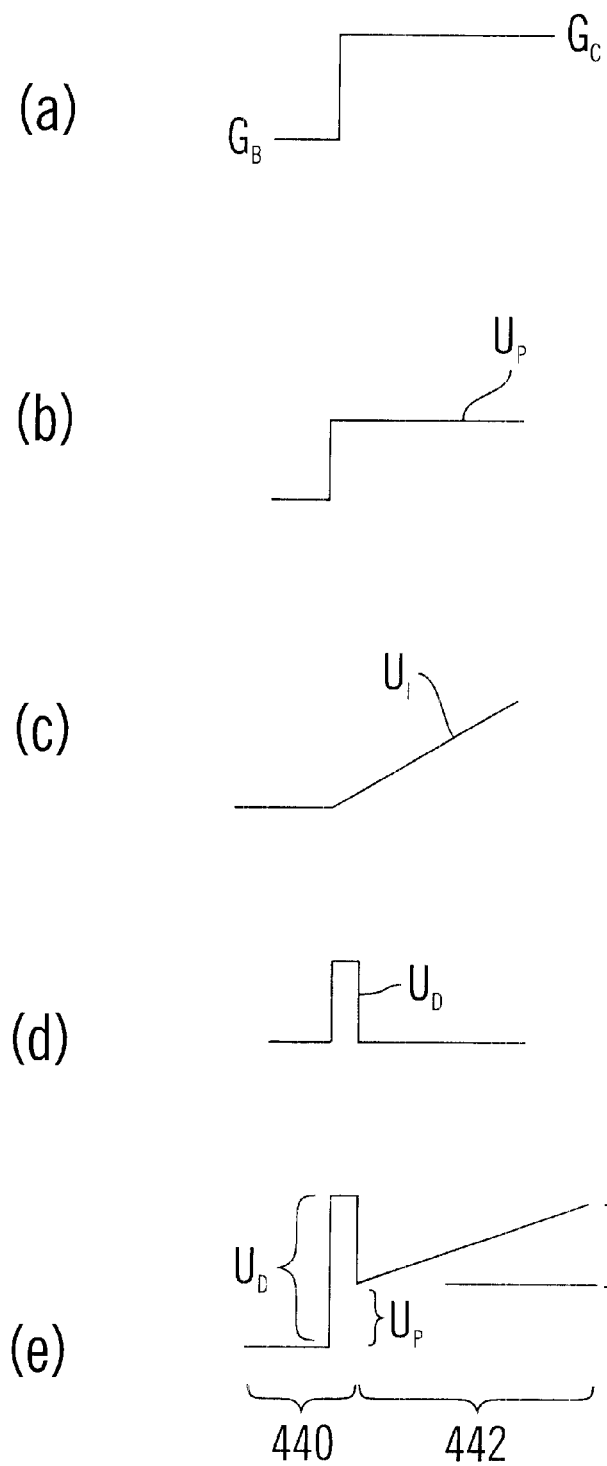
FIG. 24(a) is a diagram of a glucose clamp.
FIG. 24(b) is a diagram of a proportional insulin response to the glucose clamp of FIG. 24 (a) in accordance with an embodiment of the present invention.
FIG. 24(c) is a diagram of an integral insulin response to the glucose clamp of FIG. 24(a) in accordance with an embodiment of the present invention.
FIG. 24(d) is a diagram of a derivative insulin response to the glucose clamp of FIG. 24 (a) in accordance with an embodiment of the present invention.
FIG. 24(e) is a diagram of a combined proportional, integral, and derivative insulin response to the glucose clamp of FIG. 24(a) in accordance with an embodiment of the present invention.

The insulin response of β-cells during a hyperglycemic clamp is diagrammed in FIGS. 24 (a–e) using the components of a PID controller to model the β-cell. A proportional component $U_P$ and a derivative component $U_D$ of the PID controller may be combined to represent a first phase insulin response 440, which lasts several minutes. A integral component $U_I$ of the PID controller represents a second phase insulin response 442, which is a steady increase in insulin release under hyperglycemic clamp conditions. The magnitude of each component's contribution to the insulin response is described by the following equations:

$$\text{Proportional Component Response: } U_P = K_P(G - G_B),$$

$$\text{Integral Component Response: } U_I = K_1 \int_{t_0}^{t}(G - G_B)dt + I_B, \text{ and}$$

$$\text{Derivative Component Response: } U_D = K_D \frac{dG}{dt},$$

Where $U_P$ is the proportional component of the command sent to the insulin delivery system, $U_I$ is the integral component of the command sent to the insulin delivery system, $U_D$ is the derivative component of the command sent to the insulin delivery system, $K_P$ is a proportional gain coefficient, $K_I$ is a integral gain coefficient, $K_D$ is a derivative gain coefficient.

G is a present blood glucose level, $G_B$ is a desired basal glucose level, t is the time that has passed since the last calibration, $t_0$ is the time of the last calibration, and $I_B$ is a basal insulin concentration at $t_0$.

The combination of the PID components that model the two phases of insulin response by a β-cell is shown in FIG. 24(e) as it responds to the hyperglycemic clamp of FIG. 24(a). FIG. 24(e) shows that the magnitude of the first phase response 440 is driven by the derivative and proportional gains, $K_D$ and $K_P$. And the magnitude of the second phase response 442 is driven by the integral gain $K_I$.

An acute insulin response is essential for preventing wide postprandial glycemic excursions. Generally, an early insulin response to a sudden increase in glucose level results in less total insulin being needed to bring the glucose level back to a desired basal glucose level. This is because the infusion of insulin increases the percentage of glucose that is taken up by the body. Infusing a large amount of insulin to increase the percentage of glucose uptake while the glucose concentration is high results in an efficient use of insulin. Conversely, infusing a large amount of insulin while the glucose concentration is low results in using a large amount of insulin to remove a relatively small amount of glucose. In other words, a larger percentage of a big number is more than a larger percentage of a small number. The infusion of less total insulin helps to avoid development of insulin resistance in the user. As well, first-phase insulin is thought to result in an early suppression of hepatic glucose output.

Insulin sensitivity is not fixed and can change dramatically in a body depending on the amount of exercise by the body. In one study, for example, insulin responses in highly exercise-trained individuals (individuals who trained more than 5 days a week) were compared to the insulin responses in subjects with normal glucose tolerance (NGT) during a hyperglycemic clamp. The insulin response in exercise-trained individuals 444 was about ½ of the insulin response of the NGT subjects 446, as shown in FIG. 25(*a*). But the glucose uptake rate for each of the individuals (exercise-trained 448 or normal 450) was virtually identical, as shown in FIG. 25(*b*). Thus, it can be speculated that the exercise-trained individuals have twice the insulin sensitivity and half of the insulin response leading to the same glucose uptake as the NGT individuals. Not only is the first phase insulin response 440 reduced due to the effects of exercise, but the second phase insulin response 442 has also been shown to adjust to insulin sensitivity, as can be seen in FIG. 25(*a*).

Figure 26:
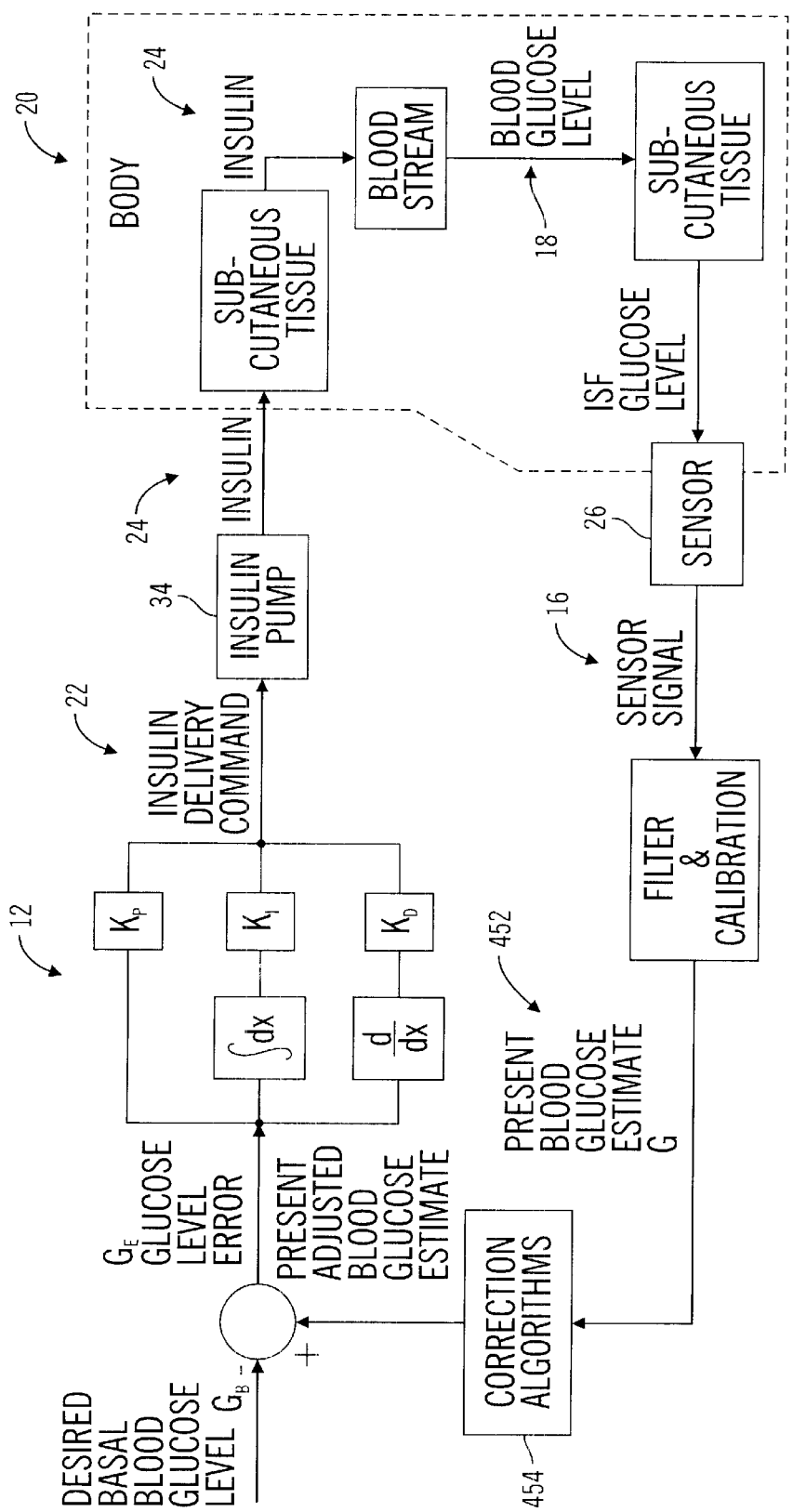
FIG. 26 is a block diagram of a closed loop system to control blood glucose levels through insulin infusion based on glucose level feedback in accordance with an embodiment of the present invention.

In preferred embodiments, a closed loop control system may be used for delivering insulin to a body to compensate for β-cells that perform inadequately. There is a desired basal blood glucose level $G_B$ for each body. The difference between the desired basal blood glucose level $G_B$ and an estimate of the present blood glucose level G is the glucose level error $G_E$ that must be corrected. The glucose level error $G_E$ is provided as an input to the controller 12, as shown in FIG. 26.

If the glucose level error $G_E$ is positive (meaning that the present estimate of the blood glucose level G is higher than the desired basal blood glucose level $G_B$) then the controller 12 generates an insulin delivery command 22 to drive the infusion device 34 to provide insulin 24 to the body 20. In terms of the control loop, glucose is considered to be positive, and therefore insulin is negative. The sensor 26 senses the ISF glucose level and generates a sensor signal 16. The sensor signal 16 is filtered and calibrated to create an estimate of the present blood glucose level 452. In particular embodiments, the estimate of the present blood glucose level G is adjusted with correction algorithms 454 before it is compared to the desired basal blood glucose level $G_B$ to calculate a new glucose level error $G_E$ to start the loop again.

If the glucose level error $G_E$ is negative (meaning that the present estimate of the blood glucose level is lower than the desired basal blood glucose level $G_B$) then the controller 12 reduces or stops the insulin delivery depending on whether the integral component response of the glucose error $G_E$ is still positive.

If the glucose level error $G_E$ is zero, (meaning that the present estimate of the blood glucose level is equal to the desired basal blood glucose level $G_B$) then the controller 12 may or may not issue commands to infuse insulin depending on the derivative component (whether the glucose level is raising or falling) and the integral component (how long and by how much glucose level has been above or below the basal blood glucose level $G_B$).

Figure 27:
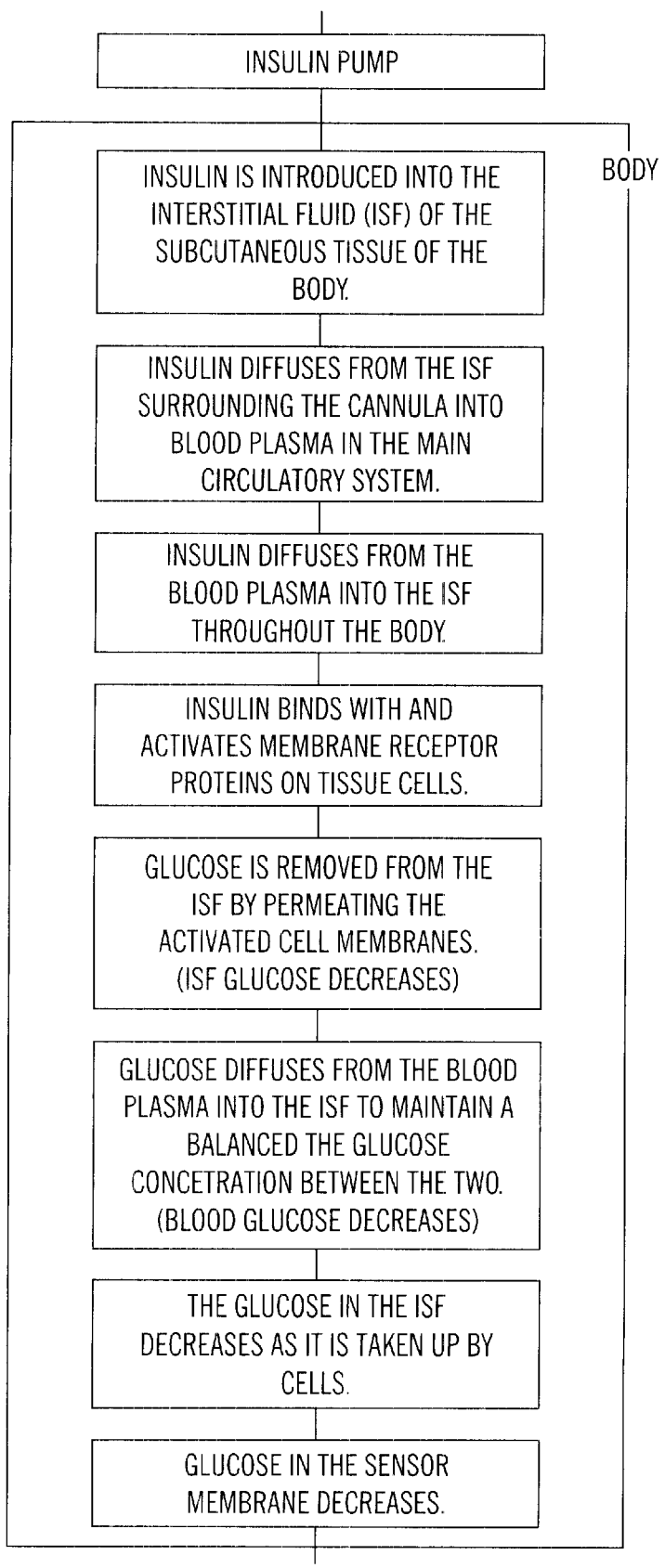
FIG. 27 is a detailed block diagram of the portion of the control loop of FIG. 26 that is in the body in accordance with an embodiment of the present invention.

To more clearly understand the effects that the body has on the control loop, a more detailed description of the physiological affects that insulin has on the glucose concentration in the interstitial fluid (ISF) is needed. In preferred embodiments, the infusion device 34 delivers insulin through the cannula 56 of the infusion set 38 into the ISF of the subcutaneous tissue 44 of the body 20. And the insulin 24 diffuses from the local ISF surrounding the cannula into the blood plasma and then spreads throughout the body 20 in the main circulatory system, as described in the block diagram of FIG. 27. The insulin then diffuses from the blood plasma into the interstitial fluid ISF substantially through out the entire body. The insulin 24 binds with and activates membrane receptor proteins on cells of body tissues. This facilitates glucose permeation into the activated cells. In this way, the tissues of the body 20 take up the glucose from the ISF. As the ISF glucose level decreases, glucose diffuses from the blood plasma into the ISF to maintain glucose concentration equilibrium. Finally, the glucose in the ISF permeates the sensor membrane and affects the sensor signal 16.

In addition, insulin has direct and indirect affects on liver glucose production. Increased insulin concentration decreases liver glucose production. Therefore, acute and immediate insulin response not only helps the body to efficiently take up glucose but also substantially stops the liver from adding to the glucose in the blood stream. In alternative embodiments, insulin is delivered more directly into the blood stream instead of into the interstitial fluid, such as delivery into veins, arteries, the peritoneal cavity, or the like. And therefore, any time delay associated with moving the insulin from the interstitial fluid into the blood plasma is diminished. In other alternative embodiments, the glucose sensor is in contact with blood or body fluids other than interstitial fluid, or the glucose sensor is outside of the body and measures glucose through a non-invasive means. The embodiments that use alternative glucose sensors may have shorter or longer delays between the blood glucose level and the measured blood glucose level.

Selecting Controller Gains

In preferred embodiments, the controller gains $K_P$, $K_I$, and $K_D$, are selected so that the commands from the controller 12 cause the infusion device 34 to release insulin 24 into the body 20 at a rate, that causes the insulin concentration in the blood to follow a similar concentration profile, as would be caused by fully functioning human β-cells responding to blood glucose concentrations in the body. In preferred embodiments, the gains may be selected by observing the insulin response of several normal glucose tolerant (NGT) individuals, with healthy normally functioning β-cells. The first step in determining a set of controller gains is to take periodic measurements of blood glucose and blood insulin concentrations from the group of NGT individuals. Second, each individual in the group is subjected to a hyperglycemic clamp, while continuing to periodically measure and record the blood glucose and blood insulin concentrations. Third, a least squares curve fit is applied to the recorded blood insulin concentrations measured over time for each individual. The result is a set of curves representing the insulin responses to the hyperglycemic clamp for each individual of the group. Fourth, the curves are used to calculate the controller gains $K_P$, $K_I$, and $K_D$, for each individual. And finally, the proportional gains from each of the individuals are averaged together to obtain an average proportional gain, $K_P$, to be used in a controller 12. Similarly, the integral gains, $K_I$, and the derivative gains, $K_D$, are averaged to obtain an average integral gain, $K_I$, and an average derivative gain, $K_D$, for the controller 12.

Alternatively, other statistical values may be used instead of averages such as, maximums, minimums, the high or low one, two or three sigma standard deviation values, or the like. The gains calculated for various individuals in a group may be filtered to remove anomalous data points before statistically calculating the gains to be used in a controller.

Figure 28:
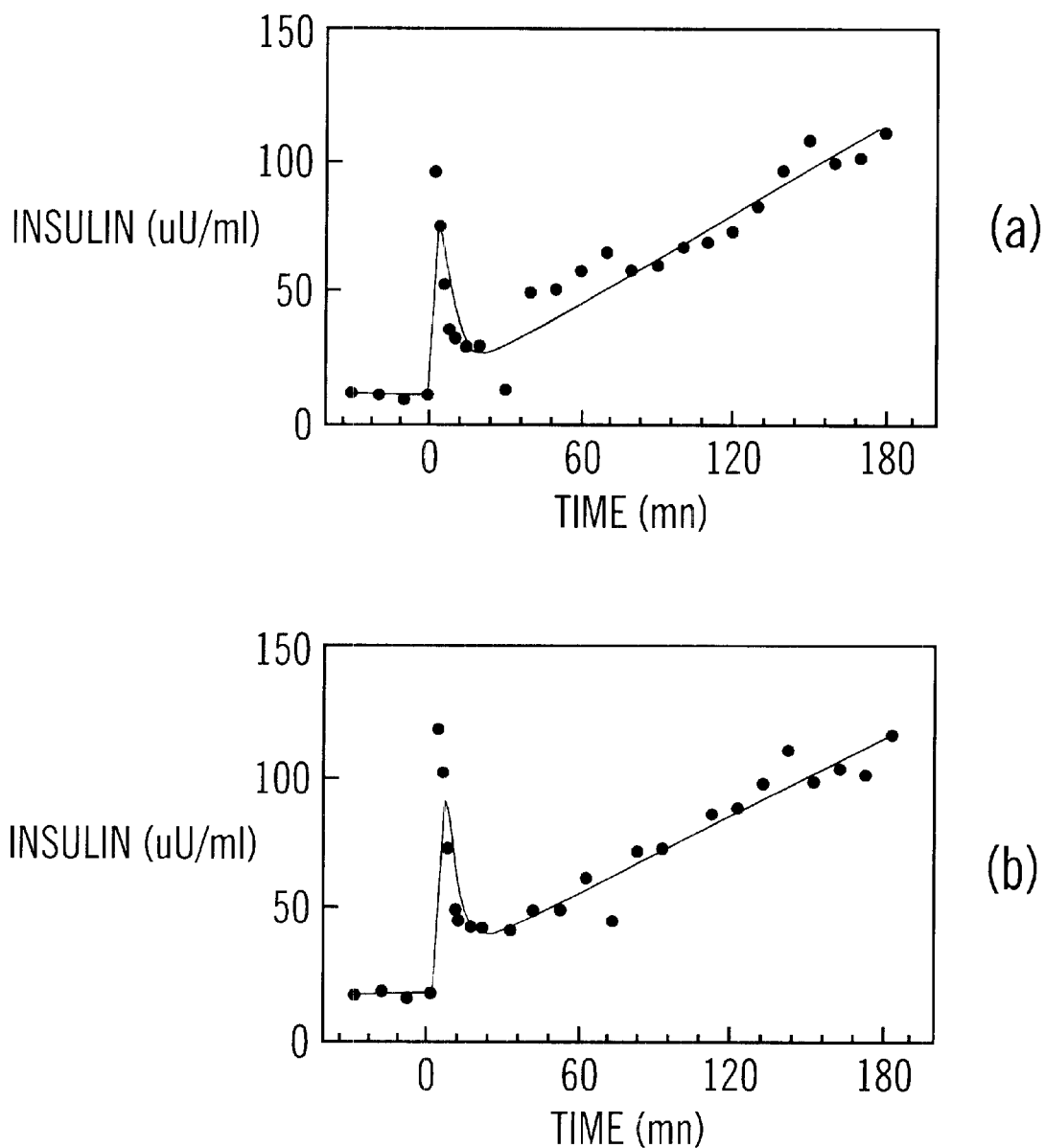
FIGS. 28 (a and b) are plots of measured insulin responses of two different normal glucose tolerant (NGT) individuals to a glucose clamp for use with an embodiment of the present invention.

In an example, a least squares curve-fitting method is used to generate representative insulin response curves from two fasted individuals in a group, as shown in FIGS. 28 (a and b). Then the controller gains were calculated from the insulin response curves of the two representative individuals and are shown in Table 1. When calculating the controller gains, the insulin clearance rate (k), was assumed to be 10 (ml of insulin) /min/(kg. of body weight). The insulin clearance rate k is the rate that insulin is taken out of the blood stream in a body. Finally, the average value for each type of gain is calculated using the measurements from the group, as shown in Table 1.

TABLE 1

PID Controller Gains Calculated From The Insulin Response Curves Of Two NGT Individuals.

| Individuals | Proportional Gain, $K_P$ | Integral Gain, $K_I$ | Derivative Gain, $K_D$ |
|---|---|---|---|
| a | 0.000406 | 0.005650 | 0.052672 |
| b | 0.000723 | 0.003397 | 0.040403 |
| Average | 0.000564 | 0.004523 | 0.046537 |

The controller gains may be expressed in various units and/or may be modified by conversion factors depending on preferences for British or S. I. Units, floating-point or integer software implementation, the software memory available, or the like. The set of units for the controller gains in Table 1 is:

$K_P$: (mU of insulin)/min/(Kg of body weight) per (mg of glucose)/(dl of plasma);

$K_I$: (mU of insulin)/min/(Kg of body weight) per (mg of glucose)/(dl of plasma) min.; and $K_D$: (mU of insulin)/min/(Kg of body weight) per (mg of glucose)/(dl of plasma)/min.

In alternative embodiments, other curve fitting methods are used to generate the insulin response curves from the measurements of blood insulin concentrations.

An estimate of an insulin clearance rate (k), the individual's body weight (W), and the insulin sensitivity $S_I$ are needed to calculate the controller gains from the insulin response curves for each NGT individual. The insulin clearance rate (k) is generally proportional to body weight and is well documented in literature. The individual's insulin sensitivity $S_I$ may be measured using an intravenous glucose tolerance test, a hyperinsulinemic clamp, or in the case of a diabetic, comparing the individual's daily insulin requirement to their daily carbohydrate intake.

In particular embodiments, two parameters, the insulin sensitivity $S_I$ and the insulin clearance rate k, are measured for each individual. In other embodiments, the insulin clearance rate k is estimated from literature given the individual's body weight. In other particular embodiments, longer or shorter insulin clearance times are used. In still other embodiments, all of the parameters are estimated. In additional embodiments, one or more parameters are measured, while at least one parameter is estimated from literature.

In other alternative embodiments, the controller gains are calculated using a group of individuals with similar body types. For example, the insulin response to a hyperglycemic clamp may be measured for several tall, thin, NGT, males in order to calculate the controller insulin response gains for each individual in the group. Then the gains are statistically combined to generate a set of representative controller gains for tall, thin, NGT, males. The same could be done for other groups such as, but not limited to, short, heavy, NGT, females; medium height, medium weight, highly exercised trained, females; average height and weight 10 year olds; or the like. Then the controller gains are selected for each individual user based on the group that best represents them. In further alternative embodiments, controller gains are uniquely selected for each individual user. In particular embodiments, the controller gains for a user are selected based on measurements of insulin sensitivity, insulin clearing time, insulin appearance time, insulin concentration, body weight, body fat percentage, body metabolism, or other body characteristics such as pregnancy, age, heart conditions, or the like.

Figure 23:
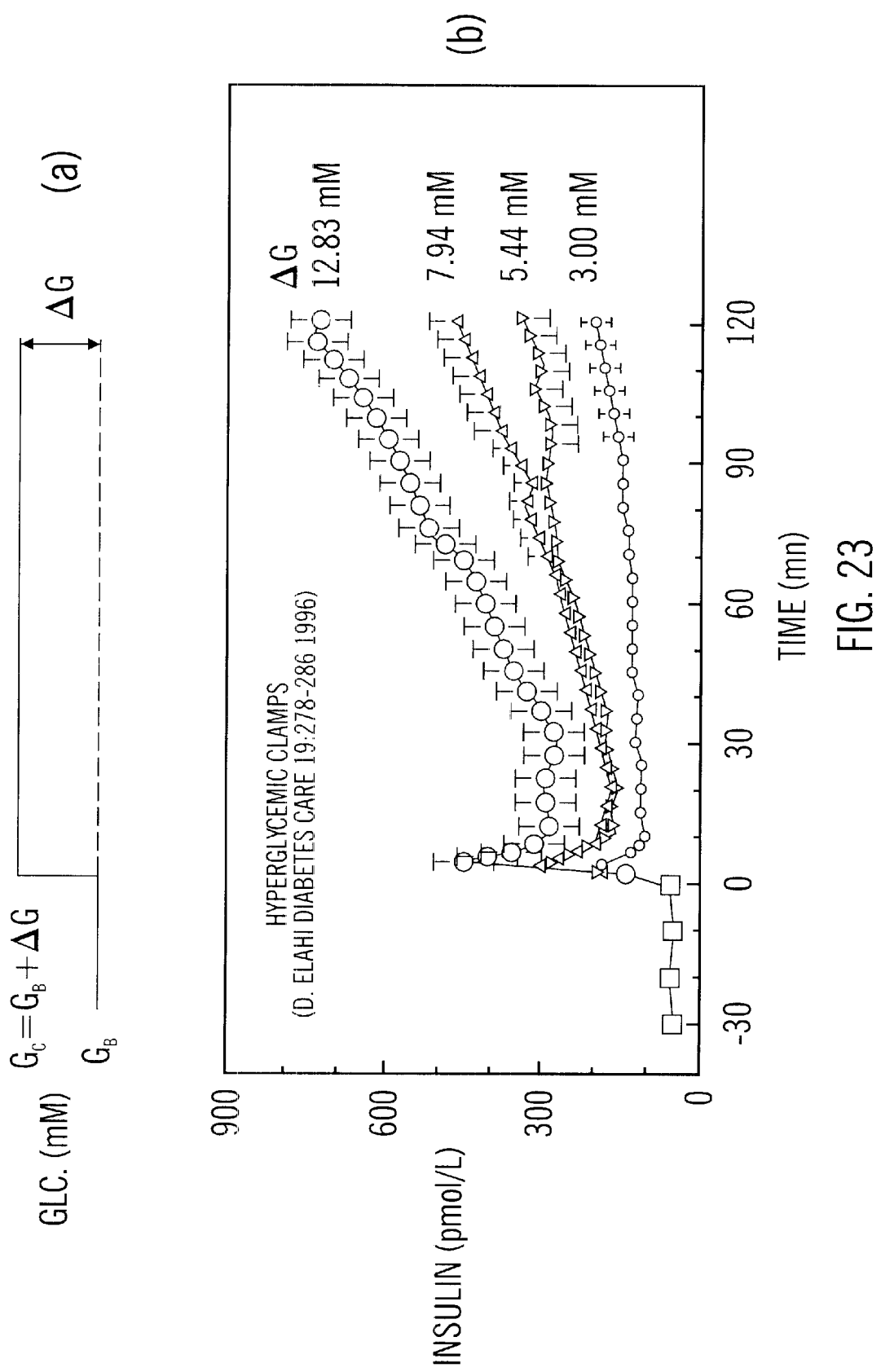
FIG. 23(a) is a diagram of a glucose clamp (glucose level with respect to time).
FIG. 23(b) is a plot of insulin concentration in a normal glucose tolerant (NGT) individual in response to various magnitudes of glucose clamps of FIG. 23(a).

In other alternative embodiments, the controller gains are estimated as a function of a user's body weight W and insulin sensitivity $S_I$. A series of observations are used to justify this method. The first observation is that the controller gains are proportional to each other. In other words, small changes in glucose concentration cause a small derivative response $U_D$, a small proportional response $U_P$ and a small integral response $U_I$. And larger changes in glucose concentration cause a proportionally larger derivative response $U_D$, a proportionally larger proportional Up response and a proportionally larger integral response $U_I$, as shown in FIG. 23($b$). Changes in the glucose concentration proportionally affect all three components of the controller response $U_{PID}$. The second observation is that the first phase insulin response ($\phi1$) is proportional to the derivative gain $K_D$. And the third observation is that two constants may be readily obtained form information in published literature or may be measured from a cross-section of the general population. The two constants are the insulin clearance rate (k) for a human given a body weight and the disposition index (DI) for a human given a change in glucose concentration.

While there are multiple sources for the information needed to calculate the insulin clearance rate k, one source is the article "Insulin clearance during hypoglycemia in patients with insulin-dependent diabetes mellitus", written by Kollind M et al., published in *Hurm Metab Res*, Jul;23, 1991(7):333-5. The insulin clearance rate k is obtained from the insulin infused divided by the steady state plasma insulin concentration. An insulin clearance constant $A_k$, which is independent of an individual's body weight, may be obtained by dividing the insulin clearance rate k (measured from a particular individual) by the individual's body weight. The insulin clearance constant $A_k$ is generally the same for all humans, except under extenuating circumstances such as after an individual has contracted HIV, other metabolic affecting diseases, or the like.

The disposition index (DI) for a human given a change in glucose concentration is available from information presented in the article "Quantification of the relationship between insulin sensitivity and beta-cell function in human subjects. Evidence for a hyperbolic function", written by Khan SE et al., published in *Diabetes*, Nov;1993 42(11): 1663–72.

Both, the disposition index DI and the insulin clearance rate k may be measured directly from tests. The disposition index DI may be calculated given the first phase insulin response measured form a glucose clamp test and the individual's insulin sensitivity measured from an insulin sensitivity test. The insulin clearance rate k may be measured from an insulin clearance test. The glucose clamp test and the insulin clearance test are described in the above-mentioned articles and are well known in the art. The insulin sensitivity $S_I$ may be measured using an intravenous glucose tolerance test or a hyperinsulinemic clamp test.

Given these observations, then the following parameters may be measured from an NGT individual's insulin response to a glucose clamp: a desired first phase insulin response $\phi 1$, the ratio of $K_D$ to $K_P$, and the ratio of $K_D$ to K. Then the derivative gain $K_D$ may be calculated from the first phase insulin response $\phi 1$ using the constants k and DI. And finally $K_P$ and $K_I$ may be calculated using the ratios of $K_D$ to $K_P$ and $K_D$ to $K_I$.

The first phase insulin response $\phi 1$ may be observed in a NGT individual as the area under the insulin response curve during approximately the first 10 minutes of a glucose clamp. The increase in the glucose concentration during the glucose clamp is $$\Delta G = (G - G_B),$$

where G is equal to Gc, the glucose concentration during the clamp, and $G_B$ is the basal glucose concentration before the clamp.
The importance of the first phase insulin response $\phi 1$ has been emphasized by studies indicating that, in subjects with normal glucose tolerance (NGT), the product of first phase insulin response $\phi 1$ and insulin sensitivity ($S_I$) is a constant known as the disposition index, $$DI = \phi 1 S_I.$$

Therefore, $$\phi 1 = \frac{DI}{S_I}.$$

For a different $\Delta G$ there is a different $\phi 1$ and therefore a different DI. But, the ratio DI/$\Delta G$ is substantially constant even for different individuals with different insulin sensitivities.

The insulin sensitivity $S_I$ is defined as the percentage of the glucose concentration that the body tissues will take up for a given amount of insulin. The β-cell naturally adapts to changes in insulin sensitivity by adjusting the amount of insulin it secretes during the first phase insulin response $\phi 1$. This suggests that the body naturally seeks an optimal level of glucose tolerance. A controller that mimics this characteristic of the β-cell more accurately simulates the body's natural insulin response.

The instantaneous insulin response (RI) may be calculated given the insulin clearance rate (k) and the first phase insulin response $\phi 1$, $$R_I = k\phi 1$$

The insulin clearance rate k is proportional to body weight (W), therefore substituting a proportional constant $A_k$ and the user's body weight W for k and replacing $\phi 1$ with the ratio of DI over $S_I$ yields the following equation:

$$R_I = A_k W \frac{DI}{S_I}.$$

The instantaneous insulin response $R_I$ may also be expressed as the product of the derivative gain $K_D$ and the change in glucose concentration $\Delta G$, $$R_I = K_D \Delta G.$$

Setting the two equations for $R_I$ equal to each other and solving for $K_D$ yields, $$K_D = \frac{W}{S_I} \frac{A_k^{25} DI}{\Delta G}.$$

As mentioned above, DI/$\Delta G$ and $A_k$ are constants available or calculated from data in published literature. Combining the constants into a single constant, Q, $$Q = \frac{A_k DI}{\Delta G},$$

yields an equation for the derivative gain $K_D$ that is a function of the user's body weight W and the user's insulin sensitivity $S_I$, $$K_D = \frac{W}{S_I} Q.$$

Once the derivative gain $K_D$ is calculated, the proportional and integral gains are calculated using ratios. The ratio of $K_D/K_P$ can be set to the dominant time constant for insulin action, ranging from 10–60 minutes, but more typically 20–40 minutes and preferably 30 minutes. For example, calculating $K_P$ given $K_D$ using a time constant of 30 minutes, yields the following relationship:

$$\frac{K_D}{K_P} = 30 \Rightarrow K_P = \frac{K_D}{30}.$$

In a similar fashion, the ratio of $K_D/K_I$ can be set to the average ratio measured from a population of NGT individuals. And $K_I$ can be calculated from $K_D$.

In particular embodiments, the user enters their body weight W and insulin sensitivity $S_I$ into the device that contains the controller. Then the controller gains are automatically calculated and used by the controller. In alternative embodiments, an individual enters the user's body weight W and insulin sensitivity $S_I$ into a device and the device provides the information to the controller to calculate the gains.

Figure 29:
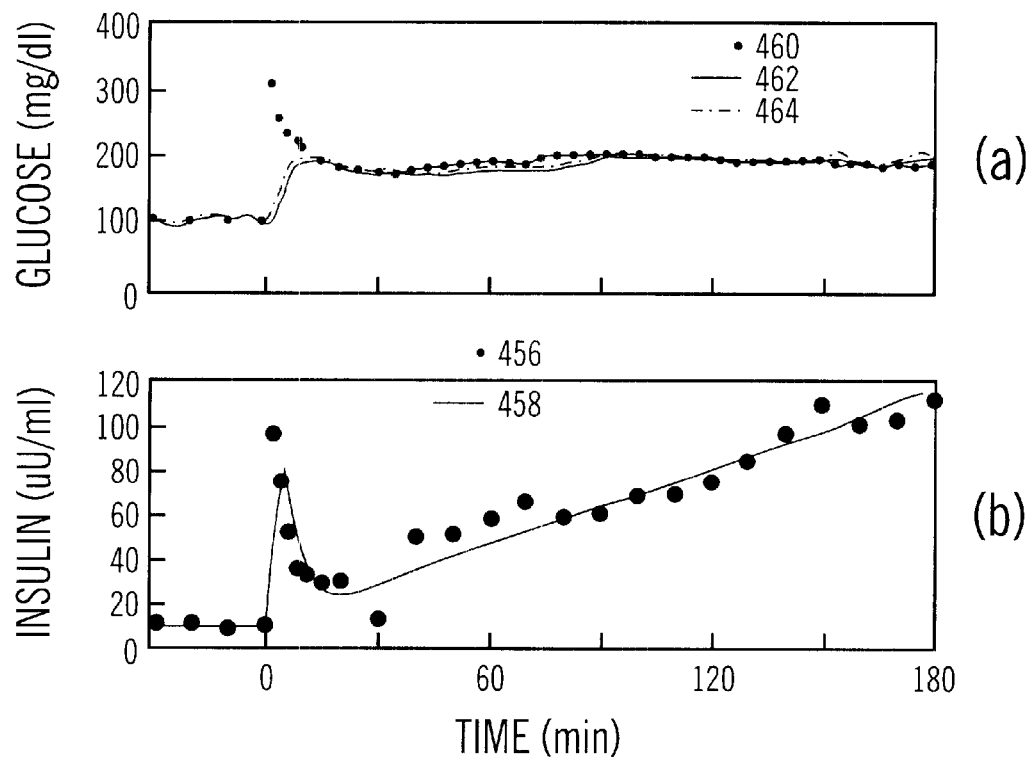
FIG. 29(a) is a plot of two different glucose sensor outputs compared to glucose meter readings during a glucose clamp in accordance with an embodiment of the present invention.
FIG. 29(b) is a plot of actual insulin concentration in blood compared to a controller commanded insulin concentration in response to the glucose clamp of FIG. 29(a) in accordance with an embodiment of the present invention.

A study was conducted to confirm that the insulin response for an individual could be reproduced using the glucose sensor as an input. In the study, glucose and insulin measurements were taken while a hyperglycemic clamp was applied to a NGT individual. The glucose level measurements, shown in FIG. 29(a), were used as the inputs to a mathematical model created to simulate a PID insulin response controller. The insulin dosing commanded by the controller in response to the glucose clamp very closely approximates the actual insulin appearance in the NGT individual, as shown in FIG. 29(b). The insulin concentration measured from periodic blood samples 456 taken from the individual during the test are represented by dots in FIG. 29(b). The output from the mathematical model simulating the insulin response commanded by the controller is shown as a solid line 458 in FIG. 29(b).

Three different devices were used to measure the individual's blood glucose during the study. Blood glucose meter readings 460 from periodic blood samples taken from the individual are represented by the dots in FIG. 29(*a*). Two MiniMed sensors (such as those described in the section entitled "sensor", below) were placed in the individual's subcutaneous tissue, and the sensor readings 462, 464 are shown as lines in FIG. 29(*a*). The sensor readings 462, 464 are slightly delayed compared to the meter readings 460. The delay is most likely due to the delay between blood glucose and interstitial fluid (ISF) glucose and can be substantially corrected through the use of a filter if needed. In this study, the delay was not corrected by a filter and did not significantly affect the controller's ability to command an insulin response that matches the natural response of the NGT individual. This study indicates that the PID insulin response controller model is a good minimal model of insulin secretion that captures the biphasic response of healthy β-cells. Correction of the delay is only expected to increase the accuracy of the model.

Fuzzy Logic to Select Between Multiple Sets of Controller Gains

In preferred embodiments, one set of controller gains is used for a particular individual. In alternative embodiments, more than one set of controller gains is used, and fuzzy logic is used to select between sets of controller gains and to determine when to change from one set of controller gains to another. In particular alternative embodiments, the controller gains are different if the glucose level is above or below the desired glucose basal level. In other alternative embodiments, the controller gains are different if the glucose level is increasing or decreasing. A justification for different sets of gains comes from physiological studies that indicate that β-cells turn off faster than they turn on. In still other alternative embodiments, the controller gains are different depending on whether the glucose level is above or below the desired glucose basal level and whether the glucose level is increasing or decreasing, which results in four sets of controller gains. In additional alternative embodiments, the controller gains change depending on the magnitude of the hypoglycemic excursion. In other words, the controller gains for small changes in glucose are different than those for large changes in glucose.

Self-Tuning Controller Gains

Further embodiments may include a controller that self tunes one or more the gains, $K_P$, $K_I$, $K_D$ to accommodate changes in insulin sensitivity. In particular embodiments, previous measurements of glucose levels are compared to the desired basal glucose level $G_B$. For example, the desired basal glucose level $G_B$ is subtracted from the previous glucose level measurements. Then any negative values, within a predefined time window, are summed (in essence integrating the glucose level measurements that were below the basal glucose level $G_B$). If the resulting sum is greater than a pre-selected hypoglycemic integral threshold, then the controller gains are increased by a factor $(1+\alpha)$. Conversely, if the integral of the glucose level measurements that were measured above the basal glucose level $G_B$ within the predefined time window is greater than a pre-selected hyperglycemic integral threshold, then the controller gains are decreased by a factor $(1-\alpha)$.

In particular embodiments, the predefined time window over which the glucose concentration integrals are evaluated is generally 24 hours, and the controller gains are adjusted if needed at the end of each predefined time window. In alternative embodiments, the integrals of the glucose level measurements are continuously calculated over a moving window of time, and if either integral exceeds a threshold, the gains are immediately adjusted. In particular embodiments, the moving time window is one hour, and the time window may be restarted whenever the gains are adjusted. In other alternative embodiments, the time window is longer or shorter depending on the sensor accuracy, the rate at which an individual's insulin sensitivity changes, the computational capabilities of the hardware, or the like.

In particular embodiments, the adjustment amount ($\alpha$) is 0.01. In alternative embodiments, the adjustment amount a is greater or smaller depending on the sensor accuracy, the rate at which an individual's insulin sensitivity changes, the rate at which the sensor sensitivity $S_I$ changes, or the like. In still other alternative embodiments, the adjustment amount a is made larger or smaller depending on the amount that the integral of the measured glucose levels exceeds a threshold. In this way, the gains are adjusted by greater amounts if the measured glucose level G is significantly deviating from the desired blood glucose level $G_B$ and less if the measured glucose level G is closer to the desired blood glucose level $G_B$. In additional alternative embodiments, the controller employs a Kalman filter.

Post-Controller (Lead/Lag) Compensator

In preferred embodiments, commands are issued from the controller without regard to where in the body the insulin delivery system will infuse the insulin. In essence, the assumption is that the insulin is either delivered directly into the blood stream for immediate use by the body, or that any time delays caused by delivering the insulin somewhere in the body other than the blood stream are substantially insignificant to the user. In this case, the commands generally model a β-cell insulin secretion profile, an example of which is shown in FIG. 35(*a*). And since the β-cells secrete insulin directly into the blood stream, the β-cell insulin secretion profile is the intended blood plasma insulin concentration profile. However, an insulin delivery delay may distort the intended blood plasma insulin concentration profile, as shown in FIG. 35(*b*). The insulin delivery delay is the amount of time between the instant that the command is given to the insulin delivery system to infuse insulin and the time that insulin reaches the blood plasma. An insulin delivery delay may be caused by a diffusion delay, represented by a circle with an arrow 528 in FIG. 20, which is the time required for insulin that has been infused into a tissue to diffuse into the blood stream. Other contributors to insulin delivery delay may include, time for the delivery system to deliver the insulin to the body after receiving a command to infuse insulin, time for the insulin to spread through out the circulatory system once it has entered the blood stream, and/or by other mechanical or physiological causes. In addition, the body clears insulin even while an insulin dose is being delivered from the insulin delivery system into the body. Since insulin is continuously cleared from the blood plasma by the body, an insulin dose that is delivered to the-blood plasma too slowly or is delayed is at least partially, if not significantly, cleared before the entire insulin dose fully reaches the blood plasma. And therefore, the insulin concentration profile in the blood plasma never achieves the same peak (nor follows the same profile) it would have achieved if there were no delay. Given an insulin dose delivered all at once into the blood plasma at time zero, the insulin concentration in the blood plasma is raised virtually instantaneously (not shown) and then would decrease exponentially over time as the body clears (uses or filters out) the insulin, as shown in FIG. 36(*a*) per equation:

$$C_P = \frac{I_0}{V_P} e^{-P_1 t}$$

Where $C_P$ is the concentration of insulin in the blood plasma, $I_0$ is a mass of the insulin dose delivered directly to the blood plasma at time zero, $V_p$ is a volume of the blood plasma in the body, $P_1$ is a time constant for insulin clearance, and t is the time that has passed since the delivery of the insulin dose directly into the blood plasma.

The time constant for insulin clearance $P_1$ may be calculated using the following equation:

$$P_1 = -\frac{k}{V_P}$$

Where k is the volume insulin clearance rate, and $V_p$ is a volume of the blood plasma in the body.

Or the time constant for insulin clearance $P_1$ may be obtained by providing insulin to an individual that does not generate his own insulin, and then periodically testing blood samples from the individual for insulin concentration. Then, using an exponential curve fitting routine, generate a mathematical expression for a best-fit curve for the insulin concentration measurements, and observe the time constant in the mathematical expression.

Given the same insulin dose (delivered at time zero all at once) into the subcutaneous tissue, instead of directly into the blood plasma, the concentration of insulin in the blood plasma would begin to rise slowly as insulin diffuses from the interstitial fluid ISF into the blood plasma, as shown in FIG. 36(b). At the same time that insulin is entering the blood plasma, the body is clearing insulin from the blood. While the rate at which insulin is entering the blood plasma exceeds the insulin clearance rate, the insulin concentration in the blood plasma continues to increase. When the insulin clearance rate exceeds the rate at which insulin is entering the blood plasma from the interstitial fluid ISF, the insulin concentration in the blood plasma begins to decrease. So, the result of delivering insulin into the interstitial fluid ISF instead of directly into the blood stream is that the insulin concentration in the blood plasma is spread over time rather than increased virtually instantaneously to a peak followed by a decay.

A bi-exponential equation may be used to model the insulin concentration in blood plasma given an insulin dose delivered to the subcutaneous tissue:

$$C_P = \frac{I_0 D}{V_P V_{ISF}(P_3 - P_2)}(e^{-P_2 t} - e^{-P_3 t})$$

Where $C_P$ is the concentration of insulin in the blood plasma, $I_0$ is the mass of the insulin dose delivered to the subcutaneous tissue at time zero, D is a diffusion coefficient (the rate at which insulin diffuses from the interstitial fluid ISF into the blood glucose)

$V_p$ is a volume of the blood plasma in the body, $V_{SIF}$ is a volume of interstitial fluid ISF that the insulin is delivered to, $_{P2}$ is a time constant $P_3$ is a time constant greater than or equal to $P_2$, and t is time since the delivery of the insulin dose into the interstitial fluid ISF.

The time constants may be calculated using the quadratic formula:

$$P_2, P_3 = -\frac{a_1 \pm \sqrt{a_1^2 - 4a_0}}{2}$$

Where $$a_1 = \frac{D+K}{V_P} + \frac{D}{V_{ISF}}, \text{ and}$$

$$a_0 = \left(\frac{D+K}{V_P}\right)\left(\frac{D}{V_{ISF}}\right) - \frac{D^2}{V_{ISF} V_P}.$$

Figure 37:
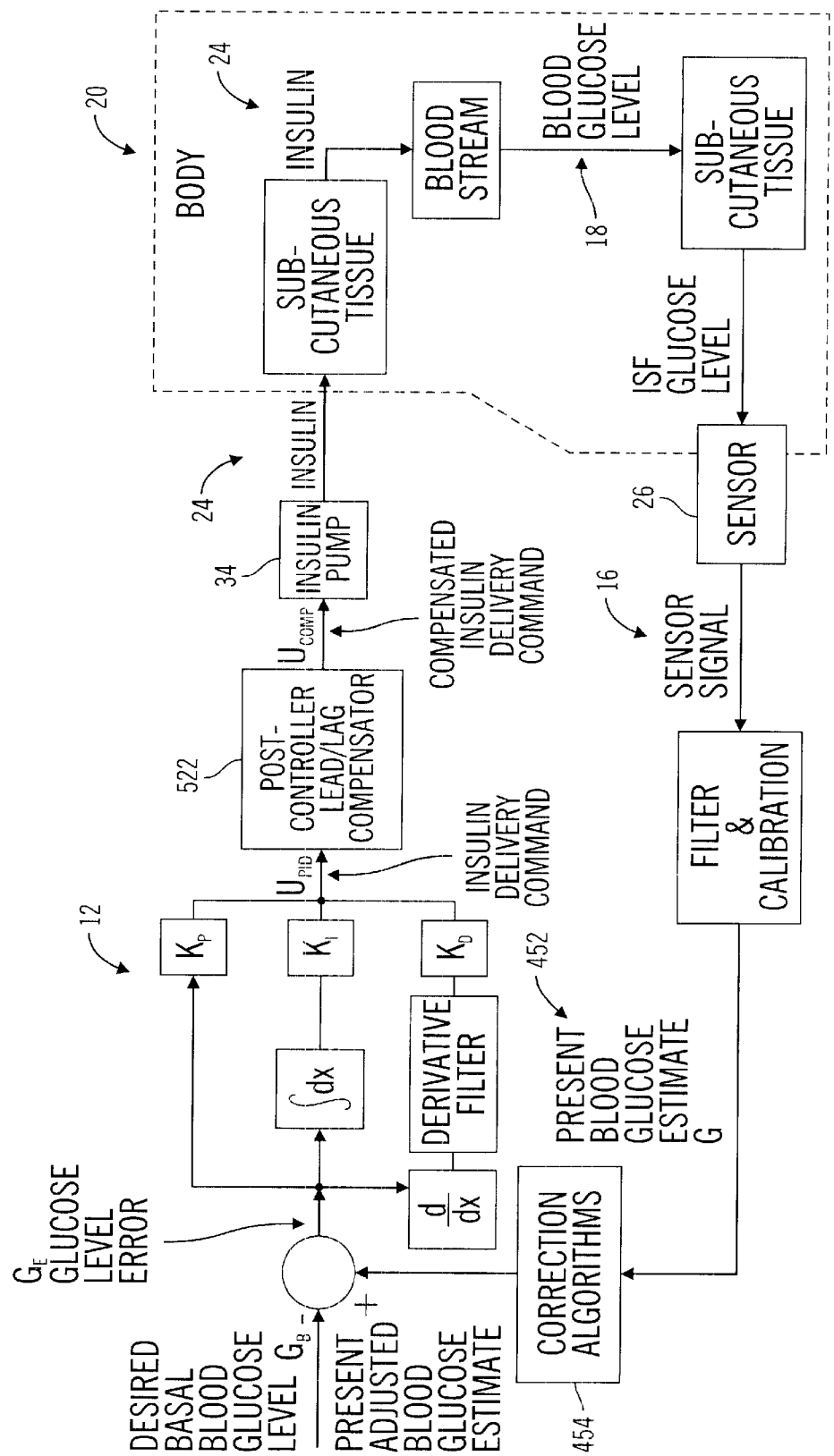
FIG. 37 is a block diagram of the closed loop system of FIG. 26 with the addition of a post-controller compensator and a derivative filter in accordance with an embodiment of the present invention.

In alternative embodiments, a post-controller lead-lag compensator 522 is used to modify the commands ($U_{PID}$) to compensate for the insulin delivery delay and/or the insulin clearance rate k, as shown in FIG. 37. The greater of the delay time constants, $P_3$, may be compensated for using the post-controller lead-lag compensator. The PID controller generates commands ($U_{PID}$) for a desired insulin delivery rate into the blood plasma. The commands $U_{PID}$ are calculated and issued periodically depending on the update rate for the control loop, which is selected based on a maximum anticipated rate of change of the blood glucose level, an insulin delivery system minimum insulin dosage, insulin sensitivity, a maximum and a minimum acceptable glucose concentration, or the like. The commands $U_{PID}$ are used as inputs to the post-controller lead-lag compensator 522.

In particular embodiments, the compensated commands ($U_{comp}$) issued from the post-controller lead-lag compensator 522 uses more than one value from the controller. In particular embodiments, post-controller lead-lag compensator 522 uses the present command ($U_{PID}{}^n$) and the previous command ($U_{PID}{}^{(n-1)}$) to calculate a compensated command $U_{comp}$ per a compensation equation:

$$U_{comp} = \frac{U_{PID}^n - U_{PID}^{(n-1)}}{\Delta t} + P_3 U_{PID}^n$$

Where $U_{PID}{}^n$ is the present command $U_{PID}{}^{(n-1)}$ is the previous command $P_3$ is a time constant greater than or equal to $P_2$, and $\Delta t$ is the change in time between the present command $U_{PID}{}^n$ and the previous command $U_{PID}{}^{(n-1)}$, also known as the update rate for the control loop. In other alternative embodiments, additional previous command values may be used. In still other alternative embodiments, the compensation equation compensates for both time constants $P_3$ and $P_2$.

In still more alternative embodiments, the controller gains are modified to include the effects of the post-controller lead/lag compensator so that the post-controller lead/lag compensator is not needed to modify the commands to account for the insulin delivery delay.

In particular embodiments, the insulin delivery system provides finite insulin doses into the body in response to commands from the controller. The smallest amount of insulin that the insulin delivery system can deliver is the minimum finite insulin dose. The controller may generate commands for a dose of insulin to be delivered that is not a whole number multiple of the minimum finite insulin dose.

Therefore, either too much or too little insulin is delivered by the insulin delivery system in response to the commands. In particular alternative embodiments, the post-controller lead-lag compensator truncates the command to the nearest whole number multiple of the minimum finite insulin dose and adds the remaining commanded volume of insulin to the next command. In other alternative embodiments, a compensator rounds the command to the nearest whole number multiple of the minimum finite insulin dose. In still other alternative embodiments, other methods are used to compensate for the difference between the commands and the nearest whole number multiple of the minimum finite insulin dose. In other embodiments, no compensation is needed.

System Configurations

The following sections provide exemplary, but not limiting, illustrations of components that can be utilized with the controller described above. Various changes in components, layout of various components, combinations of elements, or the like may be made without departing from the scope of the embodiments of the invention.

Figure 8:
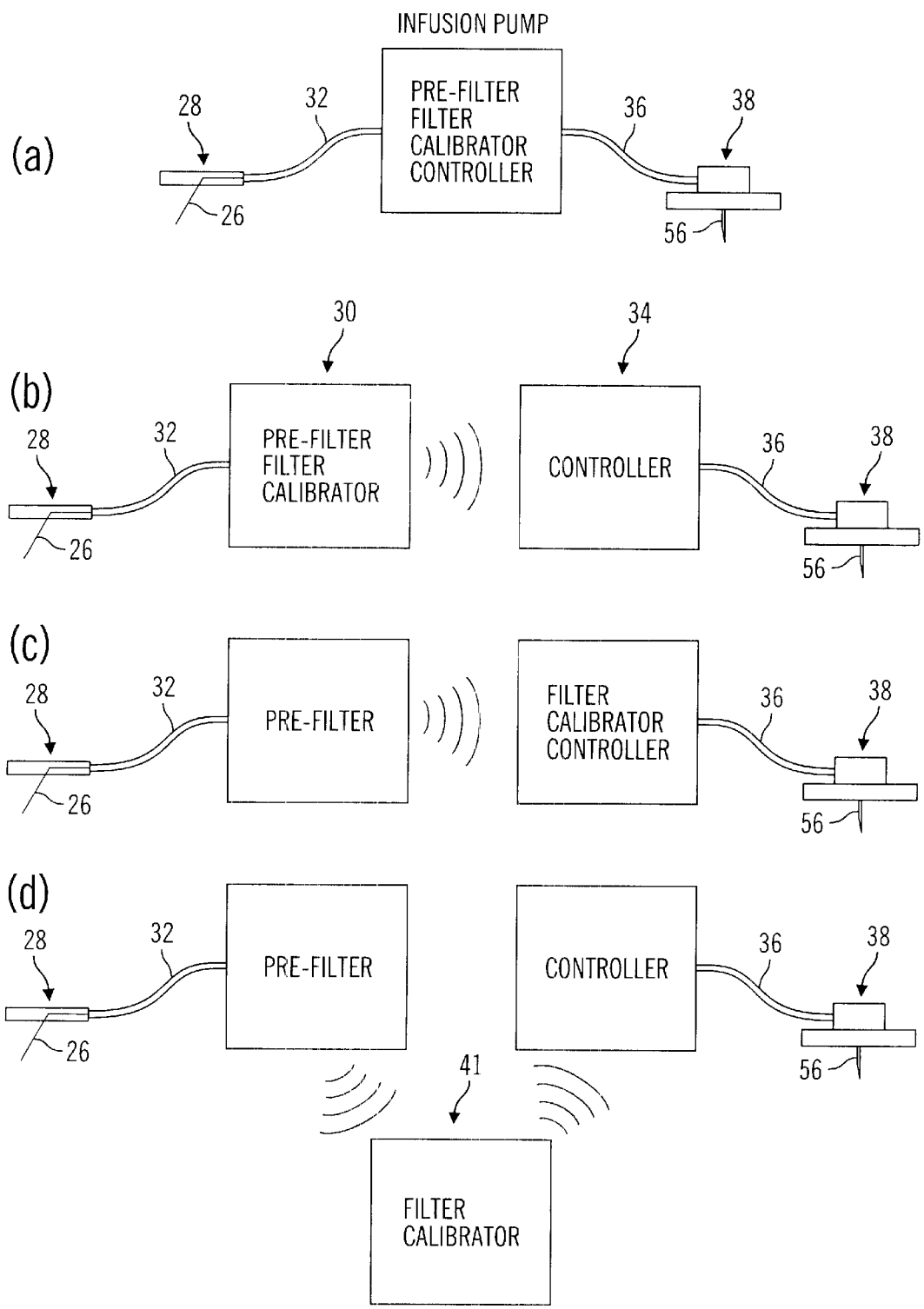
FIG. 8(a) is a diagram of a single device and its components in accordance with an embodiment of the present invention.
FIG. 8(b) is a diagram of two devices and their components in accordance with an embodiment of the present invention.
FIG. 8(c) is another diagram of two devices and their components in accordance with an embodiment of the present invention.
FIG. 8(d) is a diagram of three devices and their components in accordance with an embodiment of the present invention.

Before it is provided as an input to the controller 12, the sensor signal 16 is generally subjected to signal conditioning such as pre-filtering, filtering, calibrating, or the like. Components such as a pre-filter, one or more filters, a calibrator and the controller 12 may be split up or physically located together, and may be included with a telemetered characteristic monitor transmitter 30, the infusion device 34, or a supplemental device. In preferred embodiments, the pre-filter, filters and the calibrator are included as part of the telemetered characteristic monitor transmitter 30, and the controller 20 is included with the infusion device 34, as shown in FIG. 8(b). In alternative embodiments, the pre-filter is included with the telemetered characteristic monitor transmitter 30 and the filter and calibrator are included with the controller 12 in the infusion device, as shown in FIG. 8(c). In other alternative embodiments, the pre-filter may be included with the telemetered characteristic monitor transmitter 30, while the filter and calibrator are included in the supplemental device 41, and the controller is included in the infusion device, as shown in FIG. 8(d). To illustrate the various embodiments in another way, FIG. 9 shows a table of the groupings of components (pre-filter, filters, calibrator, and controller) in various devices (telemetered characteristic monitor transmitter, supplemental device, and infusion device) from FIGS. 8 (a–d). In other alternative embodiments, a supplemental device contains some of (or all of) the components.

In preferred embodiments, the sensor system generates a message that includes information based on the sensor signal such as digital sensor values, pre-filtered digital sensor values, filtered digital sensor values, calibrated digital sensor values, commands, or the like. The message may include other types of information as well such as a serial number, an ID code, a check value, values for other sensed parameters, diagnostic signals, other signals, or the like. In particular embodiments, the digital sensor values Dsig may be filtered in the telemetered characteristic monitor transmitter 30, and then the filtered digital sensor values may be included in the message sent to the infusion device 34 where the filtered digital sensor values are calibrated and used in the controller. In other embodiments, the digital sensor values Dsig may be filtered and calibrated before being sent to the controller 12 in the infusion device 34. Alternatively, the digital sensor values Dsig may be filtered, and calibrated and used in the controller to generate commands 22 that are then sent from the telemetered characteristic monitor transmitter 30 to the infusion device 34.

In further embodiments, additional optional components, such as a post-calibration filter, a display, a recorder, and a blood glucose meter may be included in the devices with any of the other components or they may stand-alone. Generally, if a blood glucose meter is built into one of the devices, it will be co-located in the device that contains the calibrator. In alternative embodiments, one or more of the components are not used.

In preferred embodiments, RF telemetry is used to communicate between devices, such as the telemetered characteristic monitor transmitter 30 and the infusion device 34, which contain groups of components. In alternative embodiments, other communication mediums may be employed between devices such as wires, cables, IR signals, laser signals, fiber optics, ultrasonic signals, or the like.

Filtering

Figure 16:
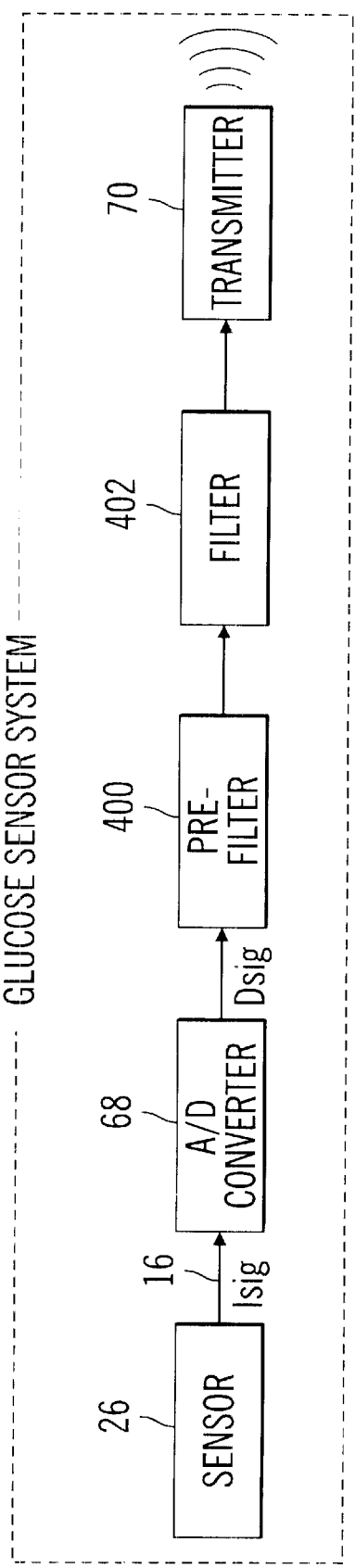
FIG. 16 is a block diagram of the glucose sensor system of FIG. 10 with a pre-filter and a filter in accordance with an embodiment of the present invention.

In preferred embodiments, the digital sensor values Dsig and/or the derivative of the digital sensor values are processed, filtered, modified, analyzed, smoothed, combined, averaged, clipped, scaled, calibrated, or the like, to minimize the effects of anomalous data points before they are provided as an input to the controller. In particular embodiments, the digital sensor values Dsig are passed through a pre-filter 400 and then a filter 402 before they are passed to the transmitter 70, as shown in FIG. 16. The filters are used to detect and minimize the effects of anomalous digital sensor values Dsig. Some causes of anomalous digital sensor values Dsig may include temporary signal transients caused by sensor separation from the subcutaneous tissue, sensor noise, power supply noise, temporary disconnects or shorts, and the like. In particular embodiments, each individual digital sensor value Dsig is compared to maximum and minimum value-thresholds. In other particular embodiments, the differences between consecutive pairs of digital sensor values Dsig are compared with rate-of-change-thresholds for increasing or decreasing values.

Pre-Filter

In particular embodiments, the pre-filter 400 uses fuzzy logic to determine if individual digital sensor values Dsig need to be adjusted. The pre-filter 400 uses a subset of a group of digital sensor values Dsig to calculate a parameter and then uses the parameter to determine if individual digital sensor values Dsig need to be adjusted in comparison to the group as a whole. For example, the average of a subset of a group of digital sensor values Dsig may be calculated, and then noise thresholds may be placed above and below the average. Then individual digital sensor values Dsig within the group are compared to noise thresholds and eliminated or modified if they are outside of the noise thresholds.

Figure 17:
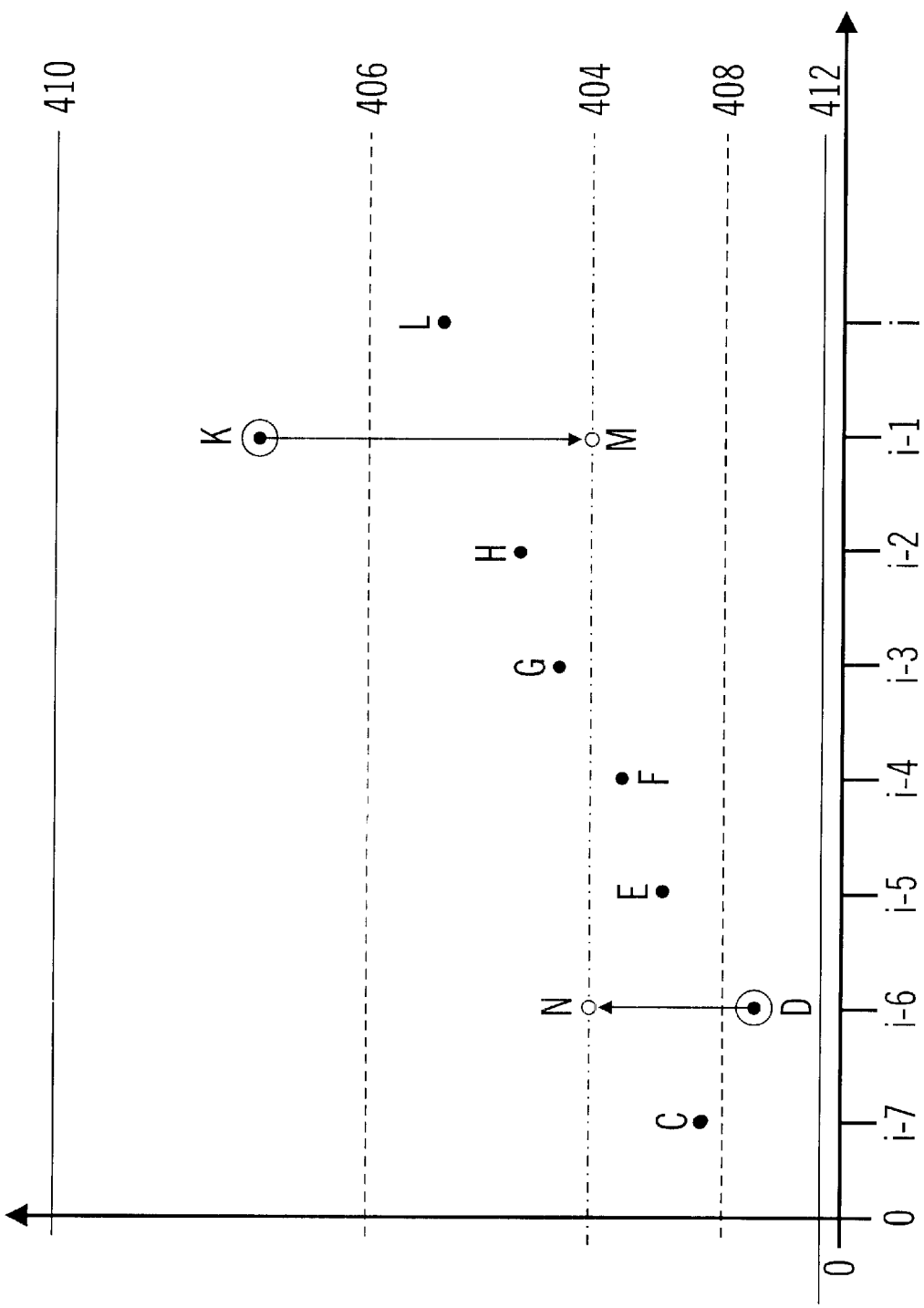
FIG. 17 is a chart of an example of a pre-filter of FIG. 16 and its effects on digital sensor values Dsig in accordance with an embodiment of the present invention.

A more detailed example is provided below to more clearly illustrate, but not limit, an embodiment of a pre-filter. A group of eight digital sensor values Dsig are shown in FIG. 17 including a most recently sampled value, labeled L, sampled from the analog sensor signal Isig at time i, and the seven previous values K, H, G, F, E, D, and C sampled at times (i−1) through (i−7). An average value is calculated using the four temporally middle values in the group, H, G, F, and E sampled at times (i−2) through (i−5). The calculated average value is represented as a dashed/dotted average line 404. A high noise threshold 406 is established at 100% above the average line 404. In other words, the magnitude of the high noise threshold 406 is two times the magnitude of the average line 404. A negative noise threshold 408 is established at 50% below the average line 404. In other words, the magnitude of the negative noise threshold 408 is one half of the magnitude of the average line 404. The individual magnitudes of each of the eight values, L, K, H, G, F, E, D, and C are compared to the high and negative noise thresholds 406 and 408. If a value is above the high noise threshold 406 or below the negative noise threshold 408 then the value is considered anomalous and the anomalous value is replaced with the magnitude of the average line 404. In the example shown in FIG. 17, the value K is above the high noise threshold 406 so it is replaced with the average value M. Also, the value D is below the negative noise threshold 408 so it is replaced with the average value N. In this way noisy signal spikes are reduced. Therefore, in the example, values L, K, H, G, F, E, D, and C are inputs to the pre-filter 400 and values L, M, H, G, F, E, N, and C are outputs from the pre-filter 400. In alternative embodiments, other noise threshold levels (or percentages) may be used. In other alternative embodiments, values outside of the thresholds may be replaced with values other than the average value, such as the previous value, the value of the closest threshold, a value calculated by extrapolating a trend line through previous data, a value that is calculated by interpolation between other values that are inside the thresholds, or the like.

In preferred embodiments, when any of a group's values are outside of the noise thresholds 406 or 408 then a warning flag is set. If one to three values are outside of the noise thresholds 406 or 408, a 'noise' flag is set. If more than three values are outside of the noise thresholds 406 or 408, a 'discard' flag is set which indicates that the whole group of values should be ignored and not used. In alternative embodiments, more or less values need be outside of the thresholds 406 or 408 to trigger the 'noise' flag or the 'discard' flag.

In preferred embodiments, each digital sensor value Dsig is checked for saturation and disconnection. To continue with the example of FIG. 17, each individual value is compared to a saturation threshold 410. If a value is equal to or above the saturation threshold 410 then a 'saturation' flag is set. In particular embodiments, when the 'saturation' flag is set, a warning is provided to the user that the sensor 26 may need calibration or replacement. In further particular embodiments, if an individual digital sensor value Dsig is at or above the saturation threshold 410, the individual digital sensor value Dsig may be ignored, changed to a value equal to the average line 404, or the entire group of values associated with the individual digital sensor value Dsig may be ignored. In preferred embodiments, the saturation threshold 410 is set at about 16% below the maximum value of the range of digital sensor values that may be generated. In preferred embodiments, the maximum digital sensor value represents a glucose concentration greater than 150 mg/dl. In alternative embodiments, the maximum digital sensor value may represent larger or smaller a glucose concentrations depending on the range of expected glucose concentrations to be measured, the sensor accuracy, the sensor system resolution needed for closed loop control, or the like. The full range of values is the difference between the maximum and the minimum digital sensor value that may be generated. Higher or lower saturation threshold levels may be used depending on an expected signal range of the sensor, sensor noise, sensor gains, or the like.

Similarly, in preferred embodiments, if a digital signal value Dsig is below a disconnect threshold 412, then a 'disconnect' flag is set indicating to a user that the sensor is not properly connected to the power supply and that the power supply or sensor may need replacement or recalibration. In further particular embodiments, if a digital sensor value Dsig is below the disconnect threshold 412, the individual value may be ignored, changed to a value equal to the average line 404, or the entire group of values associated with the individual digital sensor value Dsig may be ignored. In preferred embodiments, the disconnect threshold 410 is set at about 20% of the full range of values. Higher or lower disconnect threshold levels may be used depending on an expected signal range of the sensor, sensor system noise, sensor gains, or the like.

In alternative embodiments, other methods are used to pre-filter the digital sensor values Dsig such as rate-of-change thresholds, rate-of-change squared thresholds, noise thresholds about a least squares fit line rather than about the average of a subset of a group's values, higher or lower noise threshold lines, or the like.

Noise Filter

After the digital sensor values Dsig are evaluated, and if necessary, modified by the pre-filter 400, the digital sensor values Dsig are passed to the filter 402. The filter 402 may be used to reduce noise in particular frequency bands. Generally the body's blood glucose level 18 changes relatively slowly compared to a rate at which digital sensor values Dsig are collected. Therefore, high frequency signal components are typically noise, and a low pass filter may be used to improve the signal to noise ratio.

Figure 18:
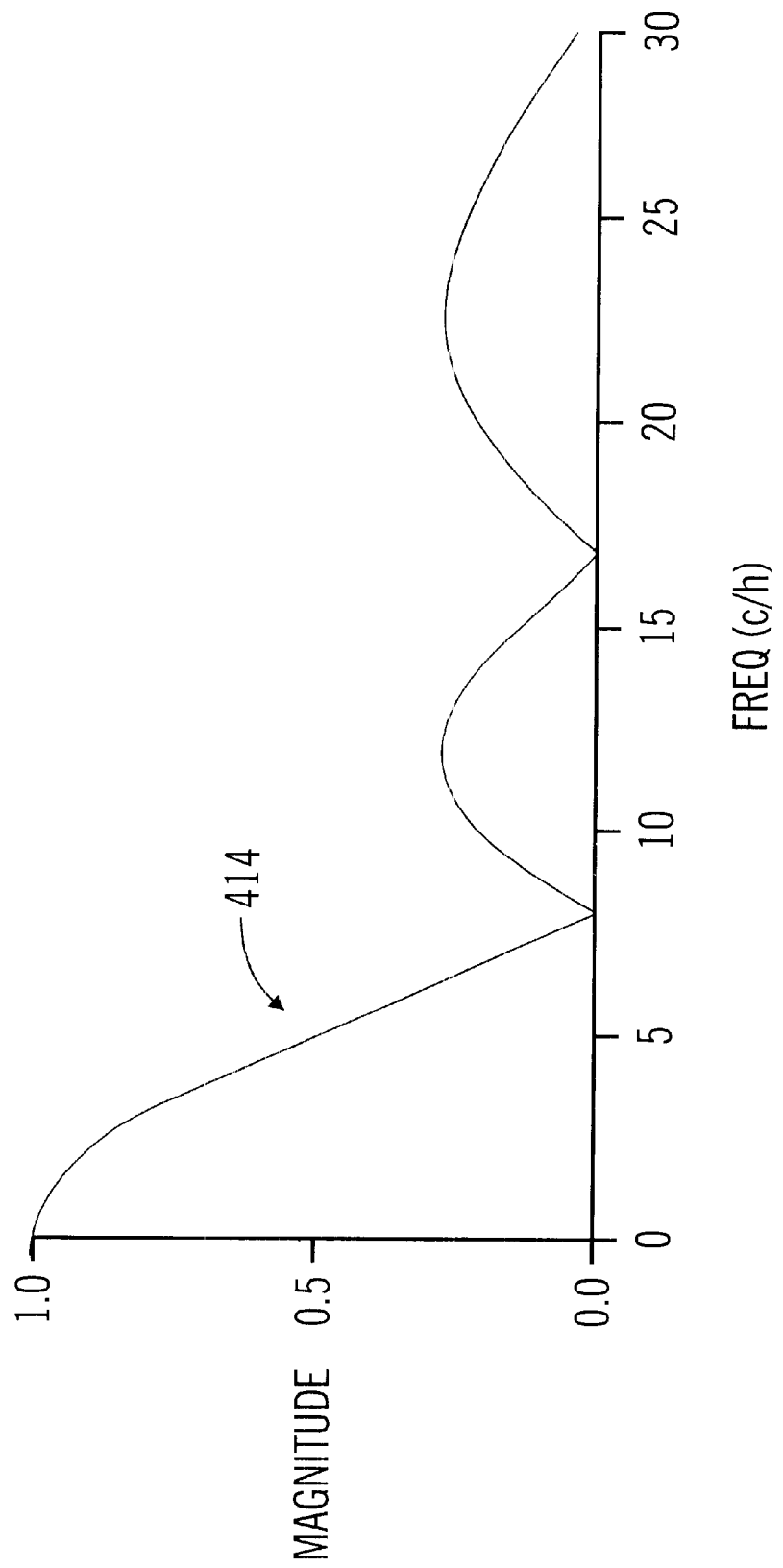
FIG. 18 is frequency response chart for a filter of FIG. 16 in accordance with an embodiment of the present invention.
Figure 19:
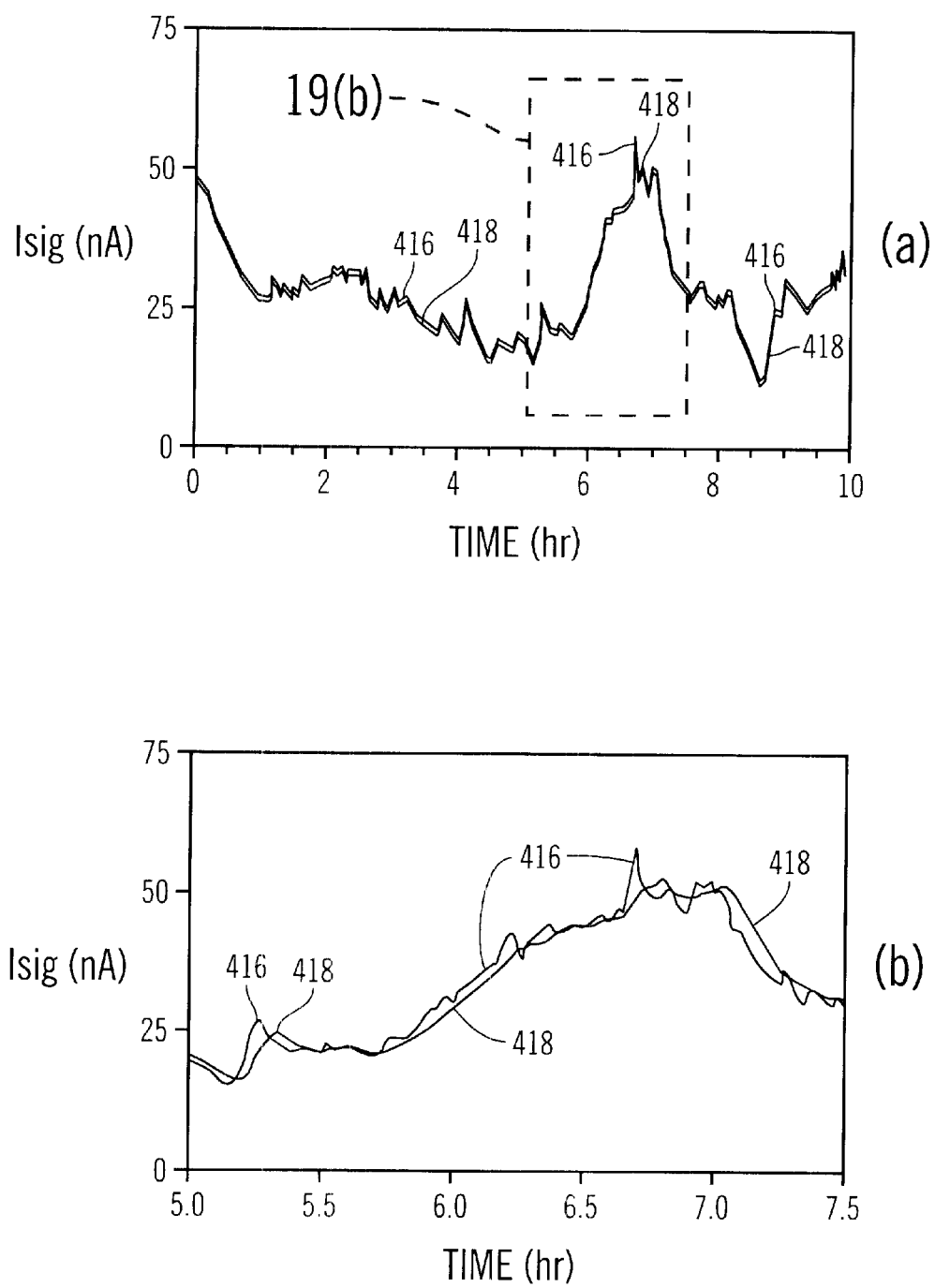
FIG. 19(a) is a plot of a filtered and an unfiltered sensor signal over time in accordance with an embodiment of the present invention.
FIG. 19(b) is close up of a section of the plot of FIG. 19(a) in accordance with an embodiment of the present invention.

In preferred embodiments, the filter 402 is a finite impulse response (FIR) filter used to reduce noise. In particular embodiments, the FIR filter is a $7^{th}$ order filter tuned with a pass band for frequencies from zero to 3 cycles per hour (c/hr) and a stop band for frequencies greater than about 6 c/hr, as shown in an example frequency response curve 414 in FIG. 18. However, typically FIR filters tuned with a pass band for frequencies from zero up to between about 2 c/hr and 5 c/hr and a stop band beginning at 1.2 to three times the selected pass band frequency will sufficiently reduce noise while passing the sensor signal. In particular embodiments, FIR filters tuned with a pass band for frequencies from zero up to between about 2 c/hr and 10 c/hr and a stop band beginning at 1.2 to three times the selected pass band frequency will sufficiently reduce noise. In the $7^{th}$ order filter, unique weighting factors are applied to each of eight digital sensor values Dsig. The digital sensor values Dsig include the most recently sampled value and the seven previous values. The effects of a low pass filter on a digital sensor values collected at one minute intervals is shown in FIGS. 19(a) and (b). An unfiltered sensor signal curve 416 of digital sensor values is contrasted with a curve of the same signal after the effects of a $7^{th}$ order FIR filter 418. The filtered .signal curve 418 is delayed and the peaks are smoother compared to the unfiltered sensor signal curve 416. In other particular embodiments, higher or lower order filters may be used. In still other particular embodiments, filter weighting coefficients may be applied to digital sensor values Dsig collected at time intervals shorter or longer than one minute depending on the desired sensor sample rate based on the body's physiology, the computational capabilities of the telemetered characteristic monitor transmitter 30, the sensor's response time, or the like. In alternative embodiments, filters with other frequency responses may be used to eliminate other noise frequencies depending on the type of sensor, noise from the power supply or other electronics, the sensor's interaction with the body, the effects of body motion on the sensor signal, or the like. In still other alternative embodiments, the filter is an infinite impulse response (IIR) filter.

Delay Compensation Filter

Aside from noise reduction, a filter may used to compensate for time delays. Ideally, a sensor would provide a real time, noise-free measurement of a parameter that a control system is intended to control, such as a blood glucose measurement. However, realistically there are physiological, chemical, electrical, and algorithmic sources of time delays that cause the sensor measurement to lag behind the present value of blood glucose.

A physiological delay 422 is due to the time required for glucose to move between blood plasma 420 and interstitial fluid (ISF). The delay is represented by the circled double headed arrow 422 in FIG. 20. Generally, as discussed above, the sensor 26 is inserted into the subcutaneous tissue 44 of the body 20 and the electrodes 42 near the tip of the sensor 40 are in contact with interstitial fluid (ISF). But the desired parameter to be measured is the concentration of blood glucose. Glucose is carried throughout the body in blood plasma 420. Through the process of diffusion, glucose moves from the blood plasma 420 into the ISF of the subcutaneous tissue 44 and vice versa. As the blood glucose level 18 changes so does the glucose level in the ISF. But the glucose level in the ISF lags behind the blood glucose level 18 due to the time required for the body to achieve glucose concentration equilibrium between the blood plasma 420 and the ISF. Studies show the glucose lag times between blood plasma 420 and ISF vary between 0 to 30 minutes. Some parameters that may affect the glucose lag time between blood plasma 420 and ISF are the individual's metabolism, the current blood glucose level, whether the glucose level is rising, or falling, or the like.

Figure 20:
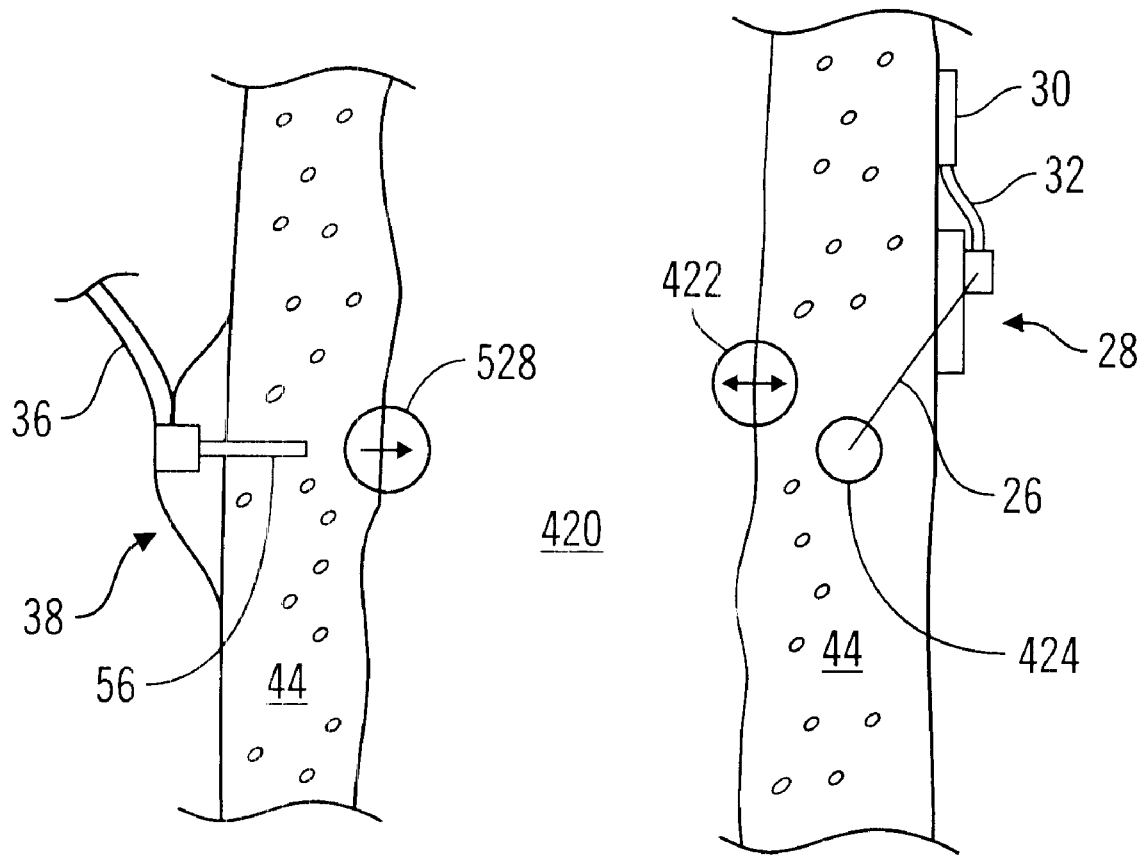
FIG. 20 is a cross-sectional view of a sensor set and an infusion set attached to the body in accordance with an embodiment of the present invention.

A chemical reaction delay 424 is introduced by the sensor response time, represented by the circle 424 surrounding the tip of the sensor 26 in FIG. 20. The sensor electrodes 42 are coated with protective membranes that keep the electrodes 42 wetted with ISF, attenuate the glucose concentration, and reduce glucose concentration fluctuations on the electrode surface. As glucose levels change, the protective membranes slow the rate of glucose exchange between the ISF and the electrode surface. In addition, there is a chemical reaction delay simply due to the reaction time for glucose to react with glucose oxidase GOX to generate hydrogen peroxide, and the reaction time for a secondary reaction, the reduction of hydrogen peroxide to water, oxygen and free electrons.

There is also a processing delay as the analog sensor signal Isig is converted to digital sensor values Dsig. In preferred embodiments, the analog sensor signal Isig is integrated over one-minute intervals and then converted to a number of counts. In essence an A/D conversion time results in an average delay of 30 seconds. In particular embodiments, the one-minute values are averaged into 5-minute values before they are sent to the controller. The resulting average delay is two and one half minutes. In alternative embodiments, longer or shorter integration times are used resulting in longer or shorter delay times. In other embodiments the analog sensor signal current Isig is continuously converted to an analog voltage Vsig and a A/D converter samples the voltage Vsig every 10 seconds. Then six 10-second values are pre-filtered and averaged to create a one-minute value. Finally, five 1-minute values are filtered and then averaged creating a five-minute value resulting in an average delay of two and one half minutes. Other embodiments use other electrical components or other sampling rates and result in other delay periods.

Filters also introduce a delay due to the time required to acquire a sufficient number of digital sensor values Dsig to operate the filter. Higher order filters, by definition, require more digital sensor values Dsig. Aside from the most recent digital sensor value Dsig, FIR filters use a number of previous values equal to the order of the filter. For example, a $7^{th}$ order filter uses 8 digital sensor values Dsig. There is a time interval between each digital sensor value Dsig. To continue with the example, if the time interval between digital sensor values Dsig is one minute, then the oldest digital sensor value Dsig used in a $7^{th}$ order FIR filter would be seven minutes old. Therefore, the average time delay for all of the values used in the filter is three and a half minutes. However, if the weighting factors associated with each of the values are not equal then the time delay may be longer or shorter than three and one half minutes depending on the effects of the coefficients.

Figure 21:
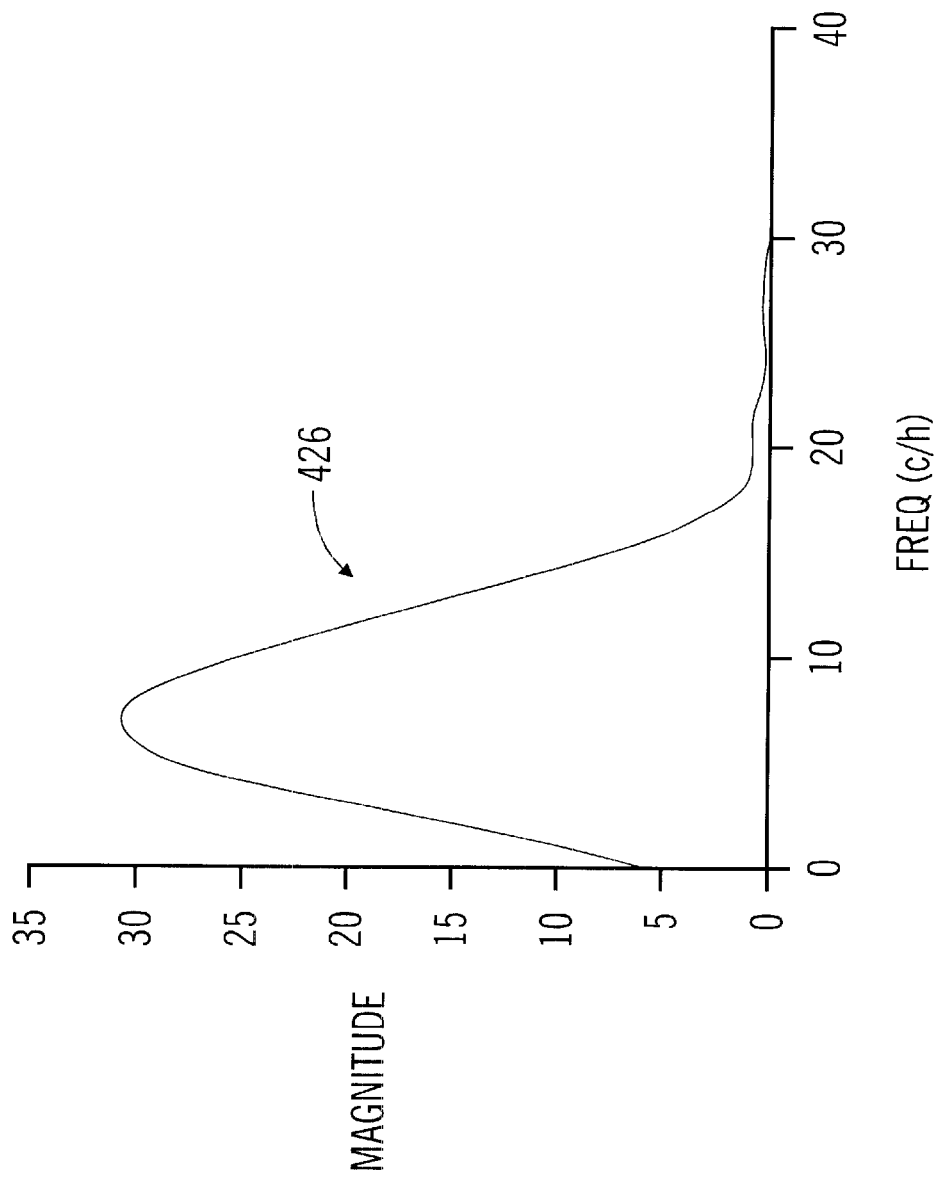
FIG. 21 is a frequency response chart of a time delay correcting Weiner filter in accordance with an embodiment of the present invention.
Figure 22:
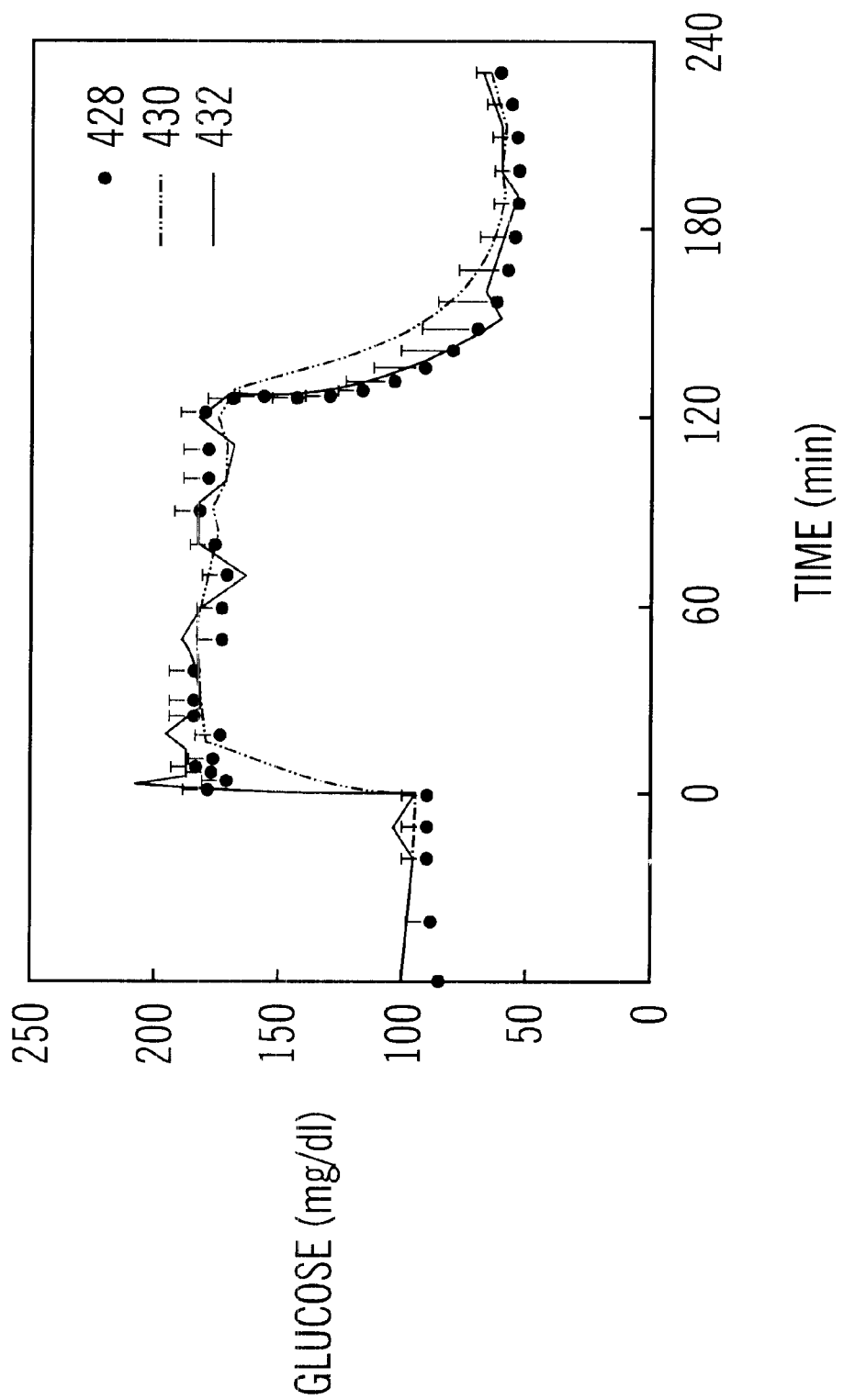
FIG. 22 is a plot of a digital sensor values Dsig before and after time delay correction compared to actual glucose measurements over time in accordance with an embodiment of the present invention.

Preferred embodiments of the invention include a FIR filter that compensates for both the various time delays, of up to about 30 minutes as discussed above, and high frequency noise, greater than about 10 c/hr also discussed above. Particular embodiments employ a $7^{th}$ order Weiner type FIR filter. The coefficients for the filter are selected to correct for time lags while simultaneously reducing high frequency noise. An example of a frequency response curve 426 is shown in FIG. 21. The example frequency response curve 416 is generated for a Weiner filter with a pass band for frequencies from zero up to about 8 c/hr and a stop band for frequencies greater than about 15 c/hr for a sensor with a sensitivity of about 20 $\mu$A/100 mg/dl. A study conducted with sensors in dogs demonstrates that a FIR filter may be used to compensate for time delays. During the study a filter was used to compensate for a time delay of about 12 minutes. The results, presented in FIG. 22, show dots 428 representing actual blood plasma glucose levels measured with a blood glucose meter, a broken line 430 representing sensor measurements without delay compensation, and a solid line 432 representing sensor measurements with delay compensation. The sensor in the test was abnormally low in sensitivity. Studies with average sensitivity sensors in humans are indicating a time delay of about 3 to 10 minutes is more normal. Other filter coefficients and other orders of filters may be used to compensate for the time delay and/or noise.

In alternative embodiments, other types of filters may be used as long as they remove a sufficient portion of the noise from the sensor signal. In other alternative embodiments, no time compensation is used if the rate of change in the blood glucose level is slow compared to the time delay. For example, a five-minute delay between blood plasma glucose and a sensor measurement does not have to be corrected for a closed loop glucose control system to function.

Derivative Filter

Further embodiments may include a filter to remove noise from the derivative of the sensor signal before the controller uses it. A derivative is taken from the digital sensor values Dsig, which results in digital derivative sensor values (dDsig/dt). The digital derivative sensor values dDsig/dt are passed through a FIR filter. In particular embodiments, the derivative filter is at least a $7^{th}$ order FIR filter tuned to remove high frequency noise. In alternative embodiments, higher or lower order filters may be used and the filters may be tuned to remove various frequencies of noise. In other alternative embodiments, a derivative is taken from the glucose level error $G_E$ values and then passed through a derivative filter 526, as shown in FIG. 37. In further alternative embodiments, a derivative is taken of an analog sensor signal Isig and a hardware filter is used to remove noise.

Calibration

In preferred embodiments, after filtering, the digital sensor values Dsig are calibrated with respect to one or more glucose reference values. The glucose reference values are entered into the calibrator and compared to the digital sensor values Dsig. The calibrator applies a calibration algorithm to convert the digital sensor values Dsig, which are typically in counts into blood glucose values. In particular embodiments, the calibration method is of the type described in U.S. patent application Ser. No. 09/511,580, filed on Feb. 23, 2000, entitled "GLUCOSE MONITOR CALIBRATION METHODS", which is incorporated by reference herein. In particular embodiments, the calibrator is included as part of the infusion device 34 and the glucose reference values are entered by the user into the infusion device 34. In other embodiments, the glucose reference values are entered into the telemetered characteristic monitor transmitter 30 and the calibrator calibrates the digital sensor values Dsig and transmits calibrated digital sensor values to the infusion device 34. In further embodiments, the glucose reference values are entered into a supplemental device where the calibration is executed. In alternative embodiments, a blood glucose meter is in communication with the infusion device 34, telemetered characteristic monitor transmitter 30 or supplemental device so that glucose reference values may be transmitted directly into the device that the blood glucose meter is in communication with. In additional alternative embodiments, the blood glucose meter is part of the infusion device 34, telemetered characteristic monitor transmitter 30 or supplemental device such as that shown in U.S. patent application Ser. No. 09/334,996, filed on Jun. 17, 1999, entitled "CHARACTERISTIC MONITOR WITH A CHARACTERISTIC METER AND METHOD OF USING THE SAME", which is incorporated by reference herein.

In preferred embodiments, to obtain blood glucose reference values, one or more blood samples are extracted from the body 20, and a common, over-the-counter, blood glucose meter is used to measure the blood plasma glucose concentration of the samples. Then a digital sensor value Dsig is compared to the blood glucose measurement from the meter and a mathematical correction is applied to convert the digital sensor values Dsig to blood glucose values. In alternative embodiments, a solution of a known glucose concentration is introduced into the subcutaneous tissue surrounding the sensor 26 by using methods and apparatus such as described in U.S. patent application Ser. No. 09/395,530, filed on Sep. 14, 1999, entitled "METHOD AND KIT FOR SUPPLYING A FLUID TO A CUBCUTANEOUS PLACEMENT SITE", which is incorporated by reference herein, or by using injection, infusion, jet pressure, introduction through a lumen, or the like. A digital sensor value Dsig is collected while the sensor 26 is bathed in the solution of known glucose concentration. A mathematical formula such as a factor, an offset, an equation, or the like, is derived to convert the digital sensor value Dsig to the known glucose concentration. The mathematical formula is then applied to subsequent digital sensors values Dsig to obtain blood glucose values. In alternative embodiments, the digital sensor values Dsig are calibrated before filtering. In additional alternative embodiments, the digital sensor values Dsig are calibrated after pre-filtering and before filtering. In other alternative embodiments, the sensors are calibrated before they are used in the body or do not require calibration at all.

Sensor Signal Processing Systems

Figure 10:
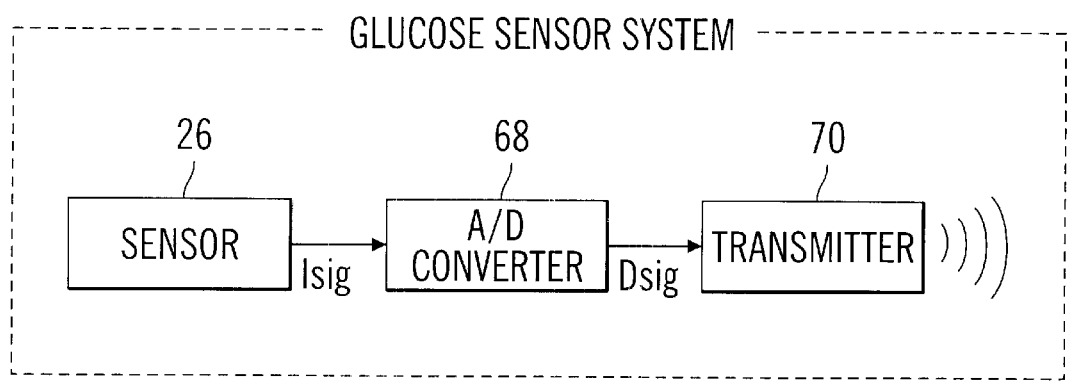
FIG. 10 is a block diagram of the glucose sensor system of FIG. 3(a).
Figure 11:
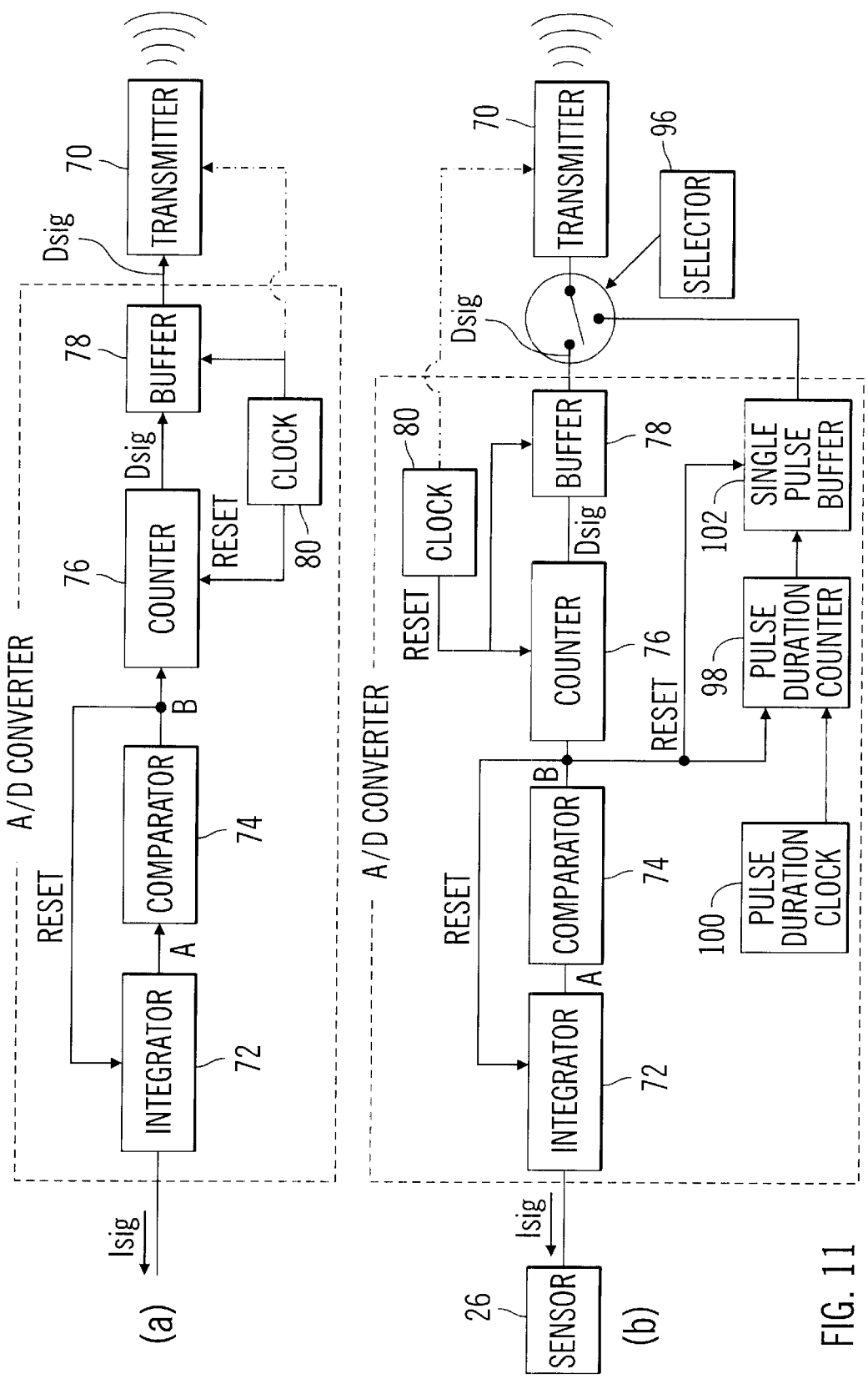
FIG. 11(a) is a detailed block diagram of an A/D converter for the glucose sensor system of FIG. 10 in accordance with an embodiment of the present invention.
FIG. 11(b) is a detailed block diagram of the A/D converter for the glucose sensor system of FIG. 10 with a pulse duration output selection option in accordance with an embodiment of the present invention.

Before filtering and calibrating, generally the sensor signal is processed to convert the sensor signal from a raw form into a form acceptable for use in the filters and/or calibrator. In preferred embodiments, as shown in FIG. 10, an analog sensor signal Isig is digitally quantified through an A/D converter 68 resulting in digital sensor values Dsig that are transmitted by a transmitter 70 from the telemetered characteristic monitor transmitter 30 to another device. In particular embodiments, the analog sensor signal Isig is an analog current value that is converted to a digital sensor value Dsig in the form of a digital frequency measurement, as shown in FIG. 11(*a*). The general circuit includes an integrator 72, a comparator 74, a counter 76, a buffer 78, a clock 80 and the transmitter 70. The integrator 72 generates a substantially ramped voltage signal (A), and the instantaneous slope of the ramped voltage signal is proportional to the magnitude of the instantaneous analog sensor signal Isig. The comparator 74 converts the ramped voltage signal (A) from the integrator 72 into square wave pulses (B). Each pulse from the comparator 74 increments the counter 76 and also resets the integrator 72. The clock 80 periodically triggers the buffer 78 to store the present value from the counter 76 and then resets the counter 76. The values stored in the buffer 78 are the digital sensor values Dsig. The clock 80 may also periodically signal the transmitter 70 to send a value from the buffer 78. In preferred embodiments, the clock period is one minute. However, in alternative embodiments, the clock period may be adjusted based on how often measurements are needed, sensor signal noise, sensor sensitivity, required measurement resolution, the type of signal to be transmitted, or the like. In alternative embodiments, a buffer is not used.

A/D Converters

Various A/D converter designs may be used in embodiments of the present invention. The following examples are illustrative, and not limiting, since other A/D converters may be used.

I to F (Current to Frequency (Counts)), Single Capacitor, Quick Discharge

In preferred embodiments, the integrator 72 consists of a first Op-Amp 92 and a capacitor 82, shown in FIG. 12. The integrator 72 sums the analog sensor signal Isig current by charging the capacitor 82 until the capacitor voltage (A') achieves a high reference voltage (VrefH). The capacitor voltage (A') is measured at the output of the first Op-Amp 92. A second Op-Amp 94 is used as a comparator. When the capacitor voltage (A') reaches VrefH, the comparator output (B') changes from low to high. The high comparator output (B') closes a reset switch 84 that discharges the capacitor 82 through a voltage source (V+). The high comparator output (B') also triggers a reference voltage switch 88 to close, while substantially simultaneously an inverter 86 inverts the comparator output (B'). And the inverter output (C') triggers a reference voltage switch 90 to open. The result is that the reference voltage of the comparator is changed from VrefH to the low reference voltage (VrefL).

When the capacitor voltage (A') is discharged to VrefL, the comparator output (B') returns to low, thus forming a pulse. The low comparator output (B') opens the reset switch 84 allowing the capacitor 82 to begin charging again.

Virtually simultaneously, the low comparator output (B') also triggers the reference voltage switch 88 to open and the inverter output (C') triggers reference voltage switch 90 to close resulting in changing the comparator reference voltage from VrefL back to VrefH.

I to F, Single Reversible Capacitor

In alternative embodiments, two or more integrator switches are used to control the polarity of one or more capacitors. A particular embodiment is shown in FIG. 13. Generally, only one of the two integrator-switches 110 and 112 is closed and the other integrator switch is open. When the first integrator switch 110 is closed, the second integrator switch 112 is open and an integrator Op-Amp 114 sums the analog sensor signal Isig current by charging a capacitor 116 until the capacitor voltage (A") achieves a high reference voltage (VrefH). The comparator 120 compares the integrator output (A") to the reference voltage VrefH. And when the capacitor voltage (A") reaches VrefH, the comparator output (B") shifts from low to high, initiating a pulse.

The high comparator output (B") pulse causes the capacitor polarity to reverse using the following method. The high comparator output (B") triggers the second integrator switch 112 to close while virtually simultaneously the inverter 118 inverts the comparator output (B"). And the low inverter output (C") pulse triggers the first integrator switch 110 to open. Once the capacitor's polarity is reversed, the capacitor 116 discharges at a rate proportional to the analog sensor signal Isig. The high comparator output (B") pulse also triggers the reference voltage of the comparator to change form VrefH the low reference voltage (VrefL). When the capacitor voltage (A") is discharged to VrefL, the comparator output (B") returns to low. The low comparator output (B") opens the second integrator switch 112 and virtually simultaneously the high inverter output (C") closes the first integrator switch 110 allowing the capacitor 116 to begin charging again. The low comparator output (B") also triggers the comparator reference voltage to change from VrefL back to VrefH.

An advantage of this embodiment is that sensor signal errors, which may be created due to capacitor discharge time, are reduced since the magnitude of the analog sensor signal Isig drives both the charging and the discharging rates of the capacitor 116.

I to F, Dual Capacitor

In further alternative embodiments, more than one capacitor is used such that as one capacitor is charging, at a rate proportional to the magnitude of the analog sensor signal Isig, another capacitor is discharging. An example of this embodiment is shown in FIG. 14. A series of three switches are used for each capacitor. A first group of switches 210 is controlled by a latch voltage C'", and a second group of switches 212 are controlled by voltage D'", which is the inverse of C'". Substantially, only one group of switches is closed at a time. When the first group of switches 210 is closed, the voltage across a first capacitor 216 increases at a rate proportional to the analog sensor signal Isig until the integrator voltage (A'") at the output of Op-Amp 214 achieves a reference voltage (Vref). At the same time one of the switches shorts the circuit across a second capacitor 222 causing it to discharge. A comparator 220 compares the integrator output (A'") to the reference voltage Vref. And when the integrator output (A'") reaches Vref, the comparator output (B'") generates a pulse. The comparator output pulse increments a counter 76, and triggers the latch output voltage C'" from a latch 221 to toggle from a low voltage to a high voltage. The change in the latch voltage C'" causes the second group of switches 212 to close and the first group of switches 210 to open. One of the switches from the second group of switches 212 shorts the circuit across the first capacitor 216 causing it to discharge. At the same time the voltage across the second capacitor 222 increases at a rate proportional to the analog sensor signal Isig until the integrator voltage (A'") at the output of Op-Amp 214 achieves a reference voltage (Vref). Again, the comparator 220 compares the integrator output (A'") to the reference voltage Vref. And when the integrator output (A'") reaches Vref, the comparator output (B'") generates a pulse. The comparator output pulse increments the counter 76, and triggers the latch output voltage C'" to toggle from a high voltage to a low voltage, which causes the switches to return to their initial position with the first group of switches 210 closed and the second group of switches 212 to open.

In summary, as the blood glucose level 18 increases, the analog sensor signal Isig increases, which causes the voltage coming out of the integrator 72 to ramp up faster to the high reference voltage VrefH, which causes the comparator 74 to generate pulses more often, which adds counts to the counter 76 faster. Therefore, higher blood glucose levels generate more counts per minute.

The charge storage capacity for the capacitors used in the integrator 72, and the reference voltages VrefH, and VrefL are selected such that the count resolution for counts collected in a one-minute period at a glucose level of 200 mg/dl represents a blood glucose measurement error of less than 1 mg/dl. In particular embodiments, VrefH is 1.1 volts and VrefL is 0.1 volts. Higher or lower reference voltages may be selected based on the magnitude of the analog sensor signal Isig, the capacity of the capacitors, and the desired measurement resolution. The source voltage V+ is set to a voltage sufficiently high to discharge one or more capacitors quickly enough that the discharge times do not significantly reduce the number of counts per minute at a blood glucose level of 200 mg/dl.

Pulse Duration Output Feature

In preferred embodiments, the transmitter 70 transmits the digital sensor values Dsig from the buffer 78 whenever triggered by the clock 80. However, in particular embodiments, the user or another individual may use a selector 96 to choose other outputs to be transmitted from the transmitter 70, as shown in FIG. 11(b). In preferred embodiments, the selector 96 is in the form of a menu displayed on a screen that is accessed by the user or another individual by using buttons on the surface of the telemetered characteristic monitor transmitter 30. In other embodiments, a dial selector, dedicated buttons, a touch screen, a signal transmitted to the telemetered characteristic monitor transmitter 30, or the like, may be used. Signals that may be selected to be transmitted, other than the digital sensor values Dsig, include, but are not limited to, a single pulse duration, digital sensor values before pre-filtering, digital sensor values after pre-filtering but before filtering, digital sensor values after filtering, or the like.

In particular embodiments, a pulse duration counter 98 counts clock pulses from a pulse duration clock 100 until the pulse duration counter 98 is reset by a rising or falling edge of a pulse from the comparator 74, as shown in FIG. 11(b). The accumulated count at the time that the pulse duration counter 98 is reset represents the pulse duration for a portion of a single pulse from the comparator 74. The accumulated count from the pulse duration counter 98 is stored in the single pulse buffer 102 when triggered by the reset signal. When an individual selects the single pulse output, the transmitter 70 transmits the values from the single pulse buffer 102. The pulse duration clock 100 period must be sufficiently shorter than the period between individual pulse edges from the comparator 74 given a high analog sensor signal Isig to have sufficient resolution to quantify different pulse durations from the comparator 74.

I to V (Current to Voltage), Voltage A/D

Figure 15:
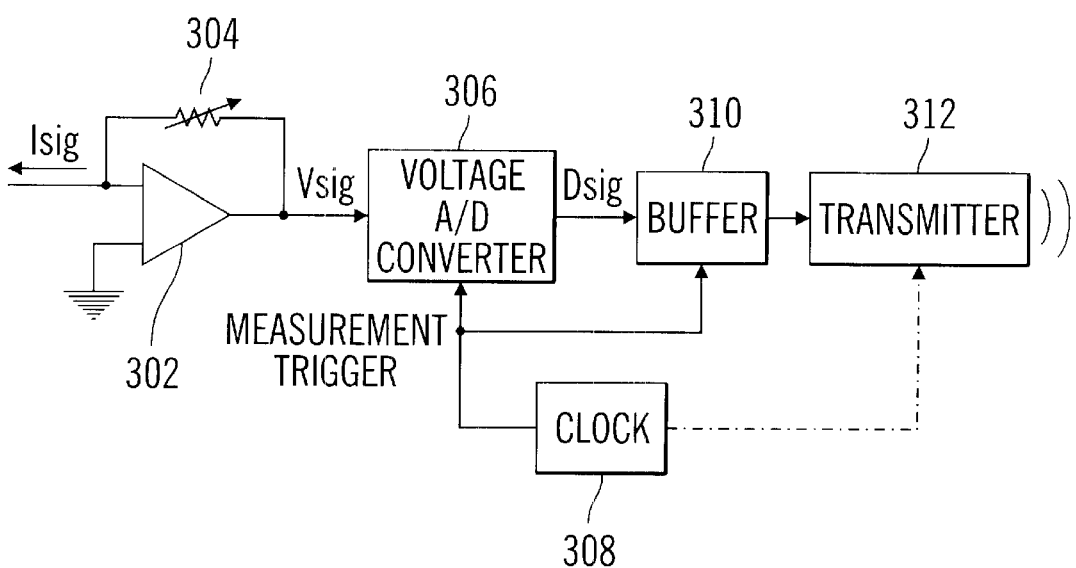
FIG. 15 is a circuit diagram of an I-V A/D converter of FIG. 10 in accordance with an embodiment of the present invention.

Alternative methods may be used to convert the analog sensor signal Isig from an analog current signal to a digital voltage signal. The analog sensor signal Isig is converted to an analog voltage Vsig using an Op Amp 302 and a resistor 304, as shown in FIG. 15. And then periodically a clock 308 triggers an A/D converter 306 to take a sample value from the analog voltage Vsig and convert it to a digital signal representing the magnitude of the voltage. The output values of the A/D converter 306 are digital sensor values Dsig. The digital sensor values Dsig are sent to a buffer 310 and then to the transmitter 70. In particular embodiments, the resistor 304 may be adjusted to scale the Vsig to use a significant portion of the range of the voltage A/D converter 306 depending on the sensor sensitivity, the maximum glucose concentration to be measured, the desired resolution from the voltage A/D converter 306, or the like.

In alternative embodiments, a buffer 310 is not needed and the digital sensor values Dsig are sent from the A/D converter directly to the transmitter 70. In other alternative embodiments, the digital sensor values Dsig are processed, filtered, modified, analyzed, smoothed, combined, averaged, clipped, scaled, calibrated, or the like, before being sent to the transmitter 70. In preferred embodiments, the clock 308 triggers a measurement every 10 seconds. In alternative embodiments, the clock 308 runs faster or slower triggering measurements more or less frequently depending on how quickly the blood glucose level can change, the sensor sensitivity, how often new measurements are needed to control the delivery system 14, or the like.

Finally, in other alternative embodiments, other sensor signals from other types of sensors, as discussed in the section "Sensor and Sensor Set" below, are converted to digital sensor values Dsig if necessary before transmitting the digital sensor values Dsig to another device.

Additional Controller Inputs

Generally, the proportional plus, integral plus, derivative (PID) insulin response controller uses only glucose (digital sensor values Dsig) as an input. Conversely, in a normally glucose tolerant human body, healthy β-cells benefit from additional inputs such as neural stimulation, gut hormone stimulation, changes in free fatty acid (FFA) and protein stimulation etc. Thus in other alternative embodiments, the PID controller, as discussed above, can be augmented with one or more additional inputs. In particular alternative embodiments, the user may manually input supplemental information such as a start of a meal, an anticipated carbohydrate content of the meal, a start of a sleep cycle, an anticipated sleep duration, a start of an exercise period, an anticipated exercise duration, an exercise intensity estimation, or the like. Then, a model predictive control feature assists the controller to use the supplemental information to anticipate changes in glucose concentration and modify the output commands accordingly. For example, in a NGT individual, neural stimulation triggers the β-cells to begin to secrete insulin into the blood stream before a meal begins, which is well before the blood glucose concentration begins to rise. So, in alternative embodiments, the user can tell the controller that a meal is beginning and the controller will begin to secrete insulin in anticipation of the meal.

In other alternative embodiments, the user or another individual may manually override the control system or select a different controller algorithm. For instance, in particular alternative embodiments, an individual may select to normalize to a basal glucose level immediately, and instead of using the β-cell emulating PID controller another controller would take over such as a PID controller with different gains, a PD controller for rapid glucose adjustment, or the like. Additional alternative embodiments allow an individual to turn off the integral component of the PID controller once the glucose level is normalized and no meals are anticipated. In other particular alternative embodiments, the user may select to turn off the controller entirely, therefore disengaging the closed loop system. Once the closed loop system is not controlling insulin dosing, the user may program the infusion device with a basal rate, variable basal rates, boluses, or the like, or the user may manually enter each individual dosage when it is needed.

In still other alternative embodiments, more than one body characteristic is measured, and the measurements are provided as inputs to a controller. Measured body characteristics that may be used by the controller include, but are not limited to, the blood glucose level, blood and/or ISF pH, body temperature, the concentration of amino acids in blood (including arginine and/or lysine, and the like), the concentration of gastrointestinal hormones in blood or ISF (including gastrin, secretin, cholecystokinin, and/or gastro inhibitory peptide, and the like), the concentration of other hormones in blood or ISF (including glucagons, growth hormone, cortisol, progesterone and/or estrogen, and the like), blood pressure, body motion, respiratory rate, heart rate, and other parameters.

In NGT individuals, the glucose-induced secretion of insulin by healthy β-cells may be as much as doubled in the presence of excess amino acids. Yet, the presence of excess amino acids alone, without elevated blood glucose, only mildly increases insulin secretions according to the *Textbook of Medical Physiology*, Eighth Edition, written by Arthur C. Guyton, published by W. B. Saunders Company, 1991, Ch. 78, pg. 861, section "Other Factors That Stimulate Insulin Secretion". In particular alternative embodiments, amino acid concentrations are estimated or measured, and the controller's insulin response increases when amino acid concentrations are sufficiently high.

In NGT individuals, the presence of sufficient quantities of gastrointestinal hormones in the blood causes an anticipatory increase in blood insulin, which suggests that β-cells release insulin before increases in blood glucose due to an individual's anticipation of a meal. In particular alternative embodiments, the concentration of gastrointestinal hormones is measured or estimated, and when concentrations are high enough to indicate that a meal is anticipated, the controller commands are adjusted to cause insulin introduction into the body even before the blood glucose level changes. In other alternative embodiments, the controller uses measurements or estimates of other hormones to modify the rate of insulin secretion.

In NGT individuals, the body's cells take up glucose during periods of heavy exercise with significantly lower levels of insulin. In alternative embodiments, physiologic parameters such as body motion, blood pressure, pulse rate, respiratory rate, or the like, are used to detect periods of heavy exercise by the body and therefore provide inputs to the controller that decreases (or eliminates) the amount of insulin infused into the body to compensate for glucose concentrations.

Sensor Compensation and End-of-Life Detection

In particular embodiments, the sensor sensitivity 510 may degrade over time, as shown in FIG. 31(*b*). As the sensor sensitivity 510 changes the sensor signal accuracy degrades. If the sensor sensitivity 510 changes significantly then the sensor must be recalibrated or replaced. A diagnostic signal may be used to evaluate whether sensor signal accuracy has changed and/or may be used to adjust the signal or to indicate when to recalibrate or replace the sensor. As the sensor sensitivity 510 decreases, the measured glucose level 512 using the sensor signal underestimates the actual blood glucose level 514, and the measurement error 516 between the measured glucose level 512 and the actual blood glucose level 514 becomes greater over time, as shown in FIG.

31(a). The sensor sensitivity 510 decreases due to increases in sensor resistance Rs, as shown in FIG. 31(c). The sensor resistance Rs is the resistance provided by the body between the working electrode WRK and the counter electrode CNT, shown as the sum or R1 and R2 in the circuit diagram of FIG. 7. The sensor resistance Rs can be obtained indirectly by measuring the analog sensor signal Isig and the counter electrode voltage Vcnt and then calculating the resistance, $$Rs = Vcnt/Isig.$$

As the sensor resistance Rs increases, the analog sensor signal Isig response to a given glucose concentration decreases. In preferred embodiments, the decrease in the analog sensor signal Isig may be compensated for by identifying the amount that the sensor resistance Rs has changed since the last calibration and then using the change in resistance in a correction algorithm 454 to adjust the analog sensor signal value. A compensation value calculated by the correction algorithm 454 is used to increase the sensor analog signal value. The compensation value increases over time as the sensor resistance Rs increases. The correction algorithm 454 includes at least one value that varies with changes in sensor resistance Rs. In particular embodiments, a low pass filter is applied to the sensor resistance Rs measurement to decrease high frequency noise before evaluating how much the sensor resistance Rs has changed since the last calibration.

In alternative embodiments, the sensor resistance Rs may be calculated using different equations. For instance, a sensor resistance $Rs_2$ may be calculated as:

$$Rs_2 = (V_0 - Vcnt)/Isig$$

Figure 38:
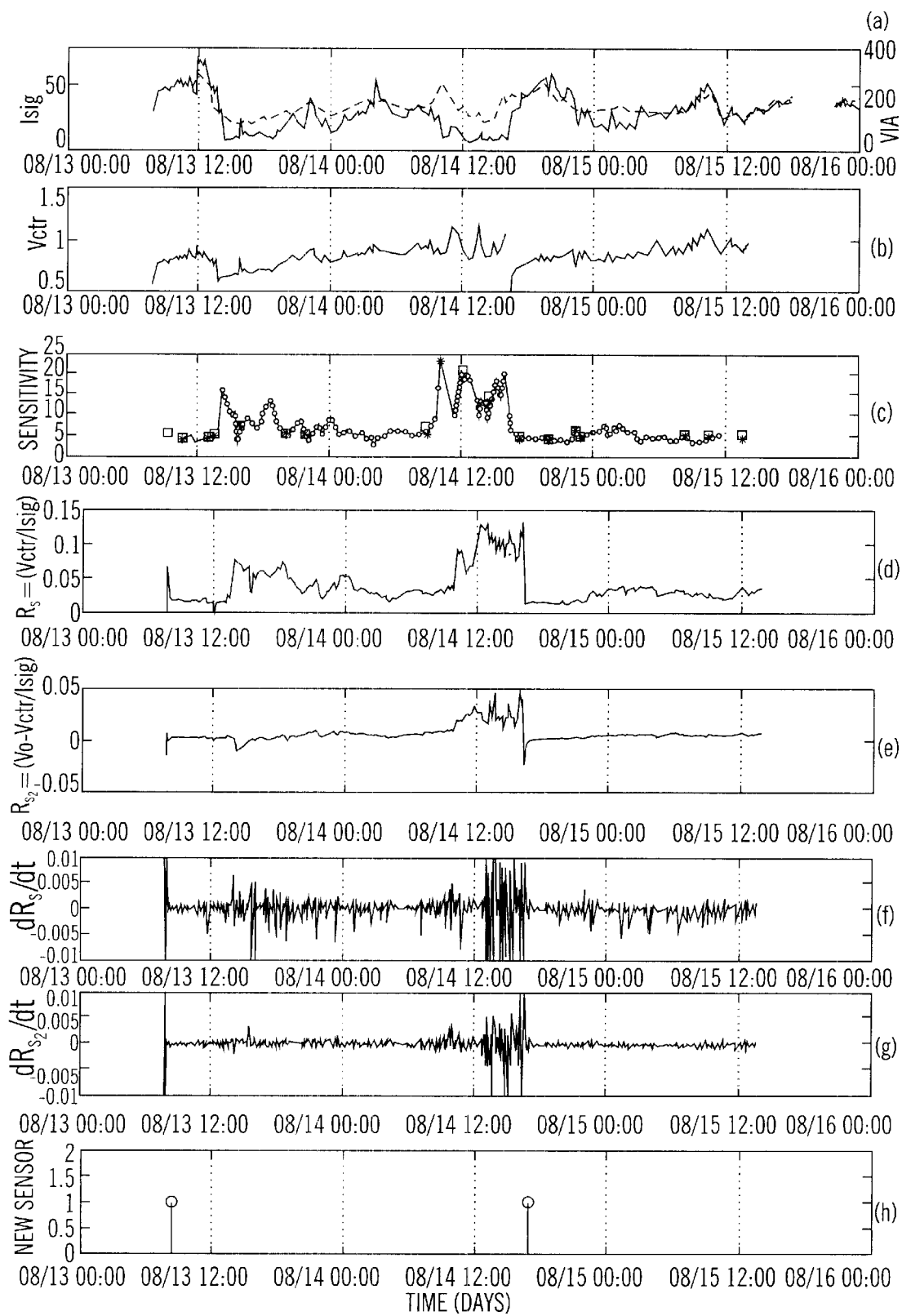
FIG. 38(a) is a plot of sensor signal measurements and Via measurements with respect to time in accordance with an embodiment of the present invention.
FIG. 38(b) is a plot of a measured counter electrode voltage Vcnt with respect to time in accordance with an embodiment of the present invention.
FIG. 38(c) is a plot of calculated sensor sensitivity with respect to time in accordance with an embodiment of the present invention.
FIG. 38(d) is a plot of a calculation of sensor resistance $Rs_1$ with respect to time in accordance with an embodiment of the present invention.
FIG. 38(e) is a plot of another calculation of sensor resistance $Rs_2$ with respect to time in accordance with an embodiment of the present invention.
FIG. 38(f) is a plot of the derivative of sensor resistance $Rs_1$ of FIG. 38(d) with respect to time in accordance with an embodiment of the present invention.
FIG. 38(g) is a plot of the derivative of the sensor resistance $Rs_2$ of FIG. 38(e) with respect to time in accordance with an embodiment of the present invention.
FIG. 38(h) is a plot of when sensors were replaced with respect to time in accordance with an embodiment of the present invention.

In particular embodiments, $V_0$ is the same voltage as Vset. An advantage of this approach is that it accounts for the voltage level Vset, which can vary from sensor to sensor and/or monitor to monitor, and/or as the analog sensor signal changes. This removes the noise and/or offset associated with variations in Vset, and can provide a more accurate indication of sensor resistance. In other particular embodiments, $V_0$ is set at −0.535 volts, which is a commonly used voltage for Vset. In further embodiments, $V_0$ is calculated from paired measurements of Vcnt and Isig. Using least squares or another curve fitting method, a mathematical equation representing the curve (typically a straight line equation) is derived from the relationship between Vcnt and Isig. Then, $V_0$ is obtained by extrapolating the curve to find the value for Vcnt when Isig is zero. FIGS. 38 (a–h) show a comparison between calculating the sensor resistance with $V_0$ and without $V_0$. The plot of the derivative of $Rs_2$ shown in FIG. 38(g) is cleaner and indicates the sensor failure more clearly than the plot of the derivative of Rs shown in FIG. 38(f). Hence sensor resistance $Rs_2$ may be used instead of, or in conjunction with, sensor resistance Rs described above.

Figure 32:
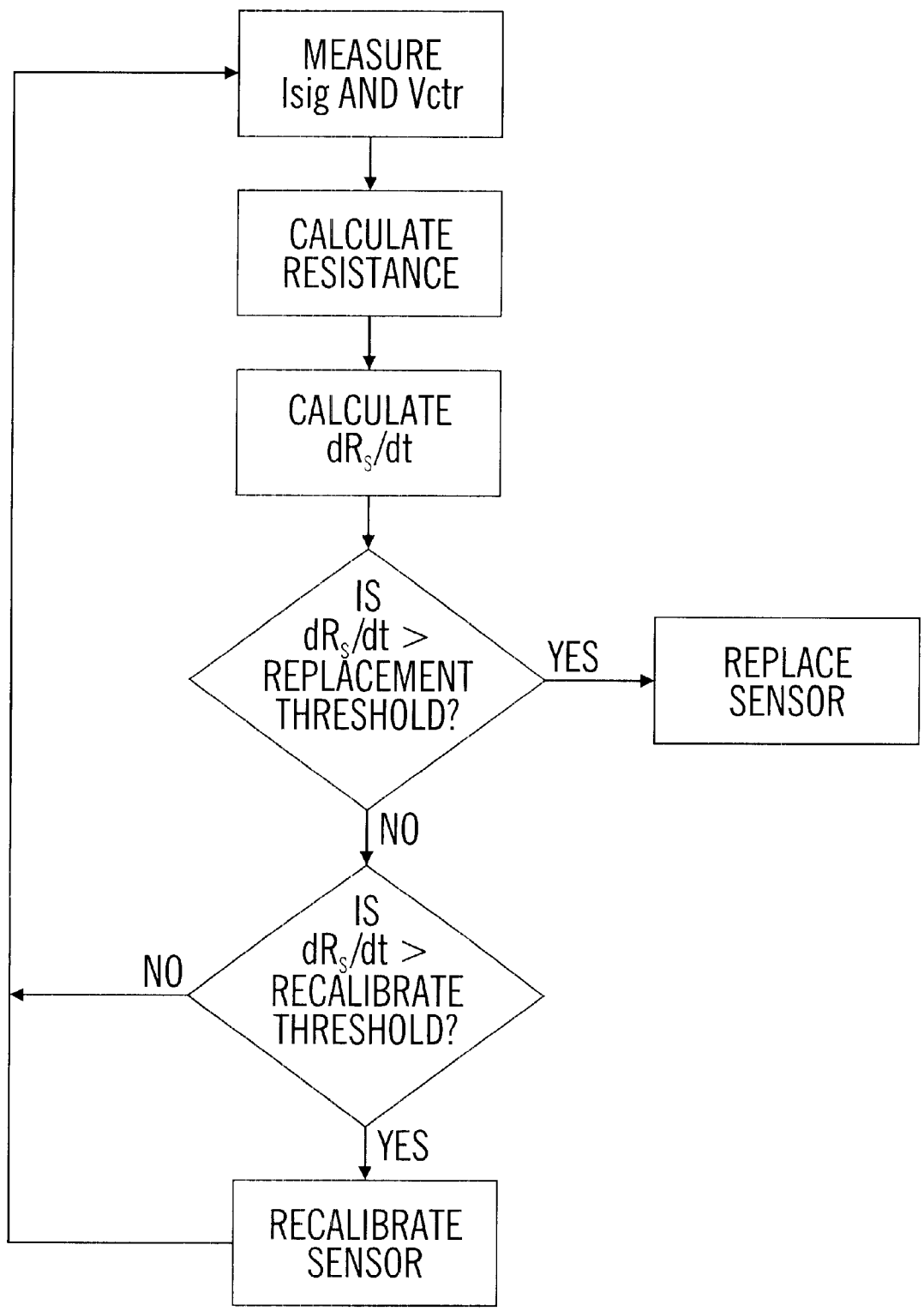
FIG. 32 is a block diagram using the derivative of sensor resistance to determine when to recalibrate or replace the sensor in accordance with an embodiment of the present invention.

In preferred embodiments, the sensor is recalibrated or replaced when the change in the sensor resistance Rs since the last calibration exceeds a threshold, or the rate of change of the sensor resistance dRs/dt exceeds another threshold. In particular embodiments, the rate of change of the sensor resistance dRs/dt may be compared to two thresholds as shown in FIG. 32. If dRs/dt exceeds a 'replacement' threshold then a warning is provided to the user to replace the sensor. If dRs/dt exceeds a 'recalibrate' threshold then a warning is provided to the user to recalibrate the sensor.

Figure 33:
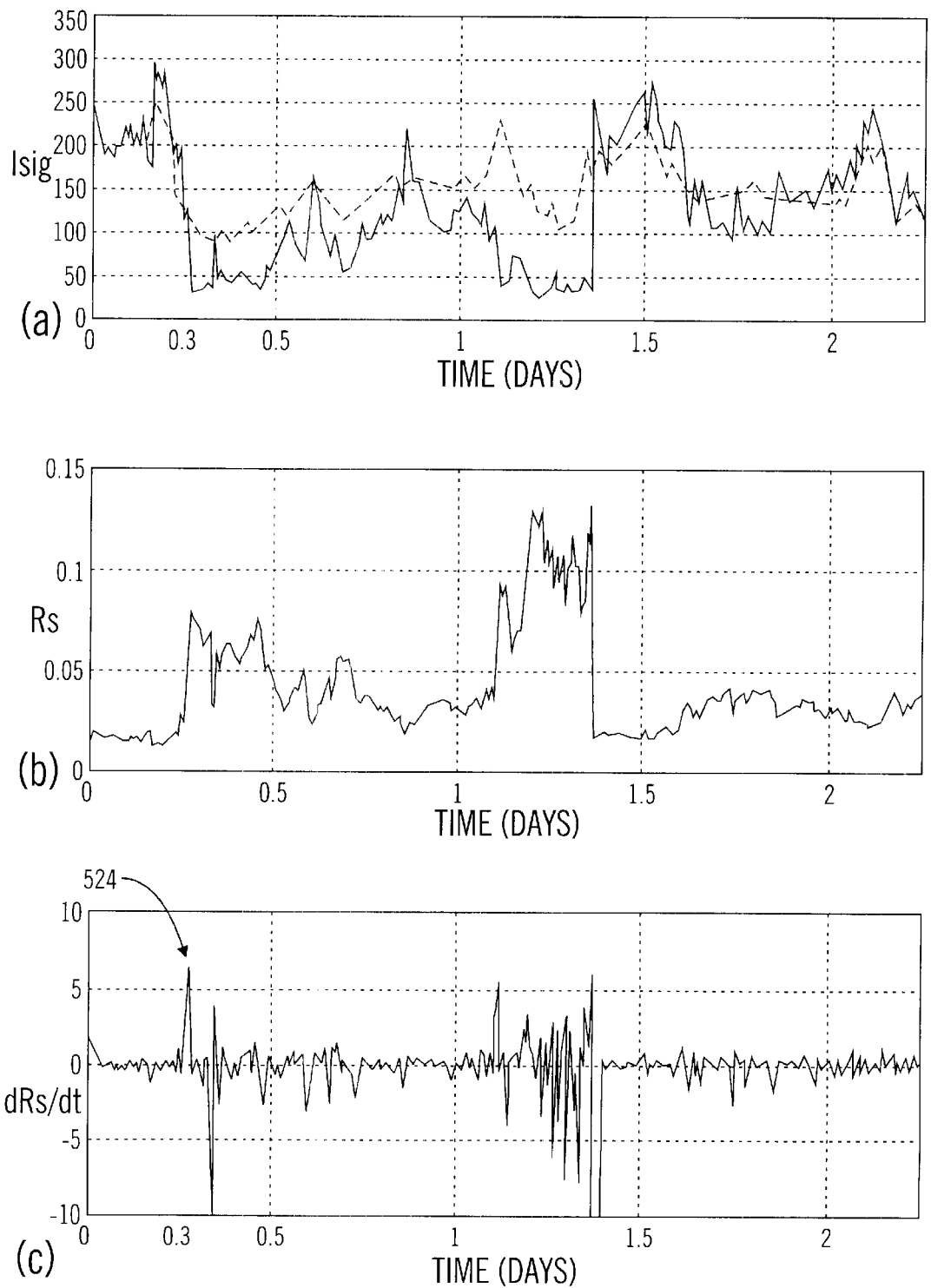
FIG. 33(a) is a plot of an analog sensor signal Isig over time in accordance with an embodiment of the present invention.
FIG. 33(b) is a plot of sensor resistance over the same period of time as FIG. 32(a) in accordance with an embodiment of the present invention.
FIG. 33(c) is a plot of the derivative of the sensor resistance of FIG. 32(b) in accordance with an embodiment of the present invention.

In an example shown in FIGS. 33(a–c), the analog sensor signal Isig decreases dramatically at approximately 0.3 days, as seen in FIG. 33(a). Given only the analog sensor signal Isig, the user would believe that the decrease in the analog sensor signal Isig is due to a decrease in blood glucose. But in reality the drop in the analog sensor signal Isig is due to a sudden change in sensor sensitivity. The sensor resistance Rs, shown in FIG. 33(b) increases as the analog sensor signal Isig drops at about 0.3 days. The derivative of the sensor resistance dRs/dt, shown in FIG. 33(c), clearly shows a spike 522 at about 0.3 days when the analog sensor signal Isig dropped. The spike 522 in the change in sensor resistance dRs/dt indicates a sensor anomaly rather than a realistic drop in blood glucose. If a threshold were placed at +/−4 on the dRs/dt, the user would have received a warning to replace the sensor at about 0.3 days. As seen in FIG. 33(a), the sensor was not replaced until about 1.4 days. The analog sensor signal Isig was under estimating the true glucose level from about 0.3 days until the sensor was replaced at about 1.4 days.

In particular embodiments, the amount of time dt over which the derivative of the sensor resistance Rs is taken is the entire time since the last calibration. In other embodiments, the amount of time dt over which the derivative is taken is fixed, for example over the last hour, 90 minutes, 2 hours, or the like.

In alternative embodiments, the sensor is recalibrated or replaced when the integral of the sensor resistance Rs over a predetermined time window (∫ Rs d/dt) exceeds a predetermined resistance integral threshold. An advantage to this approach is that it tends to filter out potential noise that could be encountered from a signal that includes occasional spikes, sudden variations in voltage levels, or the like. Preferably, the integral of the sensor resistance Rs is calculated over a time window (such as 15 minutes, or the like) based on Rs measurements obtained at set rates (such as 1 minute, 5 minutes, or the like) during the time window. In alternative embodiments, the time windows may be longer or shorter and different sampling rates may be used, with the selection being dependent on noise, response of the system, sampling rate used in the controller, or the like. In further embodiments, the time windows and sampling rates may change over time, such as when approaching the end of the expected sensor life, or as the equations indicate that the sensor is degrading, or the like.

Like above, multiple thresholds may be used. For instance, if ∫ Rs d/dt exceeds a 'replacement' threshold then a warning is provided to the user to replace the sensor. And if ∫ Rs d/dt exceeds a 'recalibrate' threshold then a warning is provided to the user to recalibrate the sensor. In further alternative embodiments, the counter electrode voltage Vcnt is used to evaluate other characteristics such as, sensor accuracy, sensor bio-fouling, sensor function, sensor voltage operating range, sensor attachment, or the like.

pH Controller Input

Figure 30:
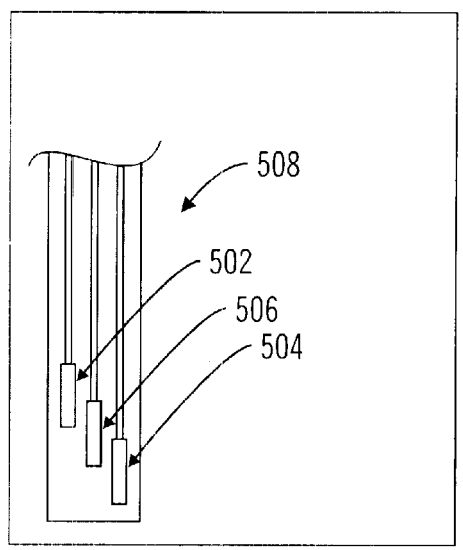
FIG. 30 is a top view of an end of a multi-sensor for measuring both glucose concentration and pH in accordance with an embodiment of the present invention.

In alternative embodiments, the controller uses measurements of both the interstitial fluid (ISF) glucose level and a local pH in the ISF surrounding the sensor to generate commands for the infusion device. In particular alternative embodiments, a single multi-sensor 508 located in the subcutaneous tissue is used to measure both the glucose level and the pH. The tip of the multi-sensor 508 that is placed into the subcutaneous tissue with three electrodes is shown in FIG. 30. The working electrode 502 is plated with platinum black and coated with glucose oxidase (GOX). The reference electrode 506 is coated with silver-silver chloride. And the counter electrode 504 is coated with iridium oxide (Ir Ox). The analog sensor signal Isig is generated at the working electrode 502 due to the reaction between glucose oxidase GOX and the ISF glucose as described with the preferred sensor embodiment. In this alternative embodiment however, as glucose in the ISF reacts with the glucose oxidase GOX on the working electrode and gluconic acid is generated, the local pH in the ISF surrounding the sensor decreases, which changes the potential of the iridium oxide on the counter electrode 504, with respect to the reference electrode REF. So, as the pH decreases, the voltage at the counter electrode 504 increases. Therefore, as the glucose concentration increases, the local pH decreases, which causes the counter electrode voltage to increase. So, the glucose concentration may be estimated based on the counter electrode voltage. The counter electrode voltage estimate of glucose concentration can be compared to the estimate of glucose level from the analog sensor signal Isig. The two estimates of the glucose level may be combined by a weighted average or one estimate may simply be used as a check to verify that the other sensing method is functioning properly. For example, if the difference between the two estimates is 10% for a period of time and then suddenly the difference increased to 50%, a warning would be issued indicating to the user that the sensor may need to be replaced or recalibrated.

In additional alternative embodiments, the pH level near the sensor may be used to detect infection. By tracking trends in the pH over time, a dramatic change in pH may be used to identify that an infection has developed in proximity to the sensor. A warning is used to notify the user to replace the sensor.

The pH sensor may be used in other embodiments. When insulin is not available to assist the body to use glucose, the body shifts to consuming fat for energy. As the body shifts from using glucose to using almost exclusively fat for energy, concentrations of keto acids (acetoacetic acid and β-hydroxybutyric acid) increase from about 1 mEq/liter to as high as 10 mEq/liter. In particular alternative embodiments, the pH level is measured to detect increases in keto acids in the body. In embodiments of the present invention, a warning is provided to the user when the ISF pH level is too low.

A side effect of the increased of keto acid concentrations is that sodium is drawn from the body's extra cellular fluid to combine with the acids so that the body can excrete the acids. This leads to increased quantities of hydrogen ions, which greatly increases the acidosis. Severe cases lead to rapid deep breathing, acidotic coma and even death. In other alternative embodiments, an ion-selective electrode (ISE) is used to detect changes in sodium concentration. A special membrane is used to coat the ISE so that it only senses changes in sodium concentration. In particular alternative embodiments, the ISE is a fourth electrode added to the glucose sensor. In another alternative embodiment, a three-electrode system is used with a silver-silver chloride reference electrode REF, an Ir Ox counter electrode CNT, and a sodium ion-selective (Na ISE) working electrode WRK.

While pH measurements, end-of-life measurements, hormone measurements, or the like, add inputs to the controller that can significantly affect the accuracy of insulin delivery, the basic input to the controller is generally a glucose measurement. The glucose measurement is provided by the sensor system. And once the controller uses the glucose measurement to generate commands, the delivery system executes the commands. The following is a detailed description of several apparatus embodiments for the sensor system and the delivery system.

Sensor System

The sensor system provides the glucose measurements used by the controller. The sensor system includes a sensor, a sensor set to hold the sensor if needed, a telemetered characteristic monitor transmitter, and a cable if needed to carry power and/or the sensor signal between the sensor and the telemetered characteristic monitor transmitter.

Sensor and Sensor Set

In preferred embodiments, the glucose sensor system 10 includes a thin film electrochemical sensor such as the type disclosed in U.S. Pat. No. 5,391,250, entitled "METHOD OF FABRICATING THIN FILM SENSORS"; U.S. patent application Ser. No. 09/502,204, filed on Feb. 10, 2000, entitled "IMPROVED ANALYTE SENSOR AND METHOD OF MAKING THE SAME"; or other typical thin film sensors such as described in commonly assigned U.S. Pat. Nos. 5,390,671; 5,482,473; and 5,586,553 which are incorporated by reference herein. See also U.S. Pat. No. 5,299,571.

The glucose sensor system 10 also includes a sensor set 28 to support the sensor 26 such as described in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/56293); and U.S. Pat. No. 5,951,521, entitled "A SUBCUTANEOUS IMPLANTABLE SENSOR SET HAVING THE CAPABILITY TO REMOVE OR DELIVER FLUIDS TO AN INSERTION SITE", which are incorporated by reference herein.

In preferred embodiments, the sensor 26 is inserted through the user's skin 46 using an insertion needle 58, which is removed and disposed of once the sensor is positioned in the subcutaneous tissue 44. The insertion needle 58 has a sharpened tip 59 and an open slot 60 to hold the sensor during insertion into the skin 46, as shown in FIGS. 3(c) and (d) and FIG. 4. Further description of the needle 58 and the sensor set 28 are found in U.S. Pat. No. 5,586,553, entitled "TRANSCUTANEOUS SENSOR INSERTION SET" (published as PCT Application WO 96/25088); and U.S. Pat. No. 5,954,643, entitled "INSERTION SET FOR A TRANSCUTANEOUS SENSOR" (published as PCT Application WO 98/5629), which are incorporated by reference herein.

Figure 4:
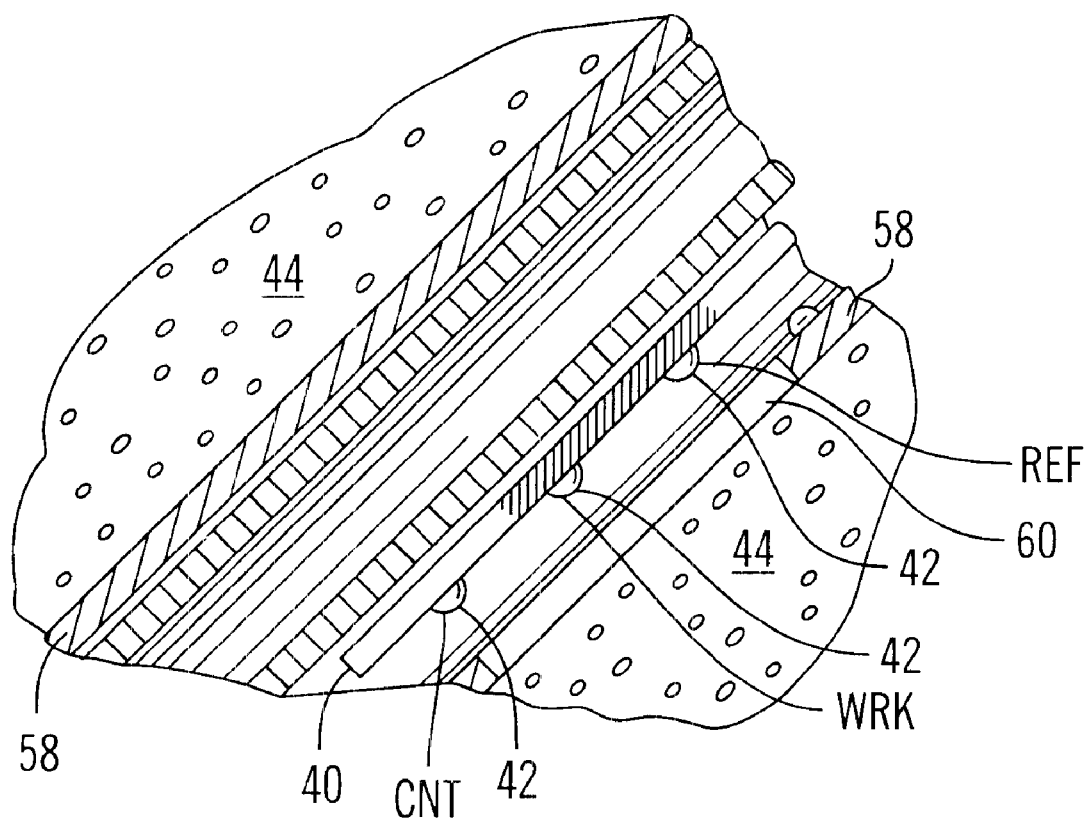
FIG. 4 is a cross sectional view of a sensing end of the sensor of FIG. 3(d).
Figure 7:
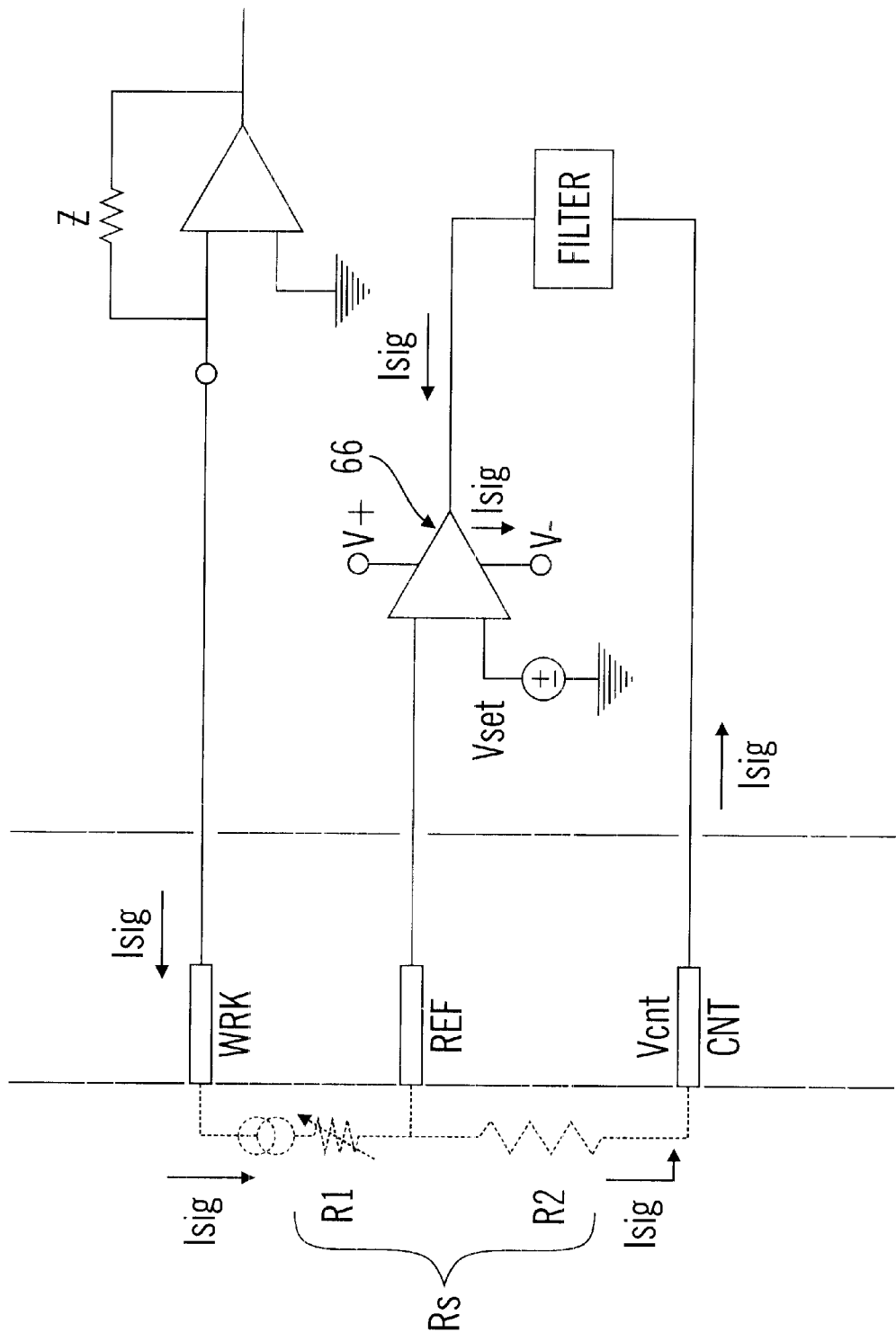
FIG. 7 is a circuit diagram of a sensor and its power supply in accordance with an embodiment of the present invention.

In preferred embodiments, the sensor 26 has three electrodes 42 that are exposed to the interstitial fluid (ISF) in the subcutaneous tissue 44 as shown in FIGS. 3(d) and 4. A working electrode WRK, a reference electrode REF and a counter electrode CNT are used to form a circuit, as shown in FIG. 7. When an appropriate voltage is supplied across the working electrode WRK and the reference electrode REF, the ISF provides impedance (R1 and R2) between the electrodes 42. And an analog current signal Isig flows from the working electrode WRK through the body (R1 and R2, which sum to Rs) and to the counter electrode CNT. Preferably, the working electrode WRK is plated with platinum black and coated with glucose oxidase (GOX), the reference electrode REF is coated with silver-silver chloride, and the counter electrode is plated with platinum black. The voltage at the working electrode WRK is generally held to ground, and the voltage at the reference electrode REF is substantially held at a set voltage Vset. Vset is between 300 and 700 mV, and preferably to about 535 mV.

The most prominent reaction stimulated by the voltage difference between the electrodes is the reduction of glucose as it first reacts with GOX to generate gluconic acid and hydrogen peroxide ($H_2O_2$). Then the $H_2O_2$ is reduced to water ($H_2O$) and ($O^-$) at the surface of the working electrode WRK. The $O^-$ draws a positive charge from the sensor electrical components, thus repelling an electron and causing an electrical current flow. This results in the analog current signal Isig being proportional to the concentration of glucose in the ISF that is in contact with the sensor electrodes 42. The analog current signal Isig flows from the working electrode WRK, to the counter electrode CNT, typically through a filter and back to the low rail of an op-amp 66. An input to the op-amp 66 is the set voltage Vset. The output of the op-amp 66 adjusts the counter voltage Vcnt at the counter electrode CNT as Isig changes with glucose concentration. The voltage at the working electrode WRK is generally held to ground, the voltage at the reference electrode REF is generally equal to Vset, and the voltage Vcnt at the counter electrode CNT varies as needed.

In alternative embodiments, more than one sensor is used to measure blood glucose. In particular embodiments, redundant sensors are used. The user is notified when a sensor fails by the telemetered characteristic monitor transmitter electronics. An indicator may also inform the user of which sensors are still functioning and/or the number of sensors still functioning. In other particular embodiments, sensor signals are combined through averaging or other means. If the difference between the sensor signals exceeds a threshold then the user is warned to recalibrate or replace at least one sensor. In other alternative embodiments, more than one glucose sensor is used, and the glucose sensors are not of the same design. For example, an internal glucose sensor and an external glucose sensor may be used to measure blood glucose at the same time.

Figure 34:
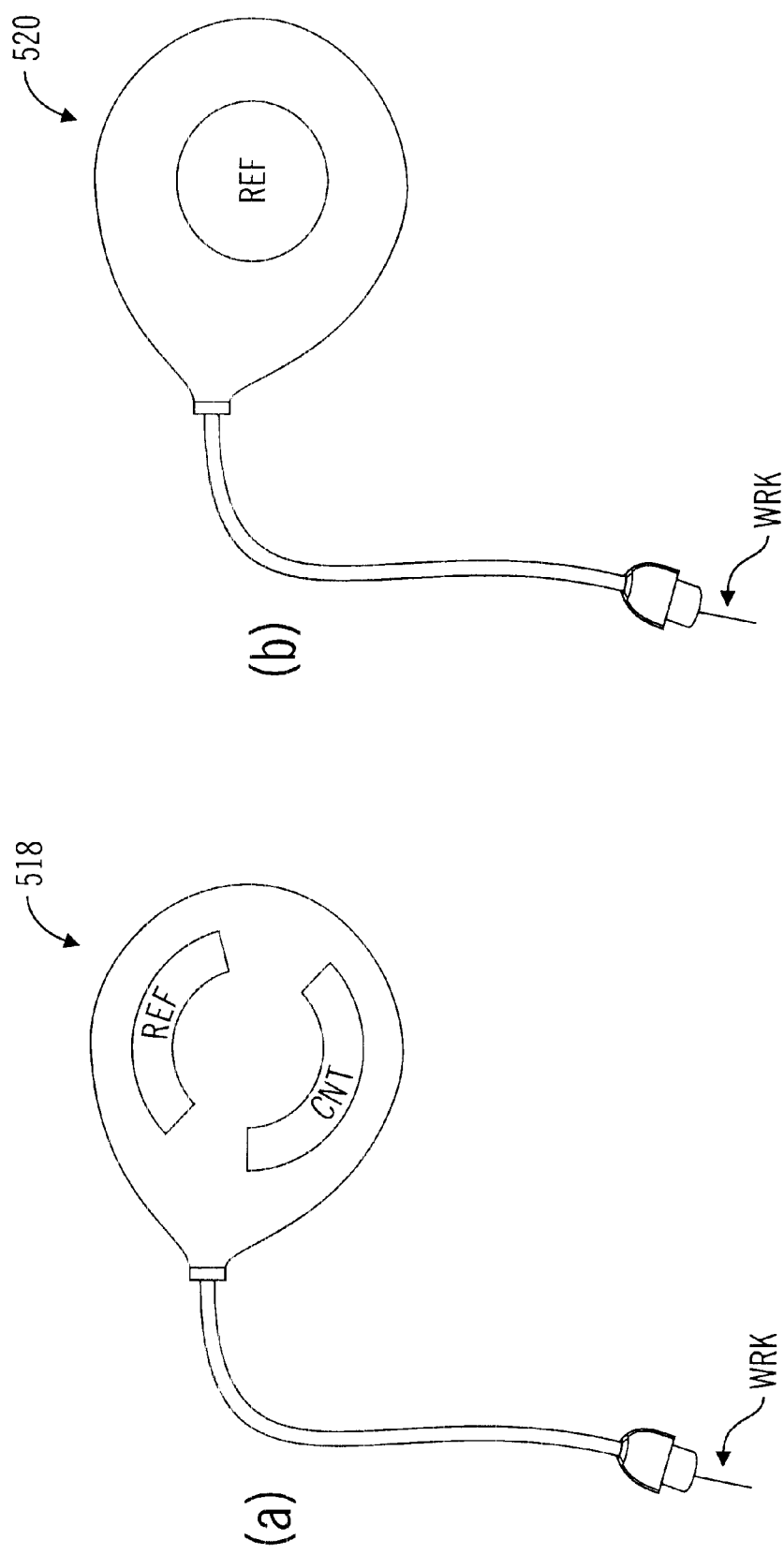
FIG. 34(a) is a bottom view of a telemetered characteristic monitor in accordance with an embodiment of the present invention.
FIG. 34(b) is a bottom view of a different telemetered characteristic monitor in accordance with an embodiment of the present invention.

In alternative embodiments, other continuous blood glucose sensors and sensor sets may be used. In particular alternative embodiments, the sensor system is a micro needle analyte sampling device such as described in U.S. patent application Ser. No. 09/460,121, filed on Dec. 13, 1999, entitled "INSERTION SET WITH MICROPIERCING MEMBERS AND METHODS OF USING THE SAME", incorporated by reference herein, or an internal glucose sensor as described in U.S. Pat. Nos. 5,497,772; 5,660,163; 5,791,344; and 5,569,186, and/or a glucose sensor that uses florescence such as described in U.S. Pat. No. 6,011,984 all of which are incorporated by reference herein. In other alternative embodiments, the sensor system uses other sensing technologies such as described in Patent Cooperation Treaty publication No. WO 99/29230, light beams, conductivity, jet sampling, micro dialysis, microporation, ultra sonic sampling, reverse iontophoresis, or the like. In still other alternative embodiments, only the working electrode WRK is located in the subcutaneous tissue and in contact with the ISF, and the counter CNT and reference REF electrodes are located external to the body and in contact with the skin. In particular embodiments, the counter electrode CNT and the reference electrode REF are located on the surface of a monitor housing 518 and are held to the skin as part of the telemetered characteristic monitor, as shown in FIG. 34(a). In other particular embodiments, the counter electrode CNT and the reference electrode REF are held to the skin using other devices such as running a wire to the electrodes and taping the electrodes to the skin, incorporating the electrodes on the underside of a watch touching the skin, or the like. In more alternative embodiments, more than one working electrode WRK is placed into the subcutaneous tissue for redundancy. In additional alternative embodiments, a counter electrode is not used, a reference electrode REF is located outside of the body in contact with the skin, and one or more working electrodes WRK are located in the ISF. An example of this embodiment implemented by locating the reference electrode REF on a monitor housing 520 is shown in FIG. 34(b).

In other embodiments, ISF is harvested from the body of an individual and flowed over an external sensor that is not implanted in the body.

Sensor Cable

In preferred embodiments, the sensor cable 32 is of the type described in U.S. patent application Ser. No. 60/121, 656, filed on Feb. 25, 1999, entitled "TEST PLUG AND CABLE FOR A GLUCOSE MONITOR", which is incorporated by reference herein. In other embodiments, other cables may be used such as shielded, low noise cables for carrying nA currents, fiber optic cables, or the like. In alternative embodiments, a short cable may be used or the sensor may be directly connected to a device without the need of a cable.

Telemetered Characteristic Monitor Transmitter

In preferred embodiments, the telemetered characteristic monitor transmitter 30 is of the type described in U.S. patent application Ser. No. 09/465,715, filed on Dec. 17, 1999, entitled "TELEMETERED CHARACTERISTIC MONITOR SYSTEM AND METHOD OF USING THE SAME" (published as PCT Application WO 00/19887 and entitled, "TELEMETERED CHARACTERISTIC MONITOR SYSTEM"), which is incorporated by reference herein, and is connected to the sensor set 28 as shown in FIGS. 3 (a) and (b).

In alternative embodiments, the sensor cable 32 is connected directly to the infusion device housing, as shown in FIG. 8(a), which eliminates the need for a telemetered characteristic monitor transmitter 30. The infusion device contains a power supply and electrical components to operate the sensor 26 and store sensor signal values.

In other alternative embodiments, the telemetered characteristic monitor transmitter includes a receiver to receive updates or requests for additional sensor data or to receive a confirmation (a hand-shake signal) indicating that information has been received correctly. Specifically, if the telemetered characteristic monitor transmitter does not receive a confirmation signal from the infusion device, then it re-sends the information. In particular alternative embodiments, the infusion device anticipates receiving blood glucose values or other information on a periodic basis. If the expected information is not supplied when required, the infusion device sends a 'wake-up' signal to the telemetered characteristic monitor transmitter to cause it to re-send the information.

Insulin Delivery System

Infusion Device

Once a sensor signal 16 is received and processed through the controller 12, commands 22 are generated to operate the infusion device 34. In preferred embodiments, semi-automated medication infusion devices of the external type are used, as generally described in U.S. Pat. Nos. 4,562,751; 4,678,408; 4,685,903; and U.S. patent application Ser. No. 09/334,858, filed on Jun. 17, 1999, entitled "EXTERNAL INFUSION DEVICE WITH REMOTE PROGRAMMING, BOLUS ESTIMATOR AND/OR VIBRATION CAPABILITIES" (published as PCT application WO 00/10628), which are herein incorporated by reference. In alternative embodiments, automated implantable medication infusion devices, as generally described in U.S. Pat. Nos. 4,373,527 and 4,573,994, are used, which are incorporated by reference herein.

Insulin

In preferred embodiments, the infusion device reservoir 50 contains Humalog ® lispro insulin to be infused into the body 20. Alternatively, other forms of insulin may be used such as Humalin®, human insulin, bovine insulin, porcine insulin, analogs, or other insulins such as insulin types described in U.S. Pat. No. 5,807,315, entitled "METHOD AND COMPOSITIONS FOR THE DELIVERY OF MONOMERIC PROTEINS", and U.S. patent application Ser. No. 60/177,897, filed on Jan. 24, 2000, entitled "MIXED BUFFER SYSTEM FOR STABILIZING POLYPEPTIDE FORUMLATIONS", which are incorporated by reference herein, or the like. In further alternative embodiments, other components are added to the insulin such as polypeptides described in U.S. patent application Ser. No. 09/334,676, filed on Jun. 25, 1999, entitled "MULTIPLE AGENT DIABETES THERAPY", small molecule insulin mimetic materials such as described in U.S. patent application Ser. No. 09/566877, filed on May 8, 2000, entitled "DEVICE AND METHOD FOR INFUSION OF SMALL MOLECULE INSULIN MIMETIC MATERIALS", both of which are incorporated by reference herein, or the like.

Infusion Tube

In preferred embodiments, an infusion tube 36 is used to carry the insulin 24 from the infusion device 34 to the infusion set 38. In alternative embodiments, the infusion tube carries the insulin 24 from infusion device 34 directly into the body 20. In further alternative embodiments, no infusion tube is needed, for example if the infusion device is attached directly to the skin and the insulin 24 flows from the infusion device, through a cannula or needle directly into the body. In other alternative embodiments, the infusion device is internal to the body and an infusion tube may or may not be used to carry insulin away from the infusion device location.

Infusion Set

In preferred embodiments, the infusion set 38 is of the type described in U.S. Pat. No. 4,755,173, entitled "SOFT CANNULA SUBCUTANEOUS INJECTION SET", which is incorporated by reference herein. In alternative embodiments, other infusion sets, such as the Rapid set from Desetronic, the Silhouette from MiniMed, or the like, may be used. In further alternative embodiments, no infusion set is required, for example if the infusion device is an internal infusion device or if the infusion device is attached directly to the skin.

Configurations With Supplemental Devices

In further alternative embodiments, the pre-filter, filters, calibrator and/or controller 12 are located in a supplemental device that is in communication with both the telemetered characteristic monitor transmitter 30 and the infusion device 34. Examples of supplemental devices include, a hand held personal digital assistant such as described in U.S. patent application Ser. No. 09/487,423, filed on Jan. 20, 2000, entitled "HANDHELD PERSONAL DATA ASSISTANT (PDA) WITH A MEDICAL DEVICE AND METHOD OF USING THE SAME", which is incorporated by reference herein, a computer, a module that may be attached to the telemetered characteristic monitor transmitter 30, a module that may be attached to the infusion device 34, a RF programmer such as described in U.S. patent application Ser. No. 09/334,858, filed on Jun. 17, 1999, entitled EXTERNAL INFUSION DEVICE WITH REMOTE PROGRAMMING, BOLUS ESTIMATOR AND/OR VIBRATION CAPABILITIES (published as PCT application WO 00/10628), which is incorporated by reference herein, or the like. In particular embodiments, the supplemental device includes a post-calibration filter, a display, a recorder, and/or a blood glucose meter. In further alternative embodiments, the supplemental device includes a method for a user to add or modify information to be communicated to the infusion device 34 and/or the telemetered characteristic monitor transmitter 30 such as buttons, a keyboard, a touch screen, and the like.

In particular alternative embodiments, the supplemental device is a computer in combination with an analyte monitor and a RF programmer. The analyte monitor receives RF signals from the telemetered characteristic monitor transmitter 30, stores the signals and down loads them to a computer when needed. The RF programmer sends control signals to the infusion device 34 to reprogram the rate of insulin infusion. Both the analyte monitor and the RF programmer are placed into separate communication stations. The communication stations include IR transmitters and IR receivers to communicate with the analyte monitor and the RF programmer. The sensor signal values are transmitted via the telemetered characteristic monitor transmitter 30 to the analyte monitor located in one of the communication stations. Then the sensor signal values are communicated through the IR receiver in a first communication station and to the computer. The computer processes the sensor signal values through one or more filters, calibrators, and controllers to generate commands 22. The commands are sent to a second communication station and sent to an RF programmer by the IR transmitter in the communication station. Finally the RF programmer transmits the commands 22 to the infusion device 34. The communication station, analyte monitor and infusion device 34 may be of the type described in U.S. patent application Ser. No. 09/409,014, filed on Sep. 29, 1999 entitled COMMUNICATION STATION FOR INTERFACING WITH AN INFUSION PUMP, ANALYTE MONITOR, ANALYTE METER OR THE LIKE (published as a PCT application WO 00/18449), which is incorporated by reference herein. Alternatively, the RF programmer may be omitted and the infusion device may be placed in a communication station, or the infusion device may receive the commands without the use of an RF programmer and/or a communication station.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A closed loop infusion system for infusing a fluid into a user, the system comprising:

a sensor system that includes a sensor for monitoring glucose concentration of the user, and produces a sensor signal, which is representative of the glucose concentration of the user, and wherein the sensor signal is used to generate a controller input;

a proportional plus, integral plus, derivative (PID) controller that uses the controller input to generate commands; and a delivery system that infuses a liquid, which includes insulin, into the user, wherein the operation of the delivery system is affected by the commands.

2. A closed loop infusion system according to claim 1, wherein the controller is influenced by one or more manual inputs from the user.

3. A closed loop infusion system according to claim 1, wherein the one or more manual inputs from the user includes at least one of the group consisting of the start of a meal, the number of carbohydrates in a meal, the beginning of exercise for the body of the user, the duration of the exercise for the body of the user, the start of sleep for the user, and the duration of sleep for the user.

4. A closed loop infusion system according to claim 1, wherein one or more controller gains are selected such that the commands generated by the controller cause the delivery system to infuse insulin into the body of the user in response to a glucose concentration at a rate similar to the rate that beta cells would release insulin in an individual with a healthy normally functioning pancreas.

5. A closed loop infusion system according to claim 4, wherein one or more controller gains are selected by a method that includes the step of measuring an insulin response of at least one individual with a healthy normally functioning pancreas and calculating the controller gains that cause the commands to generally match the insulin response of at least one individual.

6. A closed loop infusion system according to claim 1, wherein the controller is influenced by inputs of more than one measured body characteristic.

7. A closed loop infusion system according to claim 6, wherein the more than one measured body characteristic includes one or more measured body characteristics from a group including one or more amino acid concentrations, one or more gastrointestinal hormone concentrations, one or more other hormone concentrations, blood pH, interstitial fluid (ISF) pH, one or more blood glucose concentrations, and one or more interstitial fluid (ISF) glucose concentrations.

8. A closed loop infusion system according to claim 1, wherein the sensor is a multi-sensor that measures both glucose concentration and pH.

9. A closed loop infusion system according to claim 1, wherein the sensor system produces a diagnostic signal in addition to the sensor signal, and wherein the diagnostic signal is used to indicate when the sensor signal accuracy has diminished.

10. A closed loop infusion system according to claim 1, wherein one or more controller gains are selected such that the commands generated by the controller cause the delivery system to infuse insulin into the body of the user in response to a glucose concentration at a rate such that the insulin concentration profile in the user's blood stream is similar to the insulin concentration profile that would be generated by the release of insulin beta cells in an individual with a healthy normally functioning pancreas.

11. A closed loop infusion system according to claim 1, wherein the derivative gain $K_D$ is calculated using the first phase insulin response ($\phi 1$) measured from a normal glucose tolerant (NGT) individual.

12. A closed loop infusion system according to claim 1, wherein one or more controller gains are calculated from a ratio of one or more controller gains.

13. A closed loop infusion system according to claim 1, wherein a post-controller lead/lag compensator is used to modify the commands generated by the controller to cause the delivery system to infuse insulin into the body of the user in response to a glucose concentration at a rate such that the insulin concentration profile in the user's blood stream is similar to the insulin concentration profile that would be generated by the release of insulin beta cells in an individual with a healthy normally functioning pancreas.

14. A closed loop infusion system according to claim 1, wherein a post-controller lead/lag compensator is used to modify the commands generated by the controller to compensate for an insulin delivery delay due to infusing insulin into a user' tissue rather than directly into the user's blood stream.

* * * * *